(12) United States Patent
Xu et al.

(10) Patent No.: US 11,529,425 B2
(45) Date of Patent: *Dec. 20, 2022

(54) IMMUNOCONJUGATES COMPRISING SIGNAL REGULATORY PROTEIN ALPHA

(71) Applicant: DINGFU BIOTARGET CO., LTD., Suzhou (CN)

(72) Inventors: Ting Xu, Suzhou (CN); Kai Fu, Suzhou (CN); Yan Luan, Suzhou (CN); Xiaojuan Liu, Suzhou (CN); Jianjian Peng, Suzhou (CN)

(73) Assignee: Dingfu Biotarget Co., Ltd., Jiangsu (CN)

( * ) Notice: Subject to any disclaimer, the term of this patent is extended or adjusted under 35 U.S.C. 154(b) by 190 days.

This patent is subject to a terminal disclaimer.

(21) Appl. No.: 16/645,064

(22) PCT Filed: Sep. 6, 2018

(86) PCT No.: PCT/CN2018/104303
§ 371 (c)(1),
(2) Date: Mar. 6, 2020

(87) PCT Pub. No.: WO2019/047885
PCT Pub. Date: Mar. 14, 2019

(65) Prior Publication Data
US 2021/0162061 A1    Jun. 3, 2021

(30) Foreign Application Priority Data
Sep. 7, 2017   (WO) ............... PCT/CN2017/100872

(51) Int. Cl.
*A61K 47/68*   (2017.01)
*A61K 47/62*   (2017.01)
(Continued)

(52) U.S. Cl.
CPC ........ *A61K 47/6849* (2017.08); *A61K 31/704* (2013.01); *A61K 47/62* (2017.08);
(Continued)

(58) Field of Classification Search
CPC .. A61K 47/6849; A61K 47/62; A61K 31/704; A61K 38/00; A61K 2039/505;
(Continued)

(56) References Cited

U.S. PATENT DOCUMENTS

| 6,541,615 B1 | 4/2003 | Ullrich et al. | |
| 9,951,145 B2* | 4/2018 | Kim | C07K 16/2878 |
| 2015/0175707 A1* | 6/2015 | De Jong | C07K 16/2809 |
| | | | 424/9.1 |

FOREIGN PATENT DOCUMENTS

| CN | 106397592 A | 2/2017 |
| CN | 106519036 A | 3/2017 |

(Continued)

OTHER PUBLICATIONS

Liu, H., et al (2017) Fc engineering for Developing Therapeutic Bispecific Antibodies and Novel Scaffolds Frontiers in Immunology 8 (38); 1-15, published Jan. 26, 2017 (Year: 2017).*

(Continued)

*Primary Examiner* — Joanne Hama
*Assistant Examiner* — Audrey L Buttice
(74) *Attorney, Agent, or Firm* — Honigman LLP; Thomas A. Wootton, Esq.; Jonathan P. O'Brien

(57) ABSTRACT

Provided is an immunoconjugate useful in inhibiting tumor growth, and a composition and/or protein mixture comprising the immunoconjugate. Also provided are methods for the production of the immunoconjugate, as well as pharmaceutical uses of the immunoconjugate in inhibiting tumor growth, including but not limited to treatment of cancers.

18 Claims, 14 Drawing Sheets

Specification includes a Sequence Listing.

(51) Int. Cl.
  *A61P 35/00*   (2006.01)
  *A61K 31/704*   (2006.01)
  *C07K 14/705*   (2006.01)
  *C07K 16/28*   (2006.01)
  *A61K 38/00*   (2006.01)
  *A61K 39/00*   (2006.01)

(52) U.S. Cl.
  CPC ........ *A61P 35/00* (2018.01); *C07K 14/70596* (2013.01); *C07K 16/2827* (2013.01); *A61K 38/00* (2013.01); *A61K 2039/505* (2013.01)

(58) Field of Classification Search
  CPC .............. A61P 35/00; C07K 14/70596; C07K 14/70503; C07K 16/2827; C07K 16/32; C07K 16/2803; C07K 2317/52; C07K 2317/569; C07K 2317/60; C07K 2317/622; C07K 2319/00; C07K 2319/30; C07K 2319/33
  See application file for complete search history.

(56) References Cited

FOREIGN PATENT DOCUMENTS

| CN | 106883297 A | 6/2017 | |
|---|---|---|---|
| CN | 107108748 A | 8/2017 | |
| CN | 107459578 A | 12/2017 | |
| CN | 107459579 A | 12/2017 | |
| WO | WO-2010070047 A1 * | 6/2010 | ......... C07K 14/4703 |
| WO | 2011076781 A1 | 6/2011 | |
| WO | 2013109752 A1 | 7/2013 | |
| WO | 2016024021 A1 | 2/2016 | |
| WO | 2017027422 A1 | 2/2017 | |

OTHER PUBLICATIONS

SHPS-1 [*Homo sapiens*], Genbank: BA12974.1, Feb. 6, 1999 (Year: 1999).*
SIRPA protein [*Homo sapiens*] GeneBank: AAH26692.1 (Year: 2006).*
Sockolosky, J.T., et al (2016) Durable antitumor responses to CD47 blockade require adaptive immune stimulation PNAS 113(19); E2646-2654 (Year: 2016).*
Lo, J., et al (2016) Anti-CD47 antibody suppresses tumour growth and augments the effect of chemotherapy treatment in hepatocellular carcinoma Liver International 36; 737-745 (Year: 2016).*
Weiskopf, K., et al (2013) Engineered SIRPα variants as immunotherapeutic adjuvants to anti-cancer antibodies Science 341(6141); 1-13. (Year: 2013).*
Weidle, U.H., et al (2013) The Intriguing Options of Multispecific Antibody Formats for Treatment of Cancer Cancer Genomics & Proteomics 10; 1-18 (Year: 2013).*
Mantovani, A., et al (2016) Tumour-associated macrophages as treatment targets in oncology Nature Reviews | Clinical Oncology 14; 399-416 (Year: 2016).*
PCT/CN2018/104303 International Search Report dated Nov. 19, 2018.
China Search Report of CN 201880057208.3 dated Jan. 7, 2022.
Yamao, T., et al., Gen Bank Accession No. BAA12974, Feb. 6, 1999, Mouse and Human SHPS-1: Molecular Cloning of cDNAs and Chromosomal Localization of Genes, Biochem. Biophys. Res. Common. 23191), 61-67, 1997, https://www.ncbi.nlm.nihgov/protein/BAA12974.1?report=genbank&log$=protalign&blast_rank=1&RID=XG787UYH013.

* cited by examiner

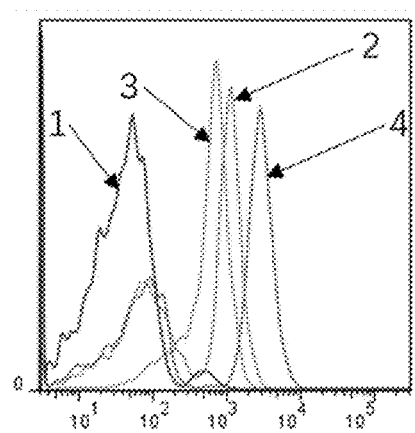
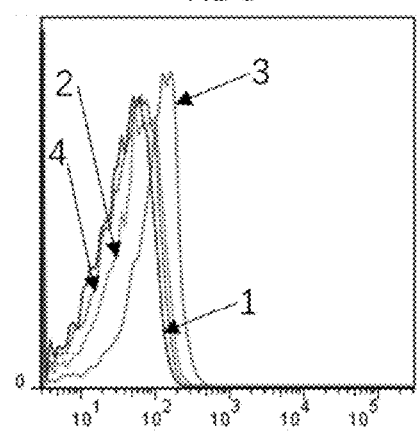
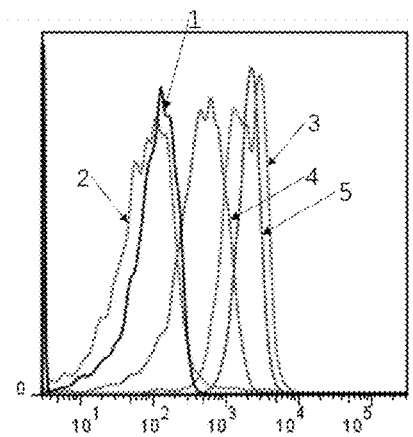
FIG. 6e
FIG. 6f

# IMMUNOCONJUGATES COMPRISING SIGNAL REGULATORY PROTEIN ALPHA

CROSS-REFERENCE TO RELATED APPLICATIONS

This application is a National Stage Application and claims priority under 35 U.S.C. § 371 to Patent Cooperation Treaty application PCT/CN2018/104303, filed Sep. 6, 2018, which claims the benefit of Patent Cooperation Treaty application PCT/CN2017/100872, filed Sep. 7, 2017. Priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2020-03-05_262790-463859_Sequence_Listing_ST25.txt," is 268,957 bytes in size and was created on Mar. 5, 2020, and filed electronically herewith.

BACKGROUND

Signal regulatory protein α (SIRPα), also known as SHPS-1, BIT, or CD172a, is an immunoglobulin superfamily protein that binds to the protein tyrosine phosphatases SHP-1 and SHP-2 through its cytoplasmic region for potential negative signaling. SIRPα is particularly abundant in the myeloid-lineage hematopoietic cells such as macrophages and dendritic cell (Reinhold et al., 1997. Costimulation of T cell activation by integrin-associated protein (CD47) is an adhesion-dependent, CD28-independent signaling pathway. *J Exp Med* 185:1-11). CD47-SIRPα interaction functions as a "don't eat me" signal to ensure that autologous cells are not inappropriately phagocytosed.

However, systematic expression of SIRPα may result in undesired side effects. Further, when expressed alone, SIRPα may have a relatively short in vivo half-life and may not be able to reach the site of action efficiently. Hence, there is a need for novel and effective regulators of the CD47-SIRPα signaling.

SUMMARY

The present disclosure provides an immunoconjugate useful in inhibiting tumor growth, and compositions and/or protein mixture comprising the immunoconjugate. The present disclosure also provides methods for the production of the immunoconjugate, as well as pharmaceutical uses of the immunoconjugate in inhibiting tumor growth, including but not limited to treatment of cancers.

In one aspect, the present disclosure provides an immunoconjugate comprising: a) a targeting moiety, wherein the targeting moiety exhibits binding specificity to a tumor associated antigen; b) an Fc domain consisting of a first Fc subunit and a second Fc subunit, wherein the first Fc subunit associates with the second Fc subunit to form a dimer; and c) a single copy of a signal-regulatory protein alpha (SIRPα).

In some embodiments, the SIRPα is not a CV1 variant.
In some embodiments, the SIRPα is a human wildtype SIRPα.

In some embodiments, said SIRPα comprises an amino acid sequence as set forth in SEQ ID NO: 122 or 123.

In some embodiments, the targeting moiety comprises an antigen-binding domain of an antibody and said antibody is selected from the group consisting of: anti-EGFRVIII, anti-HER2/neu, anti-PD-L1 and anti-Muc1.

In some embodiments, the antibody is an anti-PD-L1 antibody. For example, the anti-PD-L1 antibody may be selected from the group consisting of Atezolizumab, Avelumab, Durvalumab KN035 and hu56.

In some embodiments, the Fc domain is an IgG Fc domain. In some embodiments, the IgG is a human IgG1.

In some embodiments, the immunoconjugate is a proteinaceous heterodimer comprising a first member and a second member different from said first member, wherein said first member comprises at least one targeting moiety fused to one of the two subunits of the Fc domain, and said second member comprises said single copy of SIRPα fused to the other one of the two subunits of the Fc domain, and said first Fc subunit associates with said second Fc subunit to form said heterodimer.

In some embodiments, the targeting moiety is directly or indirectly fused to the amino-terminal amino acid of one of the two subunits of the Fc domain, and the single copy of SIRPα is directly or indirectly fused to the amino-terminal amino acid of the other one of the two subunits of the Fc domain.

In some embodiments, the immunoconjugate comprises two of the targeting moiety, which are a first targeting moiety and a second targeting moiety.

In some embodiments, the first targeting moiety is directly or indirectly fused to one of said two subunits of the Fc domain, and said second targeting moiety is directly or indirectly fused to the other one of said two subunits of the Fc domain.

In some embodiments, the immunoconjugate is a proteinaceous heterodimer. The proteinaceous heterodimer may comprise a first member and a second member different from the first member, wherein: the first member may comprise the first targeting moiety fused to one of the two subunits of the Fc domain; the second member may comprise the single copy of SIRPα, the second targeting moiety and the other one of the two subunits of the Fc domain, with the single copy of SIRPα fused to one terminal of the Fc subunit and the second targeting moiety fused to the other terminal of the Fc subunit; and the first Fc subunit associates with the second Fc subunit to form the heterodimer. For example, the first targeting moiety may be directly or indirectly fused to the amino-terminal amino acid of one of the two subunits of the Fc domain, the second targeting moiety may be directly or indirectly fused to the amino-terminal amino acid of the other one of the two subunits of the Fc domain, and the single copy of SIRPα may be directly or indirectly fused to the carboxy-terminal amino acid of the first or the second Fc subunit.

In some embodiments, the first Fc subunit is different from the second Fc subunit, and the Fc domain comprises a modification promoting heterodimerization between the first Fc subunit and the second Fc subunit. For example, the first Fc subunit may comprise a first modification, and the second Fc subunit comprises a second modification, and the first modification comprises an amino acid substitution at 2-5 positions. For example, the first modification may comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and S354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

In some embodiments, the single copy of SIRPα is directly or indirectly fused to the second Fc subunit comprising the second modification.

In one aspect, the present disclosure provides an isolated nucleic acid or isolated nucleic acids encoding the immunoconjugate of the present disclosure.

In one aspect, the present disclosure provides a vector or vectors comprising the isolated nucleic acid or isolated nucleic acids of the present disclosure.

In one aspect, the present disclosure provides an isolated host cell comprising the isolated nucleic acid or isolated nucleic acids of the present disclosure, or the vector or vectors of the present disclosure.

In one aspect, the present disclosure provides a method for producing the immunoconjugate or the protein mixture of the present disclosure. The method may comprise (i) culturing the host cell of the present disclosure under conditions to effect expression and formation of the immunoconjugate of the present disclosure, and (ii) harvesting the immunoconjugate formed or the protein mixture comprising the immunoconjugate.

In one aspect, the present disclosure provides a pharmaceutical composition comprising an effective amount of the immunoconjugate of the present disclosure, and optionally a pharmaceutically acceptable excipient.

In some embodiments, the pharmaceutical composition further comprises an effective amount of an additional therapeutically active component for cancer treatment. For example, the additional therapeutically active component for cancer treatment may be an agent for chemotherapy. In some embodiments, the agent for chemotherapy is a cytotoxic agent. For example, the cytotoxic agent may comprise doxorubicin.

In one aspect, the present disclosure provides a use of the immunoconjugate, the protein mixture, or the pharmaceutical composition of the present disclosure, in the preparation of a medicament for treating a disease in a subject in need thereof.

In one aspect, the present disclosure provides a method for treating a disease in a subject in need thereof, comprising administering to the subject an effective amount of the immunoconjugate, the protein mixture, or the pharmaceutical composition of the present disclosure.

In some embodiments, the disease is cancer. For example, the cancer may be selected from the group consisting of: breast cancer, melanoma, and colon cancer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the application are set forth with particularity in the appended claims. A better understanding of the features and advantages of the present application will be obtained by reference to the following detailed description that sets forth illustrative embodiments, in which the principles of the application are employed, and the accompanying drawings (also "figure" and "FIG." herein), of which:

FIGS. 6a-6h illustrate the binding affinity of the immunoconjugate of the present disclosure, as shown by flow cytometry results.

DETAILED DESCRIPTION

Figure 1A:
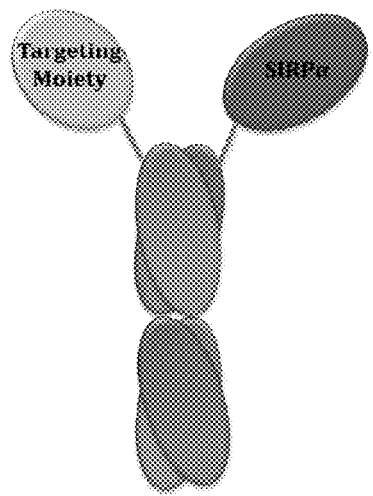
FIG. 1a-1b illustrate examples of the immunoconjugate of the present disclosure.

While various embodiments of the application have been shown and described herein, it will be obvious to those skilled in the art that such embodiments are provided by way of example only. Numerous variations, changes, and substitutions may occur to those skilled in the art without departing from the application. It should be understood that various alternatives to the embodiments of the application described herein may be employed.

The term "immunoconjugate", as used herein, generally refers to a proteinaceous molecule formed by the conjugation of one or more antibodies or a fragment thereof to one or more second molecules. The second molecule may be the same or different, and may include for example, effector proteins.

The term "targeting moiety", as used herein, generally refers to a molecule, complex or aggregate, that binds specifically, selectively or preferentially to a target molecule, cell, particle, tissue or aggregate. For example, a targeting moiety may be an antibody, antigen-binding antibody fragment, bispecific antibody or other antibody-based molecule or compound. Other examples of targeting moieties may include, but are not limited to, aptamers, avimers, receptor-binding ligands, nucleic acids, biotin-avidin binding pairs, binding peptides or proteins, etc. The terms "targeting moiety" and "binding moiety" are used interchangeably herein.

The term "binding specificity", as used herein, generally refers to an ability of one substance to bind another substance specifically, and not easily to bind any other substance at random. For example, one protein may bind to another protein specifically due to their specific structures. For example, a targeting moiety may exhibit binding specificity to a corresponding tumor associated antigen.

The term "tumor associated antigen", as used herein, generally refers to an antigenic substance related to tumor cells, which may have an ability to trigger an immune response in a host or to indicate that the host may have a tumor. For example, a tumor associated antigen may be a protein, a polypeptide, a peptide, or a fragment thereof, which constitutes part of a tumor cell and is capable of inducing tumor-specific cytotoxic T lymphocytes. A tumor associated antigen peptide may be a peptide that is generated as a result of degradation of the tumor associated antigen in a tumor cell and can induce or activate tumor-specific cytotoxic T lymphocytes upon being expressed on cell surface. In some embodiments, the term "tumor associated antigen" may also refer to biomolecules (e.g., proteins, carbohydrates, glycoproteins, etc.) that are exclusively or preferentially or differentially expressed on a cancer cell and/or are found in association with a cancer cell and thereby provide targets preferential or specific to the cancer. For example, the preferential expression can be preferential expression as compared to any other cell in the organism, or preferential expression within a particular area of the organism (e.g. within a particular organ or tissue).

The term "Fc domain", as used herein, generally refers to an Fc part or Fc fragment of an antibody heavy chain. For example, it may refer to the carboxyl terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(-CH4). CH4 is present in IgM, which has no hinge region. The immunoglobulin heavy chain constant region useful in the present disclosure may comprise an immunoglobulin hinge region, and may also include a CH3 domain. For example, the immunoglobulin heavy chain constant region may comprise an immunoglobulin hinge region, a CH2 domain and a CH3 domain. In some embodiments, the Fc region according to the present disclosure consists of the hinge-CH2-CH3 domain.

The term "Fc subunit", as used herein, generally refers to a component of an Fc domain. For example, an Fc domain may be formed by two or more members, and each member may be considered as one Fc subunit.

The term "SIRPα", as used herein, generally refers to a signal regulatory protein α or fragments thereof. SIRPα is a regulatory membrane glycoprotein from SIRP family expressed mainly by myeloid cells and also by stem cells or neurons. A SIRPα may be a human SIRPα, or functional variants thereof.

The term "CV1 variant", as used herein, generally refers to a consensus variant 1 of SIRPα. It was produced due to nine grafted conservative substitutions onto the predominant wild-type human SIRPα allele, and the CV1 variant can bind human CD 47 with an affinity of 11.1 pM (Kipp Weiskopf et al., Science. 2013 Jul. 5; 341(6141)). Hence, CV1 can competes with endogenous SIRPα for CD47 binding. However, as an Fc-free antagonist, it cannot inhibit cancer growth in vivo. It is found that the synergy between CV1 and other therapeutic mAbs is so dramatic that possibility for overestimation of CD47-SIRPα interaction remains in the presence of ADCC (Yuting Huang et al., J Thorac Dis. 2017 February; 9(2): E168-E174).

The term "single copy", as used herein, generally refers to the fact that a specific protein or element or feature is present as only one copy in a molecule, a conjugate or a complex.

The term "peptide linker", as used herein, generally refers to a synthetic amino acid sequence that connects or links two polypeptide sequences, e.g., that link two polypeptide domains. A linker may connect two amino acid sequences via peptide bonds. In some embodiments, a linker of the present disclosure connects a biologically active moiety to a second moiety in a linear sequence. The term "peptide" and "protein" are used interchangeably herein to refer to polymers of amino acids of any length. The polymer may be linear or branched, it may comprise modified amino acids, and it may be interrupted by non-amino acids. The peptide also encompasses an amino acid polymer that has been modified, for example, by disulfide bond formation, glycosylation, lipidation, acetylation, phosphorylation, or any other manipulation, such as conjugation with a labeling component. The peptide may apply to amino acid polymers in which one or more amino acid residue is an artificial chemical analogue of a corresponding naturally occurring amino acid, as well as to naturally occurring amino acid polymers. The peptide may also include variants on the traditional peptide linkage joining the amino acids making up the polypeptide. Peptides may also include essentially any poly-amino acid including, but not limited to peptide mimetics such as amino acids joined by an ether as opposed to an amide bond.

The term "amino-terminal", as used herein, generally refers to the free α-amino group on an amino acid at the amino terminal of a peptide or to the α-amino group (amino group when participating in a peptide bond) of an amino acid at any other location within the peptide.

The term "immunoglobulin hinge region", as used herein, generally refers to the hinge region of an immunoglobulin, for example, an immunoglobulin hinge region may be an IgG1 hinge, an IgG2 hinge, an IgG3 hinge or an IgG4 hinge. The term "IgG1 hinge" is used herein to refer to a hinge region from a native IgG1, such as a native human, mouse, rabbit, etc. IgG1, derivatives of one of the naturally occurring IgG1 hinges, such as derivatives that have at least 95%, 90%, 85%, 80%, 75%, 70%, or 65% amino acid identity with a native IgG1 hinge and retain essential functional characteristics of the IgG1 hinge. The term "hinge region" generally refers to the portion of a heavy chain molecule that joins the CH1 domain to the CH2 domain. This hinge region may comprise approximately 25 residues and may be flexible, thus allowing the N-terminal antigen binding regions to move independently. Hinge regions can be subdivided into three distinct domains: upper, middle, and lower hinge domains (Roux et al. J. Immunol. 1998 161:4083).

The term "immunoglobulin" as used herein, generally refers to a protein consisting of one or more polypeptides substantially encoded by immunoglobulin genes. The recognized immunoglobulin genes include the κ, λ, α, γ (IgG1, IgG2, IgG3, IgG4), δ, c ε and μ constant region genes, as well as the myriad immunoglobulin variable region genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, Fab' and (Fab')2.

The term "antigen binding domain of an antibody", as used herein, generally refers to a part of an antibody that participates in antigen binding. An antigen binding domain may be formed by amino acid residues of the N-terminal variable ("V") regions of a heavy ("H") chain and/or a light ("L") chain. Three highly divergent stretches within the V regions of the heavy and light chains are referred to as "hypervariable regions". In an antibody molecule, the three hypervariable regions of a light chain and the three hypervariable regions of a heavy chain are disposed relative to each other in three-dimensional space to form an antigen binding "surface". This surface may mediate recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4$^{th}$ ed. U.S. Dept. Health and Human Services, Public Health Services, Bethesda, Md. (1987).

The term "Fab", as used herein, generally refers to a portion (such as an antigen-binding fragment) of an immunoglobulin molecule. An Fab fragment may comprise one light chain and part of a heavy chain with a single antigen-binding site. A Fab fragment may be obtained by papain digestion of an immunoglobulin molecule. For example, a Fab fragment may be composed of one constant and one variable domain of each of the heavy and the light chain. The variable domain may contain the paratope (the antigen-binding site), comprising a set of complementarity determining regions, at the amino terminal end of the immunoglobulin molecule. The enzyme papain may be used to cleave an immunoglobulin molecule into two Fab fragments and one Fc fragment. The enzyme pepsin cleaves below the hinge region, so a F(ab')2 fragment and a Fc fragment is formed.

The term "domain antibody", as used herein, generally refers to a single domain antibody, also known as sdAb or Nanobody. A domain antibody is an antibody fragment consisting of a single monomeric variable antibody domain. Like a whole antibody, it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

The term "ScFv", as used herein, generally refers to a single-chain antibody fragment. An ScFv may refer to a recombinant single chain polypeptide molecule in which light and heavy chain variable regions of an antibody are connected by a peptide linker. Single chain antibodies (ScFv) generally do not include portions of the Fc region of antibodies that are involved in effector functions and are thus naked antibodies, although methods are known for adding such regions to known ScFv molecules if desired. See Helfrich et al., A rapid and versatile method for harnessing ScFv antibody fragments with various biological functions. J Immunol Methods 237: 131-145 (2000) and de Haard et al., Creating and engineering human antibodies for immunotherapy. Advanced Drug Delivery Reviews 31:5-31 (1998).

The term "anti-EGFR antibody", as used herein, generally refers to an antibody that specifically or preferentially binds an EGFR. In some cases, and anti-EGFR antibody may bind to a mutated form of EGFR (e.g., EGFR variant III (also known as EGFRvIII), which is the most common extracellular domain mutation of EGFR, this mutation leads to a deletion of exons 2-7 of the EGFR gene, which is characterized by a truncated extracellular domain with ligand-independent constitutive activity). For example, an anti-EGFR antibody may be Cetuximab, Mab806, or antigen binding fragments thereof.

The term "anti-HER2 antibody", as used herein, generally refers to an antibody that specifically or preferentially binds a HER2/neu receptor. For example, an anti-HER2/neu antibody or anti-HER2 antibody may be Trastuzumab, Pertuzumab, or antigen binding fragments thereof.

The term "anti-PD-L1 antibody", as used herein, generally refers to an antibody that specifically or preferentially binds to programmed death-ligand 1 (PD-L1). For example, an anti-PD-L1 antibody may be Atezolizumab, Avelumab, Durvalumab, KN035 or hu56. Atezolizumab is a humanized, engineered monoclonal antibody of IgG1 isotype against PD-L1 (from Genentech/Roche). KN035 is a PD-L1 single domain antibody Fc (IgG1 isotype) fusion protein, also named as hu56V2-Fc (as described in CN106397592A), and hu56 is a human single domain antibody against PD-L1 (as described in CN106397592A). And the position of the antibody CDRs is determined according to the antibody Kabat definition. Avelumab is a fully human monoclonal antibody developed by Merck KGaA and Pfizer as a pharmaceutical drug for use in immunotherapy, originally for the treatment of non-small-cell lung carcinoma, and targets the protein PD-L1. Durvalumab is a human immunoglobulin G1 kappa (IgG1K) monoclonal antibody that blocks the interaction of PD-L1 and PD1 (from Medimmune/AstraZeneca).

The term "IgG", as used herein, generally refers to a subtype of an antibody. Each IgG has two antigen binding sites. Representing approximately 75% of serum antibodies in humans, IgG is the most common type of antibody found in the circulation. Some of the known immunoglobulin genes include the κ, λ, α, and γ (IgG1, IgG2, IgG3, and IgG4).

The term "in frame", as used herein, generally refers to the joining of two or more open reading frames (ORFs) to form a continuous longer ORF, in a manner that maintains the correct reading frame of each original ORF.

The term "proteinaceous", as used herein, generally refers to a material or molecule that is of, relating to, resembling, or being a polypeptide or a protein. For example, a proteinaceous heterodimer of the present disclosure may be a heterodimer protein, or a heterodimer comprising two or more polypeptides.

The term "heterodimer", as used herein, generally refers to a molecule (e.g. a proteinaceous molecule) composed of two different members (i.e., two different monomers). The two members of a heterodimer may differ in structure, function, activity and/or composition. For example, the two different members may comprise polypeptides differing in the order, number, or kind of amino acid residues forming these polypeptides. Each of the two different members of a heterodimer may independently comprise one, two or more units, polypeptide chains, or moieties. The two members may aggregate, complex or associate with each other via covalent and/or non-covalent interactions. For example, the two different monomers may associate with each other via interactions between interface amino acid residues from each of the two monomers The term "modification promoting heterodimerization", as used herein, generally refers to a modification which promotes the process of heterodimerization. And the term heterodimerization as used herein, generally refers to the process of forming a heterodimer between two different members (e.g., two different polypeptides), such as through complexation, association, or aggregation, with or without formation of covalent bonds between the two different members.

The term "anti-CD47 monoclonal antibody", as used herein, generally refers to a monoclonal antibody that specifically or preferentially binds to CD47. For example, an anti-CD47 monoclonal antibody may be AB6.12 IgG1. In another example, an anti-CD47 monoclonal antibody may be B6H12.2.

The term "protein mixture", as used herein, generally refers to a mixture of two or more types of proteins.

The term "homodimer", as used herein, generally refers to a molecule formed by two identical monomers (e.g., two identical members or subunits). The two monomers may aggregate, complex or associate with each other via covalent and/or non-covalent interactions. For example, the two identical monomers may associate with each other via interactions between interface amino acid residues from each of the two monomers.

The term "about", as used herein, generally refers to an approximation to a given value that would reasonably be inferred based on the ordinary skill in the art, including equivalents and approximations due to the experimental and/or measurement conditions for such given value. For example, it may refer to a value that is no more than 10% above or below the value being modified by the term. For example, the term "about 5 µg/kg" means a range of 4.5 µg/kg to 5.5 µg/kg. As another example, "about 1 hour" means a range of 48 minutes to 72 minutes.

The term "substantially comprise no", as used herein, generally refers to that a composition (e.g., a mixture) comprises little or almost none of a specific substance. For example, the specific substance may be present with a percentage of e.g., less than 10%, less than 9%, less than 8%, less than 7%, less than 6%, less than 5%, less than 4%, less than 3%, less than 2%, less than 1%, less than 0.5%, less than 0.1%, or less than 0.01%.

The term "conditions to effect expression", as used herein, generally refers to conditions influencing the expression of the immunoconjugate of the present application. In some embodiments, the conditions to effect expression include but not limited to incubation time, temperature, and culture medium, and may depend on cell type and may be readily determined by one of ordinary skill in the art. In some embodiments, during the process of producing the immunoconjugate or the protein mixture of the present disclosure, the host cells are grown in cultures, and in any apparatus that may be used to grow cultures, including fermenters. Cells may be grown as monolayers or attached to a surface. Alternatively, the host cells may be grown in suspension. The cells can be grown in a culture medium that is serum-free. The media can be a commercially available media, such as, but not limited to, Opti-CHO (Invitrogen, Catalogue #12681) supplemented with glutamine, such as 8 mM L-glutamine; RPMI 1640 medium, supplemented with 10% bovine calf serum, 10.5 ng/ml mIL-3 and L-glutamine; or 5% FCS medium.

The term "pharmaceutically acceptable excipient", as used herein, generally refers to any and all solvents, dispersion media, coatings, isotonic and absorption delaying agents, etc., that are compatible with pharmaceutical administration.

The term "therapeutically active component for cancer treatment", as used herein, generally refers to any component that has therapeutic activity for the treatment of cancer. For example, a therapeutically active component for cancer treatment may be an agent for chemotherapy.

The term "agent for chemotherapy", as used herein, generally refers to agents used in a chemotherapy for cancer treatment. For example, the agent for chemotherapy may include but not limited to a cytotoxic agent, an alkylating agent, an antimetabolite agent, an anti-tumor antibiotic agent, and an anti-tumor hormone.

The term "cytotoxic agent", as used herein, generally refers to an agent that has cytotoxicity. For example, a cytotoxic agent may comprise doxorubicin.

The term "effective amount", as used herein, generally refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific component, the route of administration, the rate of clearance, the duration of treatment, the age, body weight, sex, diet, and general health of the subject, and other related factors.

The term "complexed with" as used herein, generally refers to the association (e.g., binding) of one member/subunit with another member/subunit of a molecule (e.g., an antibody). For example, a light chain may be complexed with a heavy chain to form a targeting moiety. In another example, a first Fc subunit may be complexed with a second Fc subunit to form an Fc dimer (an Fc region).

The term "binding specificity" as used herein, generally refers to the ability to specifically bind (e.g., immunoreact with) a given target (while not binding or substantially not binding a non-target). A targeting moiety of the present disclosure may be monospecific and contain one or more binding sites which specifically bind a target or may be multispecific (e.g., bispecific or trispecific) and contain two or more binding sites which specifically bind the same or different targets.

The term "modification" as used herein, generally refers to any manipulation of the peptide backbone (e.g. amino acid sequence) or any post-translational modifications (e.g. glycosylation) of a polypeptide. For example, a modification is in comparison to the sequence of a corresponding wildtype polypeptide. A modification may be a substitution, an addition, and/or a deletion of one or more amino acids (e.g., 1, 2, 3, 4, 5, 6, 7, 8, 9, 10, or more).

The term "fusion protein" as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide unrelated to the former polypeptide or the domain thereof).

The term "C-terminus" as used herein, generally refers to the carboxy terminus of a polypeptide.

The term "N-terminus" as used herein, generally refers to the amino terminus of a polypeptide.

The term "EGFR" as used herein, generally refers to epidermal growth factor receptor. for example, see in Carpenter et al. Ann. Rev. Biochem. 56:881-914 (1987), including naturally occurring mutant forms thereof.

The term "EGFR mutant" as used herein, generally refers to a mutated form of EGFR (e.g., EGFR variant III (also known as EGFRvIII), which is the most common extracellular domain mutation of EGFR, this mutation leads to a deletion of exons 2-7 of the EGFR gene which is characterized by a truncated extracellular domain with ligand-independent constitutive activity.

The term "HER2/neu" as used herein, generally refers to a human HER2 protein, for example, in Semba et al., PNAS (USA) 82:6497-6501 (1985) and Yamamoto et al. Nature 319:230-234 (1986) (GenBank accession number X03363).

The term "Muc1" as used herein, generally refers to a glycoprotein encoded by the muc1 gene. Muc1 is mainly present in the epithelial tissues and organs of mammary gland, pancreas, ovary, etc. It is highly expressed on the surface of cancer epithelial cells, and accordingly becomes the target of immune response.

The term "amino acid substitution" as used herein, generally refers to that one amino acid at a specific position of a polypeptide is replaced by another amino acid.

The term "EU index of the KABAT number" as used herein, generally refers to the index of the EU number corresponding to the amino acid sequence according to Kabat et al. (1971) Ann. NY Acad, Sci. 190:382-391 and Kabat, E. A., et al. (1991) Sequences of Proteins of Immunological Interest, Fifth Edition, U.S. Department of Health and Human Services, NIH Publication No. 91-3242.

The term "isolated polynucleotide" as used herein, generally refers to a polymeric form of nucleotides of any length, either deoxyribonucleotides or ribonucleotides, or analogs thereof, isolated from its native environment, or that is artificially synthesized.

Immunoconjugate, Protein Mixtures, Isolated Nucleotides, Vectors and Host Cells

In one aspect, the present disclosure provides an immunoconjugate comprising: a) a targeting moiety, wherein the targeting moiety exhibits binding specificity to a tumor associated antigen; b) an Fc domain consisting of a first Fc subunit and a second Fc subunit, wherein the first Fc subunit associates with the second Fc subunit to form a dimer; and c) a single copy of a signal-regulatory protein alpha (SIRPα).

The single copy of SIRPα may be directly or indirectly fused to an amino-terminal or carboxy-terminal amino acid of the first Fc subunit or the second Fc subunit of the Fc domain. For example, the single copy of SIRPα may be indirectly fused to the first Fc subunit or the second Fc subunit of the Fc domain through a peptide linker. The linker may be a peptide comprising 1, 2, 3, 4, 5, 6, 7, 8, 9, 10, 11, 12, 13, 14, 15, 16, 17, 18, 19, 20, 21, 22, 23, 24, 25 or more amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. In some embodiments, the linker comprises an amino acid sequence as set forth in SEQ ID NO: 53, 58, 65, 68 or 71.

For example, the single copy of SIRPα may be fused to the first Fc subunit or the second Fc subunit of the Fc domain in frame.

The SIRPα may be a wild-type signal-regulatory protein alpha or an amino acid sequence of a recombinant or non-recombinant polypeptide having the amino acid sequence of wild-type signal-regulatory protein alpha or a native or naturally occurring allelic variant of signal-regulatory protein alpha. In some embodiments, the SIRPα is a wild-type mammalian SIRPα, for example, the SIRPα is a wild-type human SIRPα. The amino acid sequence for the mature form of the predominant wild type human SIRPα (SIRPαV2) without a signal peptide may be as set forth in SEQ ID NO: 122. The SIRPα may include a signal peptide. For example, the amino acid sequence of the human SIRPα (SIRPαV2) with a signal peptide may be as set forth in SEQ ID NO: 123.

The targeting moiety may be directly or indirectly fused to an amino-terminal or carboxy-terminal amino acid of the first Fc subunit and/or the second Fc subunit of the Fc domain. For example, the targeting moiety may be indirectly fused to the first Fc subunit and/or the second Fc subunit of the Fc domain through a peptide linker or an immunoglobulin hinge region. The linker may be a peptide comprising 1, 2, 3, 4, 5, 6, 7, 8, 9, 10, 11, 12, 13, 14, 15, 16, 17, 18, 19, 20, 21, 22, 23, 24, 25 or more amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. For example, the linker may comprise an amino acid sequence as set forth in SEQ ID NO: 53, 58, 65, 68 or 71.

The targeting moiety may comprise an antigen binding domain of an antibody. For example, the antigen binding domain of an antibody may be a Fab moiety, a domain antibody or a ScFv moiety.

The tumor associated antigen may be selected from the group consisting of: EGFRVIII, HER2/neu, PD-L1, and Muc1. For example, the targeting moiety may comprise an antigen-binding domain of an antibody and the antibody may be selected from the group consisting of: anti-EGFRVIII, anti-HER2/neu, anti-PD-L1 and anti-Muc1 antibody.

The antibody may be an anti-EGFRVIII antibody. For example, the anti-EGFRVIII antibody may be Mab 806. The targeting moiety may comprise the heavy chain CDR1-3 of Mab 806, the light chain CDR1-3 of Mab 806, the heavy chain variable region of Mab 806, the light chain variable region of Mab 806, and/or the light chain of Mab 806. For example, the targeting moiety may be a Fab moiety comprising both the heavy chain variable region and the light chain variable region (or the light chain) of Mab 806. In another example, the targeting moiety may be a domain antibody (e.g., a $V_H H$) comprising the heavy chain variable region of Mab 806. In another example, the targeting moiety may be an ScFv moiety comprising the heavy chain variable region and the light chain variable region of Mab 806.

For example, the targeting moiety may comprise heavy chain CDRs having an amino acid sequence that is at least 60%, 70%, 75%, 80%, 85%, 90%, 95%, 96%, 97%, 98%, 99% or 100% identical to that comprised in the corresponding heavy chain CDR1-3 of Mab 806. Alternatively or additionally, the targeting moiety may comprise light chain CDRs having an amino acid sequence that is at least 60%, 70%, 75%, 80%, 85%, 90%, 95%, 96%, 97%, 98%, 99% or 100% identical to that comprised in the corresponding light chain CDR1-3 of Mab 806. For example, the targeting moiety may comprise a heavy chain variable region having an amino acid sequence that is at least 60%, 70%, 75%, 80%, 85%, 90%, 95%, 96%, 97%, 98%, 99% or 100% identical to that comprised in the corresponding heavy chain variable region of Mab 806. For example, the targeting moiety may comprise a light chain variable region having an amino acid sequence that is at least 60%, 70%, 75%, 80%, 85%, 90%, 95%, 96%, 97%, 98%, 99% or 100% identical to that comprised in the corresponding light chain variable region of Mab 806. For example, the targeting moiety may comprise a light chain having an amino acid sequence that is at least 60%, 70%, 75%, 80%, 85%, 90%, 95%, 96%, 97%, 98%, 99% or 100% identical to that comprised in the corresponding light chain of Mab 806.

The heavy chain CDR 1-3 of Mab 806 are as set forth in SEQ ID NO: 90 (CDR1), SEQ ID NO: 91 (CDR2), and SEQ ID NO: 92 (CDR3), respectively. The light chain CDR 1-3 of Mab 806 are as set forth in SEQ ID NO: 86 (CDR1), SEQ ID NO: 87 (CDR2), and SEQ ID NO: 88 (CDR3), respectively. The heavy chain variable region of Mab 806 is as set forth in SEQ ID NO: 93. The light chain variable region of Mab 806 is as set forth in SEQ ID NO: 89.

The antibody may be an anti-HER2 antibody. For example, the anti-HER2 antibody may be Pertuzumab. The targeting moiety may comprise the heavy chain CDR1-3 of Pertuzumab, the light chain CDR1-3 of Pertuzumab, the heavy chain variable region of Pertuzumab, the light chain variable region of Pertuzumab, and/or the light chain of Pertuzumab. For example, the targeting moiety may be a Fab moiety comprising both the heavy chain variable region and the light chain variable region (or the light chain) of Pertuzumab. In another example, the targeting moiety may be a domain antibody (e.g., a $V_HH$) comprising the heavy chain variable region of Pertuzumab. In another example, the targeting moiety may be an ScFv moiety comprising the heavy chain variable region and the light chain variable region of Pertuzumab.

For example, the targeting moiety may comprise heavy chain CDRs having an amino acid sequence that is at least 60%, 70%, 75%, 80%, 85%, 90%, 95%, 96%, 97%, 98%, 99% or 100% identical to that comprised in the corresponding heavy chain CDR1-3 of Pertuzumab. For example, alternatively or additionally, the targeting moiety may comprise light chain CDRs having an amino acid sequence that is at least 60%, 70%, 75%, 80%, 85%, 90%, 95%, 96%, 97%, 98%, 99% or 100% identical to that comprised in the corresponding light chain CDR1-3 of Pertuzumab. For example, the targeting moiety may comprise a heavy chain variable region having an amino acid sequence that is at least 60%, 70%, 75%, 80%, 85%, 90%, 95%, 96%, 97%, 98%, 99% or 100% identical to that comprised in the corresponding heavy chain variable region of Pertuzumab. For example, the targeting moiety may comprise a light chain variable region having an amino acid sequence that is at least 60%, 70%, 75%, 80%, 85%, 90%, 95%, 96%, 97%, 98%, 99% or 100% identical to that comprised in the corresponding light chain variable region of Pertuzumab. For example, the targeting moiety may comprise a light chain having an amino acid sequence that is at least 60%, 70%, 75%, 80%, 85%, 90%, 95%, 96%, 97%, 98%, 99% or 100% identical to that comprised in the corresponding light chain of Pertuzumab.

The heavy chain CDR 1-3 of Pertuzumab are as set forth in SEQ ID NO: 106 (CDR1), SEQ ID NO: 107 (CDR2), and SEQ ID NO: 108 (CDR3), respectively. The light chain CDR 1-3 of Pertuzumab are as set forth in SEQ ID NO: 102 (CDR1), SEQ ID NO: 103 (CDR2), and SEQ ID NO: 104 (CDR3), respectively. The heavy chain variable region of Pertuzumab is as set forth in SEQ ID NO: 109. The light chain variable region of Pertuzumab is as set forth in SEQ ID NO: 105.

In some embodiments, the anti-HER2 antibody is Trastuzumab. The targeting moiety may comprise the heavy chain CDR1-3 of Trastuzumab, the light chain CDR1-3 of Trastuzumab, the heavy chain variable region of Trastuzumab, the light chain variable region of Trastuzumab, and/or the light chain of Trastuzumab. For example, the targeting moiety may be a Fab moiety comprising both the heavy chain variable region and the light chain variable region (or the light chain) of Trastuzumab. In another example, the targeting moiety may be a domain antibody (e.g., a $V_HH$) comprising the heavy chain variable region of Trastuzumab. In another example, the targeting moiety may be an ScFv moiety comprising the heavy chain variable region and the light chain variable region of Trastuzumab.

For example, the targeting moiety may comprise heavy chain CDRs having an amino acid sequence that is at least 60%, 70%, 75%, 80%, 85%, 90%, 95%, 96%, 97%, 98%, 99% or 100% identical to that comprised in the corresponding heavy chain CDR1-3 of Trastuzumab. Alternatively or additionally, the targeting moiety may comprise light chain CDRs having an amino acid sequence that is at least 60%, 70%, 75%, 80%, 85%, 90%, 95%, 96%, 97%, 98%, 99% or 100% identical to that comprised in the corresponding light chain CDR1-3 of Trastuzumab. For example, the targeting moiety may comprise a heavy chain variable region having an amino acid sequence that is at least 60%, 70%, 75%, 80%, 85%, 90%, 95%, 96%, 97%, 98%, 99% or 100% identical to that comprised in the corresponding heavy chain variable region of Trastuzumab. For example, the targeting moiety may comprise a light chain variable region having an amino acid sequence that is at least 60%, 70%, 75%, 80%, 85%, 90%, 95%, 96%, 97%, 98%, 99% or 100% identical to that comprised in the corresponding light chain variable region of Trastuzumab. For example, the targeting moiety may comprise a light chain having an amino acid sequence that is at least 60%, 70%, 75%, 80%, 85%, 90%, 95%, 96%, 97%, 98%, 99% or 100% identical to that comprised in the corresponding light chain of Trastuzumab.

The heavy chain CDR 1-3 of Trastuzumab are as set forth in SEQ ID NO: 98 (CDR1), SEQ ID NO: 99 (CDR2), and SEQ ID NO: 100 (CDR3), respectively. The light chain CDR 1-3 of Trastuzumab are as set forth in SEQ ID NO: 94 (CDR1), SEQ ID NO: 95 (CDR2), and SEQ ID NO: 96 (CDR3), respectively. The heavy chain variable region of Trastuzumab is as set forth in SEQ ID NO: 101. The light chain variable region of Trastuzumab is as set forth in SEQ ID NO: 97.

The antibody may be an anti-Muc1 antibody. For example, the anti-Muc1 antibody may be 5E5 or a humanized version thereof. The targeting moiety may comprise the heavy chain CDR1-3 of 5E5 or a humanized version thereof, the light chain CDR1-3 of 5E5 or a humanized version thereof, the heavy chain variable region of 5E5 or a humanized version thereof, the light chain variable region of 5E5 or a humanized version thereof, and/or the light chain of 5E5 or a humanized version thereof. For example, the targeting moiety may be a Fab moiety comprising both the heavy chain variable region and the light chain variable region (or the light chain) of 5E5 or a humanized version thereof. In another example, the targeting moiety may be a domain antibody (e.g., a $V_HH$) comprising the heavy chain variable region of 5E5 or a humanized version thereof. In another example, the targeting moiety may be an ScFv moiety comprising the heavy chain variable region and the light chain variable region of 5E5 or a humanized version thereof.

For example, the targeting moiety may comprise heavy chain CDRs having an amino acid sequence that is at least 60%, 70%, 75%, 80%, 85%, 90%, 95%, 96%, 97%, 98%, 99% or 100% identical to that comprised in the corresponding heavy chain CDR1-3 of 5E5 or a humanized version thereof. Alternatively or additionally, the targeting moiety may comprise light chain CDRs having an amino acid sequence that is at least 60%, 70%, 75%, 80%, 85%, 90%, 95%, 96%, 97%, 98%, 99% or 100% identical to that comprised in the corresponding light chain CDR1-3 of 5E5 or a humanized version thereof. For example, the targeting moiety may comprise a heavy chain variable region having an amino acid sequence that is at least 60%, 70%, 75%, 80%, 85%, 90%, 95%, 96%, 97%, 98%, 99% or 100% identical to that comprised in the corresponding heavy chain variable region of 5E5 or a humanized version thereof. For example, the targeting moiety may comprise a light chain variable region having an amino acid sequence that is at least 60%, 70%, 75%, 80%, 85%, 90%, 95%, 96%, 97%, 98%, 99% or 100% identical to that comprised in the corresponding light chain variable region of 5E5 or a humanized version thereof. For example, the targeting moiety may comprise a light chain having an amino acid sequence that is at least 60%, 70%, 75%, 80%, 85%, 90%, 95%, 96%, 97%, 98%, 99% or 100% identical to that comprised in the corresponding light chain of 5E5 or a humanized version thereof.

The heavy chain CDR 1-3 of 5E5 are as set forth in SEQ ID NO: 114 (CDR1), SEQ ID NO: 115 (CDR2), and SEQ ID NO: 116 (CDR3), respectively. The light chain CDR 1-3 of 5E5 are as set forth in SEQ ID NO: 110 (CDR1), SEQ ID NO: 111 (CDR2), and SEQ ID NO: 112 (CDR3), respectively. The heavy chain variable region of 5E5 is as set forth in SEQ ID NO: 117. The light chain variable region of 5E5 is as set forth in SEQ ID NO: 113.

The antibody may be an anti-PD-L1 antibody. For example, the anti-PD-L1 antibody may be selected from the group consisting of Atezolizumab, Avelumab, Durvalumab, KN035 and hu56. The targeting moiety may comprise the heavy chain CDR1-3 of Atezolizumab, Avelumab, Durvalumab, KN035 and hu56, the light chain CDR1-3 of Atezolizumab, Avelumab and Durvalumab, the heavy chain variable region of Atezolizumab, Avelumab, Durvalumab, KN035 and hu56, the light chain variable region of Atezolizumab, Avelumab and Durvalumab, and/or the light chain of Atezolizumab, Avelumab and Durvalumab. For example, the targeting moiety may be a Fab moiety comprising both the heavy chain variable region and the light chain variable region (or the light chain) of Atezolizumab, Avelumab and Durvalumab. In another example, the targeting moiety may be a domain antibody (e.g., a $V_HH$) comprising the heavy chain variable region of Atezolizumab, Avelumab, Durvalumab, KN035 and hu56. In another example, the targeting moiety may be an ScFv moiety comprising the heavy chain variable region and the light chain variable region of Atezolizumab, Avelumab and Durvalumab.

For example, the anti-PD-L1 antibody may be selected from the group consisting of Atezolizumab, Avelumab, Durvalumab, KN035 and hu56. For example, the targeting moiety may comprise heavy chain CDR 1-3 having an amino acid sequence that is at least 60%, 70%, 75%, 80%, 85%, 90%, 95%, 96%, 97%, 98%, 99% or 100% identical to that comprised in the corresponding heavy chain CDR1-3 of Atezolizumab, Avelumab, Durvalumab, KN035 and hu56. Alternatively or additionally, the targeting moiety may comprise light chain CDR 1-3 having an amino acid sequence that is at least 60%, 70%, 75%, 80%, 85%, 90%, 95%, 96%, 97%, 98%, 99% or 100% identical to that comprised in the corresponding light chain CDR1-3 of Atezolizumab, Avelumab and Durvalumab. For example, the targeting moiety may comprise a heavy chain variable region having an amino acid sequence that is at least 60%, 70%, 75%, 80%, 85%, 90%, 95%, 96%, 97%, 98%, 99% or 100% identical to that comprised in the corresponding heavy chain variable region of Atezolizumab, Avelumab, Durvalumab, KN035 and hu56. For example, the targeting moiety may comprise a light chain variable region having an amino acid sequence that is at least 60%, 70%, 75%, 80%, 85%, 90%, 95%, 96%, 97%, 98%, 99% or 100% identical to that comprised in the corresponding light chain variable region of Atezolizumab, Avelumab and Durvalumab. For example, the targeting moiety may comprise a light chain having an amino acid sequence that is at least 60%, 70%, 75%, 80%, 85%, 90%, 95%, 96%, 97%, 98%, 99% or 100% identical to that comprised in the corresponding light chain of Atezolizumab, Avelumab and Durvalumab.

The heavy chain CDR 1-3 of hu56 are as set forth in SEQ ID NO: 118 (CDR1), SEQ ID NO: 119 (CDR2), and SEQ ID NO: 120 (CDR3), respectively. The heavy chain variable region of hu56 is as set forth in SEQ ID NO: 121.

The heavy chain CDR 1-3 of KN035 are as set forth in SEQ ID NO: 118 (CDR1), SEQ ID NO: 119 (CDR2), and SEQ ID NO: 120 (CDR3), respectively. The heavy chain variable region of hu56 is as set forth in SEQ ID NO: 121.

The heavy chain CDR 1-3 of Atezolizumab are as set forth in SEQ ID NO: 128 (CDR1), SEQ ID NO: 129 (CDR2), and SEQ ID NO: 130 (CDR3), respectively. The light chain CDR 1-3 of Atezolizumab are as set forth in SEQ ID NO: 124 (CDR1), SEQ ID NO: 125 (CDR2), and SEQ ID NO: 126 (CDR3), respectively. The heavy chain variable region of Atezolizumab is as set forth in SEQ ID NO: 131. The light chain variable region of Atezolizumab is as set forth in SEQ ID NO: 127.

The heavy chain CDR 1-3 of Avelumab are as set forth in SEQ ID NO: 136 (CDR1), SEQ ID NO: 137 (CDR2), and SEQ ID NO: 138 (CDR3), respectively. The light chain CDR 1-3 of Avelumab are as set forth in SEQ ID NO: 132 (CDR1), SEQ ID NO: 133 (CDR2), and SEQ ID NO: 134 (CDR3), respectively. The heavy chain variable region of Avelumab is as set forth in SEQ ID NO: 139. The light chain variable region of Avelumab is as set forth in SEQ ID NO: 135.

The heavy chain CDR 1-3 of Durvalumab are as set forth in SEQ ID NO: 144 (CDR1), SEQ ID NO: 145 (CDR2), and SEQ ID NO: 146 (CDR3), respectively. The light chain CDR 1-3 of Durvalumab are as set forth in SEQ ID NO: 140 (CDR1), SEQ ID NO: 141 (CDR2), and SEQ ID NO: 142 (CDR3), respectively. The heavy chain variable region of Durvalumab is as set forth in SEQ ID NO: 147. The light chain variable region of Durvalumab is as set forth in SEQ ID NO: 143.

In the immunoconjugate of the present disclosure, the Fc domain may be an IgG Fc domain. For example, the IgG may be selected from the group consisting of IgG1, IgG2, IgG3 and IgG4. In some embodiments, the IgG is a human IgG1, and the Fc domain is a human IgG1 Fc domain (wildtype or modified).

In the immunoconjugate of the present disclosure, first Fc subunit of the Fc domain may be different from the second Fc subunit, and the Fc domain may comprise a modification promoting heterodimerization between the first Fc subunit and the second Fc subunit. For example, the first Fc subunit may comprise a first modification, and the second Fc subunit comprises a second modification.

The first modification may comprise an amino acid substitution at position T366, and an amino acid substitution at one or more positions selected from the group consisting of: Y349, F405, K409, D399, K360, Q347, K392 and S354, wherein the position of the amino acid is determined according to the EU index of the KABAT number. For example, the amino acid substitution comprised by the first modification may be selected from the group consisting of Y349C, Y349D, D399S, F405K, K360E, K409A, K409E, Q347E, Q347R, S354D, K392D and T366W.

The first modification may comprise an amino acid substitution at 2-7 positions (e.g., 2-6, 2-5, 2-4, 2-3, or 2 positions). For example, the first modification may comprise an amino acid substitution at a group of positions selected from any of the following groups: 1) Y349 and T366; 2) Y349, T366 and F405; 3) Y349, T366 and K409; 4) Y349, T366, F405, K360 and Q347; 5) Y349, T366, F405 and Q347; 6) Y349, T366, K409, K360 and Q347; 7) Y349, T366, K409 and Q347; 8) T366, K409 and K392; 9) T366 and K409; 10) T366, K409, Y349 and S354; 11) T366 and F405; 12) T366, F405 and D399; and 13) T366, F405, Y349 and S354. For example, the first modification may comprise a group of amino acid substitutions selected from any of the following groups: 1) Y349C and T366W; 2) Y349C, T366W and F405K; 3) Y349C, T366W and K409E; 4) Y349C, T366W and K409A; 5) Y349C, T366W, F405K, K360E and Q347E; 6) Y349C, T366W, F405K and Q347R; 7) Y349C, T366W, K409A, K360E and Q347E; 8) Y349C, T366W, K409A and Q347R; 9) T366W, K409A and K392D; 10) T366W and K409A; 11) T366W, K409A and Y349D; 12) T366W, K409A, Y349D and S354D; 13) T366W and F405K; 14) T366W, F405K and D399S; 15) T366W, F405K and Y349D; and 16) T366W, F405K, Y349D and S354D.

The second modification may comprise amino acid substitutions at positions T366, L368 and Y407, as well as an amino acid substitution at one or more positions selected from the group consisting of D356, D399, E357, F405, K360, K392, K409 and Q347, wherein the position of the amino acid is determined according to the EU index of the KABAT number. For example, the amino acid substitution comprised by the second modification may be selected from the group consisting of D356C, D399S, E357A, F405K, K360E, K392D, K409A, L368A, L368G, Q347E, Q347R, T366S, Y407A and Y407V.

The second modification may comprise an amino acid substitution at 4-8 positions (e.g., 4-7, 4-6, 4-5, or 4 positions). For example, the second modification may comprise an amino acid substitution at a group of positions selected from any of the following groups: 1) D356, T366, L368, Y407 and F405; 2) D356, T366, L368 and Y407; 3) D356, T366, L368, Y407 and Q347; 4) D356, T366, L368, Y407, K360 and Q347; 5) D356, T366, L368, Y407, F405 and Q347; 6) D356, T366, L368, Y407, F405, K360 and Q347; 7) T366, L368, Y407, D399 and F405; 8) T366, L368, Y407 and F405; 9) T366, L368, Y407, F405 and E357; 10) T366, L368, Y407 and K409; 11) T366, L368, Y407, K409 and K392; and 12) T366, L368, Y407, K409 and E357. For example, the second modification may comprise a group of amino acid substitutions selected from any of the following groups: 1) D356C, T366S, L368A, Y407V and F405K; 2) D356C, T366S, L368A and Y407V; 3) D356C, T366S, L368A, Y407V and Q347R; 4) D356C, T366S, L368A, Y407V, K360E and Q347E; 5) D356C, T366S, L368A, Y407V, F405K and Q347R; 6) D356C, T366S, L368A, Y407V, F405K, K360E and Q347E; 7) T366S, L368A, Y407V, D399S and F405K; 8) T366S, L368G, Y407A and F405K; 9) T366S, L368A, Y407V, F405K and E357A; 10) T366S, L368A, Y407V and K409A; 11) T366S, L368A, Y407V, K409A and K392D; 12) T366S, L368G, Y407A and K409A; 13) T366S, L368A, Y407V, K409A and E357A.

For example, the first Fc subunit may comprise the first modification, the second Fc subunit may comprise the second modification, the first modification and the second modification may comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and S354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

For example, the first Fc subunit may comprise the first modification, the second Fc subunit may comprise the second modification, wherein the first modification and the second modification may comprise a group of amino acid substitutions selected from any of the following groups: 1) the first modification: Y349C and T366W; and the second modification: D356C, T366S, L368A, Y407V and F405K; 2) the first modification: Y349C, T366W and F405K; and the second modification: D356C, T366S, L368A and Y407V; 3) the first modification: Y349C, T366W and K409E; and the second modification: D356C, T366S, L368A, Y407V and F405K; 4) the first modification: Y349C, T366W and K409A; and the second modification: D356C, T366S, L368A, Y407V and F405K; 5) the first modification: Y349C, T366W, F405K, K360E and Q347E;

and the second modification: D356C, T366S, L368A, Y407V and Q347R; 6) the first modification: Y349C, T366W, F405K and Q347R; and the second modification: D356C, T366S, L368A, Y407V, K360E and Q347E; 7) the first modification: Y349C, T366W, K409A, K360E and Q347E; and the second modification: D356C, T366S, L368A, Y407V, F405K and Q347R; 8) the first modification: Y349C, T366W, K409A and Q347R; and the second modification: D356C, T366S, L368A, Y407V, F405K, K360E and Q347E; 9) the first modification: T366W, K409A and K392D; and the second modification: T366S, L368A, Y407V, D399S and F405K; 10) the first modification: T366W and K409A; and the second modification: T366S, L368G, Y407A and F405K; 11) the first modification: T366W, K409A and Y349D; and the second modification: T366S, L368A, Y407V, F405K and E357A; 12) the first modification: T366W, K409A, Y349D and S354D; and the second modification: T366S, L368A, Y407V, F405K and E357A; 13) the first modification: T366W and F405K; and the second modification: T366S, L368A, Y407V and K409A; 14) the first modification: T366W, F405K and D399S; and the second modification: T366S, L368A, Y407V, K409A and K392D; 15) the first modification: T366W and F405K; and the second modification: T366S, L368G, Y407A and K409A; 16) the first modification: T366W, F405K and Y349D; and the second modification: T366S, L368A, Y407V, K409A and E357A; 17) the first modification: T366W, F405K, Y349D and S354D; and the second modification: T366S, L368A, Y407V, K409A and E357A; wherein the position of the amino acid is determined according to the EU index of the KABAT number.

In some embodiments, the first Fc subunit comprises the first modification, the second Fc subunit comprises the second modification, the first modification comprises the amino acid substitutions T366W and K409A, and the second modification comprises the amino acid substitutions T366S, L368G, Y407A and F405K, wherein the position of the amino acid is determined according to the EU index of the KABAT number.

In some embodiments, the single copy of SIRPα is directly or indirectly fused to the second Fc subunit comprising the second modification.

The amino acid sequence of the first Fc subunit may be selected from SEQ ID NO: 39, 43, 47, 51, 54, 56, 59, 76, 80 or 84.

The amino acid sequence of the second Fc subunit may be selected from SEQ ID NO: 66 or 72.

The immunoconjugate may comprise one or more of said targeting moieties.

In some embodiments, the immunoconjugate comprises only one targeting moiety. In some embodiments, the immunoconjugate comprises two or more targeting moieties.

For example, the immunoconjugate may be a proteinaceous heterodimer comprising a first member and a second member different from the first member. The first member may comprise the targeting moiety fused to one of the two subunits of the Fc domain, and the second member may comprise the single copy of SIRPα fused to the other one of the two subunits of the Fc domain. The first Fc subunit may associate with the second Fc subunit to form the heterodimer.

For example, the targeting moiety may be directly or indirectly (e.g., via said linker) fused to the amino-terminal amino acid of one of the two subunits of the Fc domain, and the single copy of SIRPα may be directly or indirectly (e.g., via said linker) fused to the amino-terminal amino acid of the other one of the two subunits of the Fc domain.

In some embodiments, the immunoconjugate comprises two of the targeting moiety, which are a first targeting moiety and a second targeting moiety. The first targeting moiety and the second targeting moiety may exhibit binding specificity to different tumor associated antigens or to the same tumor associated antigen. For example, the first targeting moiety and the second targeting moiety may exhibit binding specificity to the same tumor associated antigen. In some embodiments, the first targeting moiety and the second targeting moiety are the same.

The first targeting moiety and the second targeting moiety may be fused to each other directly or indirectly (e.g., via a linker).

When the immunoconjugate comprises two of the targeting moiety, the first targeting moiety may be directly or indirectly fused to an amino-terminal or carboxy-terminal amino acid of one of the two subunits of the Fc domain, and the second targeting moiety may be directly or indirectly fused to an amino-terminal or carboxy-terminal amino acid of the other one of the two subunits of the Fc domain.

For example, the immunoconjugate may be a proteinaceous heterodimer. The proteinaceous heterodimer may comprise a first member and a second member different from the first member. The first member may comprise the first targeting moiety fused to one of the two subunits of the Fc domain, and the second member may comprise the single copy of SIRPα, the second targeting moiety and the other one of the two subunits of the Fc domain, with the single copy of SIRPα fused to one terminal of the Fc subunit and the second targeting moiety fused to the other terminal of the Fc subunit. The first Fc subunit may associate with the second Fc subunit to form the heterodimer.

For example, the first targeting moiety may be directly or indirectly fused to the amino-terminal amino acid of one of the two subunits of the Fc domain, the second targeting moiety may be directly or indirectly fused to the amino-terminal amino acid of the other one of the two subunits of the Fc domain, and the single copy of SIRPα may be directly or indirectly fused to the carboxy-terminal amino acid of the first or the second Fc subunit. For example, the first targeting moiety may be fused to the amino-terminal amino acid of the first Fc subunit, the second targeting moiety may be fused to the amino-terminal amino acid of the second Fc subunit, and the single copy of SIRPα may be fused to the carboxy-terminal amino acid of the second Fc subunit.

In some embodiments, when the immunoconjugate comprises two of the targeting moiety, both the first targeting moiety and the second targeting moiety may be directly or indirectly fused to the same one of the two subunits of the Fc domain.

For example, the first targeting moiety and the second targeting moiety may be directly or indirectly (e.g., via a linker) fused to each other to form a dimer of the targeting moiety. Then, the dimer of the targeting moiety may be directly or indirectly fused to one of the two subunits of the Fc domain.

The immunoconjugate may be a proteinaceous heterodimer. The proteinaceous heterodimer may comprise a first member and a second member different from the first member. The first member may comprise both the first targeting moiety and the second targeting moiety. The first targeting moiety and the second targeting moiety may be fused to the same one of the two subunits of the Fc domain (for example, the first targeting moiety and the second targeting moiety may be directly or indirectly (e.g., via a linker) fused to each other to form a dimer of the targeting moiety. Then, the dimer of the targeting moiety may be directly or indirectly fused to one of the two subunits of the Fc domain). The second member may comprise the single copy of SIRPα and the other one of the two subunits of the Fc domain. The single copy of SIRPα may be fused to one terminal of the Fc subunit. The first Fc subunit may associate with the second Fc subunit to form the heterodimer.

For example, both the first targeting moiety and the second targeting moiety may be directly or indirectly fused to the amino-terminal amino acid of the same one of the two subunits of the Fc domain (for example, the first targeting moiety and the second targeting moiety may be directly or indirectly (e.g., via a linker) fused to each other to form a dimer of the targeting moiety. Then, the dimer of the targeting moiety may be directly or indirectly fused to the amino-terminal amino acid of one of the two subunits of the Fc domain). The single copy of SIRPα may be directly or indirectly fused to the amino-terminal amino acid of the other one of the two subunits of the Fc domain. For example, the first targeting moiety and the second targeting moiety may be fused to the amino-terminal amino acid of the first Fc subunit (for example, the first targeting moiety and the second targeting moiety may be directly or indirectly (e.g., via a linker) fused to each other to form a dimer of the targeting moiety. Then, the dimer of the targeting moiety may be directly or indirectly fused to the amino-terminal amino acid of the first Fc subunit), and the single copy of SIRPα may be fused to the amino-terminal amino acid of the second Fc subunit.

The first Fc subunit may comprise the first modification as defined in the present disclosure and the second Fc subunit may comprise the second modification as defined in the present disclosure.

The immunoconjugate of the present disclosure may have a % red blood cell (RBC) binding mean fluorescence intensity (MFI) of no more than about 20%, no more than about 19%, no more than about 18%, no more than about 17%, no more than about 16%, no more than about 15%, no more than about 14%, no more than about 13%, no more than about 12%, no more than about 11%, no more than about 10%, no more than about 8%, no more than about 6%, no more than about 4%, no more than about 2% or less when % RBC binding MFI to a reference immunoconjugate is calibrated at 100%, wherein the reference immunoconjugate is a homodimer protein consisting of two identical members, each member of the homodimer protein consists of a single copy of SIRPα fused via a peptide linker to the amino-terminal amino acid of a human IgG1 Fc subunit (also referred to as SIRPα-Fc in the present application).

The immunoconjugate may also have a % platelet binding mean fluorescence intensity (MFI) of no more than about 65%, no more than about 60%, no more than about 59%, no more than about 58%, no more than about 57%, no more than about 56%, no more than about 55%, no more than about 54%, no more than about 53%, no more than about 52%, no more than about 51%, no more than about 50%, no more than about 45%, no more than about 40%, no more than about 30%, no more than about 25% or less when % platelet binding MFI to a reference immunoconjugate is calibrated at 100%, wherein the reference immunoconjugate is a homodimer protein consisting of two identical members, each member of the homodimer protein consists of a single copy of SIRPα fused via a peptide linker to the amino-terminal amino acid of a human IgG1 Fc subunit (also referred to as SIRPα-Fc IgG1 in the present application).

In some embodiments, each member of the reference immunoconjugate SIRPα-Fc IgG1 has an amino acid sequence as set forth in SEQ ID NO. 69.

The immunoconjugate may have a % red blood cell (RBC) binding mean fluorescence intensity (MFI) of no more than about 10%, no more than about 9%, no more than about 8%, no more than about 7%, no more than about 6%, no more than about 5%, no more than about 4%, no more than about 3%, no more than about 2.5%, no more than about 2%, no more than about 1.5%, no more than about 1% or less when % RBC binding MFI to a reference molecule is calibrated at 100%, wherein the reference molecule is the anti-CD47 monoclonal antibody AB6.12 IgG1.

The immunoconjugate may have a % platelet binding mean fluorescence intensity (MFI) of no more than about 50%, no more than about 45%, no more than about 46%, no more than about 45%, no more than about 44%, no more than about 43%, no more than about 42%, no more than about 41%, no more than about 40%, no more than about 39%, no more than about 38%, no more than about 37%, no more than about 36%, no more than about 35%, no more than about 34%, no more than about 33%, no more than about 32%, no more than about 31%, no more than about 30%, no more than about 25%, no more than about 20% or less when % platelet binding MFI to a reference molecule is calibrated at 100%, wherein the reference molecule is the anti-CD47 monoclonal antibody AB6.12 IgG1.

In another aspect, the present disclosure provides an isolated nucleic acid or isolated nucleic acids encoding the immunoconjugate of the present disclosure. The isolated nucleic acids may comprise one or more nucleic acid molecules, with each encoding the immunoconjugate of the present disclosure or a fragment thereof. For example, the isolated nucleic acids may comprise at least two nucleic acid molecules, with one encoding the targeting moiety fused to the first Fc subunit and the second one encoding the single copy of SIRPα fused to the second Fc subunit. In some cases, the second one may encode a polypeptide comprising a second targeting moiety fused to the second Fc subunit and the single copy of SIRPα. In some cases, the isolated nucleic acids may comprise at least three nucleic acid molecules, with one encoding a light chain of the targeting moiety, a second one encoding a heavy chain of the targeting moiety (comprising the first Fc subunit), and a third one encoding the single copy of SIRPα fused to the second Fc subunit. In some cases, the isolated nucleic acids may comprise at least four nucleic acid molecules, with one encoding a light chain of a first targeting moiety, a second one encoding a heavy chain of the first targeting moiety (comprising the first Fc subunit), a third one encoding a light chain of a second targeting moiety, and a fourth one encoding a heavy chain of the second targeting moiety (comprising the second Fc subunit) fused to the single copy of SIRPα.

The isolated nucleic acid or isolated nucleic acids may be synthesized using recombinant techniques well known in the art. For example, the isolated nucleic acid or isolated nucleic acids may be synthesized with an automated DNA synthesizer.

Standard recombinant DNA and molecular cloning techniques include those described by Sambrook, J., Fritsch, E. F. and Maniatis, T *Molecular Cloning: A Laboratory Manual*; Cold Spring Harbor Laboratory Press: Cold Spring Harbor, (1989) (Maniatis) and by T. J. Silhavy, M L. Bennan, and L. W Enquist, *Experiments with Gene Fusions*, Cold Spring Harbor Laboratory, Cold Spring Harbor, N.Y. (1984) and by Ausubel, F. M et al., *Current Protocols in Molecular Biology*, pub. by Greene Publishing Assoc. and Wiley-Interscience (1987). Briefly, the subject nucleic acids can be prepared from genomic DNA fragments, cDNAs, and RNAs, all of which can be extracted directly from a cell or recombinantly produced by various amplification processes including but not limited to PCR and RT-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. See for example, Matteuci et al., Tet. Lett. 521:719 (1980); U.S. Pat. No. 4,500,707 to Caruthers et al.; and U.S. Pat. Nos. 5,436,327 and 5,700,637 to Southern et al.

In another aspect, the present disclosure provides a vector or vectors comprising the isolated nucleic acid or isolated nucleic acids.

The vector may be any linear nucleic acids, plasmids, phagemids, cosmids, RNA vectors, viral vectors and the like. Non-limiting examples of a viral vector may include a retrovirus, an adenovirus and an adeno-associated virus. In some embodiments, the vector is an expression vector, e.g. a phage display vector.

An expression vector may be suitable for use in particular types of host cells and not others. For example, the expression vector can be introduced into the host organism, which is then monitored for viability and expression of any genes/polynucleotides contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by a variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other examples of transformation methods include microinjection, DEAE dextran mediated transformation, and heat shock in the presence of lithium acetate. Lipid complexes, liposomes, and dendrimers may also be employed to transfect the host cells.

Upon introduction of the heterologous sequence into a host cell, a variety of methods can be practiced to identify the host cells into which the subject vectors have been introduced. One exemplary selection method involves subculturing individual cells to form individual colonies, followed by testing for expression of the desired protein product. Another method entails selecting host cells containing the heterologous sequence based upon phenotypic traits conferred through the expression of selectable marker genes contained within the expression vector.

For example, the introduction of various heterologous sequences of the disclosure into a host cell can be confirmed by methods such as PCR, Southern blot or Northern blot hybridization. For example, nucleic acids can be prepared from the resultant host cells, and the specific sequences of interest can be amplified by PCR using primers specific for the sequences of interest. The amplified product is subjected to agarose gel electrophoresis, polyacrylamide gel electrophoresis or capillary electrophoresis, followed by staining with ethidium bromide, SYBR Green solution or the like, or detection of DNA with a UV detection. Alternatively, nucleic acid probes specific for the sequences of interest can be employed in a hybridization reaction. The expression of a specific gene sequence can be ascertained by detecting the corresponding mRNA via reverse-transcription coupled with PCR, Northern blot hybridization, or by immunoassays using antibodies reactive with the encoded gene product. Exemplary immunoassays include but are not limited to ELISA, radio-immunoassays, and sandwich immunoassays.

Furthermore, the introduction of various heterologous sequences of the disclosure into a host cell can be confirmed by the enzymatic activity of an enzyme (e.g., an enzymatic marker) that the heterologous sequence encodes. The enzyme can be assayed by a variety of methods known in the art. In general, the enzymatic activity can be ascertained by the formation of the product or conversion of a substrate of an enzymatic reaction that is under investigation. The reaction can take place in vitro or in vivo.

In another aspect, the present disclosure provides an isolated host cell comprising the isolated nucleic acid or isolated nucleic acids of the present disclosure or the vector or vectors of the present disclosure.

The cell may express the immunoconjugate and/or the protein mixture of the present disclosure, the isolated nucleic acid or nucleic acids encoding the immunoconjugate and/or the protein mixture of the present disclosure. The cell may be a eukaryotic cell or a prokaryotic cell. An appropriate cell may be transformed or transfected with the nucleic acid(s) or vector(s) of the present disclosure, and utilized for the expression and/or secretion of the immunoconjugate and/or protein mixtures. For example, the cell may be E. coli cells, other bacterial host cells, yeast cells, or various higher eukaryotic cells.

In another aspect, the present disclosure provides a method for producing the immunoconjugate of the present disclosure, comprising (i) culturing the host cell under conditions to effect expression and formation of the immunoconjugate, and (ii) harvesting the immunoconjugate formed.

In one aspect, the present disclosure provides a protein mixture comprising the immunoconjugate of the present disclosure. The immunoconjugate may be a proteinaceous heterodimer formed by a first member and a second member. The protein mixture may comprise a first homodimer formed by two identical copies of the first member, wherein each of the first members comprises the targeting moiety fused to the first Fc subunit; a second homodimer formed by two identical copies of the second member, wherein each of the second members comprises the single copy of SIRPα fused to the second Fc subunit; wherein the immunoconjugate of the present disclosure is present in the protein mixture with a percentage of at least about 50%, at least about 55%, at least about 60%, at least about 65%, at least about 70%, at least about 75%, at least about 80%, at least about 85%, at least about 90%, at least about 95% or at least about 99%.

In the protein mixture, the percentage of the second homodimer may be less than the percentage of the first homodimer. For example, the percentage of the second homodimer may be at most about 10%, at most about 9%, at most about 8%, at most about 7%, at most about 6%, at most about 5%, at most about 4%, at most about 3%, at most about 2%, at most about 1% or at most about 0.5%. For example, the protein mixture may substantially comprise none of the second homodimer.

The protein mixture may be obtained directly from the host cell of the present disclosure. For example, the protein mixture may be obtained from the host cell without further protein purification.

In another aspect, the present disclosure provides a method for producing the protein mixture, comprising (i) culturing the host cell under conditions to effect expression and formation of the immunoconjugate, and (ii) harvesting the protein mixture comprising the immunoconjugate.

Pharmaceutical Compositions

In another aspect, the present disclosure provides a pharmaceutical composition comprising an effective amount of the immunoconjugate, and optionally a pharmaceutically acceptable excipient.

The pharmaceutical composition may further comprise an effective amount of an additional therapeutically active component for cancer treatment. For example, the additional therapeutically active component for cancer treatment may be an agent for chemotherapy. For example, the agent for chemotherapy may be a cytotoxic agent. For example, the cytotoxic agent may be doxorubicin. Each of the active components may be present in the pharmaceutical composition in a pharmaceutically active amount.

Described below are non-limiting exemplary pharmaceutical compositions and methods for preparing the same.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition may be a liquid pharmaceutical composition suitable for oral consumption.

Pharmaceutical compositions of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods typically include the step of bringing the active ingredient into association with the carrier, which constitutes one or more other ingredients. In general, the compositions are prepared by uniformly and intimately admixing the active ingredient with liquid carriers or finely divided solid carriers or both, and then, if necessary, shaping the product into the desired presentation.

An immunoconjugate or a protein mixture of the present disclosure can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period.

Surfactant which can be used to form pharmaceutical compositions and dosage forms of the disclosure include, but are not limited to, hydrophilic surfactants, lipophilic surfactants, and mixtures thereof. A mixture of hydrophilic surfactants may be employed, a mixture of lipophilic surfactants may be employed, or a mixture of at least one hydrophilic surfactant and at least one lipophilic surfactant may be employed.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

The composition may include a solubilizer to ensure good solubilization and/or dissolution of the immunoconjugate or the protein mixture of the present disclosure and to minimize precipitation of the immunoconjugate or protein mixture of the present disclosure. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol and mixtures thereof. The amount of solubilizer that can be included is not particularly limited. The amount of a given solubilizer may be limited to a bioacceptable amount, which may be readily determined by one of skill in the art.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

The pharmaceutical compositions of the present disclosure may comprise a therapeutically effective amount of the active agent (e.g., the immunoconjugate or the protein mixture of the present disclosure). A therapeutically effective amount is an amount of the subject pharmaceutical composition capable of preventing and/or curing (at least partially) a condition or disorder (e.g., cancer) and/or any complications thereof in a subject suffering from or having a risk of developing said condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 50 mg/kg/day; sometimes, the dosage can be even higher. For example, the dosage applied may be from about 3 mg/kg/day to about 3.5 mg/kg/day, from 3.5 mg/kg/day to about 7.2 mg/kg/day, from about 7.2 mg/kg/day to about 11.0 mg/kg/day, from about 11.0 mg/kg/day to about 15.0 mg/kg/day. For example, the dosage applied may be from about 10 mg/kg/day to about 50 mg/kg/day, for example, from about 20 mg to about 50 mg per day, administered twice/day. It shall be understood that these specific doses may be conveniently adjusted by a skilled person in the art (e.g., a doctor or a pharmacist) based on conditions of a specific patient, formulation, and/or disease.

Medical Use and Methods of Treatment

In one aspect, the present disclosure provides the immunoconjugate, the protein mixture, or the pharmaceutical composition of the present disclosure, for treating a disease in a subject in need thereof.

In another aspect, the present disclosure provides a use of the immunoconjugate, the protein mixture, or the pharmaceutical composition of the present disclosure in the preparation of a medicament, wherein the medicament is for treating a disease in a subject in need thereof.

In one aspect, the present disclosure provides a use of the immunoconjugate, or the protein mixture in combination with the additional therapeutically active component (such as an agent for chemotherapy, for example, the cytotoxic agent, e.g., doxorubicin) in the preparation of a medicament for treating a disease in a subject in need thereof.

In another aspect, the present disclosure provides a method for treating a disease in a subject in need thereof, comprising administering to the subject an effective amount of the immunoconjugate, the protein mixture, or the pharmaceutical composition of the present disclosure.

In a further aspect, the present disclosure provides a method for treating a disease in a subject in need thereof, comprising administering to the subject an effective amount of the immunoconjugate, or the protein mixture of the present disclosure, and further administering to the subject an effective amount of the additional therapeutically active component (such as an agent for chemotherapy, for example, the cytotoxic agent, e.g., doxorubicin). The immunoconjugate, or the protein mixture of the present disclosure and the additional therapeutically active component may be administered concurrently or sequentially.

The disease may be cancer. For example, the cancer may comprise tumor cells with elevated expression of CD47. For example, the cancer may be selected from the group consisting of: lung cancer, bladder cancer, gastric cancer, kidney cancer, liver cancer, ovarian cancer, pancreatic cancer, prostate cancer, glioma, glioblastoma, esophageal cancer, leiomyosarcoma, acute myeloid leukemia, acute lymphoblastic leukemia, chronic lymphocytic leukemia, chronic myeloid leukemia, diffuse large B cell lymphoma, follicular lymphoma, mantle cell lymphoma, marginal zone lymphoma, multiple myeloma, myelodysplastic syndrome, breast cancer, melanoma, and colon cancer. In some embodiments, the cancer is selected from the group consisting of: breast cancer, melanoma, and colon cancer.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EXAMPLES

The following examples are set forth so as to provide those of ordinary skill in the art with a complete disclosure and description of how to make and use the present application, and are not intended to limit the scope of what the applicants regard as their application nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, temperature is in degrees Celsius, and pressure is at or near atmospheric. Standard abbreviations may be used, e.g., s or sec, second(s); min, minute(s); h or hr, hour(s); i.p., intraperitoneal(ly) and the like.

Example 1 Protein Preparation 1.1 Fc Modifications

Amino acid modifications (e.g., amino acid substitutions) were made to the interface residues of human IgG1 Fc domain to obtain the following groups of modifications (as shown in table 1 below), chain A is also referred to as Fc9 or the first Fc subunit, and chain B is also referred to as Fc6 or the second Fc subunit in the present disclosure:

TABLE 1

Groups of amino acid modifications

| Group | Fc Chain | Modifications | SEQ ID NO |
|---|---|---|---|
| 1 | A | Y349C + T366W | 1 |
|   | B | D356C + T366S + L368A + Y407V + F405K | 2 |
| 2 | A | Y349C + T366W + F405K | 3 |
|   | B | D356C + T366S + L368A + Y407V | 4 |
| 3 | A | Y349C + T366W + K409E | 5 |
|   | B | D356C + T366S + L368A + Y407V + F405K | 2 |
| 4 | A | Y349C + T366W + K409A | 6 |
|   | B | D356C + T366S + L368A + Y407V + F405K | 2 |
| 5 | A | Y349C + T366W + F405K + K360E + Q347E | 7 |
|   | B | D356C + T366S + L368A + Y407V + Q347R | 8 |
| 6 | A | Y349C + T366W + F405K + Q347R | 9 |
|   | B | D356C + T366S + L368A + Y407V + K360E + Q347E | 10 |

TABLE 1-continued

Groups of amino acid modifications

| Group | Fc Chain | Modifications | SEQ ID NO |
|---|---|---|---|
| 7 | A | Y349C + T366W + K409A + K360E + Q347E | 11 |
|   | B | D356C + T366S + L368A + Y407V + F405K + Q347R | 12 |
| 8 | A | Y349C + T366W + K409A + Q347R | 13 |
|   | B | D356C + T366S + L368A + Y407V + F405K + K360E + Q347E | 14 |
| 9 | A | T366W + K409A + K392D | 15 |
|   | B | T366S + L368A + Y407V + D399S + F405K | 16 |
| 10 | A | T366W + K409A | 17 |
|    | B | T366S + L368G + Y407A + F405K | 18 |
| 11 | A | T366W + K409A + Y349D | 19 |
|    | B | T366S + L368A + Y407V + F405K + E357A | 20 |
| 12 | A | T366W + K409A + Y349D + S354D | 21 |
|    | B | T366S + L368A + Y407V + F405K + E357A | 20 |
| 13 | A | T366W + F405K | 22 |
|    | B | T366S + L368A + Y407V + K409A | 23 |
| 14 | A | T366W + F405K + D399S | 24 |
|    | B | T366S + L368A + Y407V + K409A + K392D | 25 |
| 15 | A | T366W + F405K | 22 |
|    | B | T366S + L368G + Y407A + K409A | 26 |
| 16 | A | T366W + F405K + Y349D | 27 |
|    | B | T366S + L368A + Y407V + K409A + E357A | 28 |
| 17 | A | T366W + F405K + Y349D + S354D | 29 |
|    | B | T366S + L368A + Y407V + K409A + E357A | 28 |

Subsequently, formation of heterodimer proteins comprising the groups of modifications listed in Table 1 above were examined using a ScFv-Fc/Fc system, as explained in detail below.

First of all, human immunoglobulin gamma1 (IgG1) constant region amino acid sequence was obtained from the database Uniprot (P01857), to get wildtype human IgG1-Fc region amino acid sequence (SEQ ID NO: 30). The polynucleotide fragment encoding wild type human IgG1-Fc was obtained by RT-PCR from human PBMC total RNA (SEQ ID NO: 31, named as the Fc gene fragment). A polynucleotide fragment encoding a mouse kappaIII signal peptide (SEQ ID NO: 32) was added to the 5' end of the Fc gene by overlapping PCR, and then subcloned into the vector pcDNA4 (Invitrogen, Cat V86220), to obtain a recombinant expression vector for expressing human IgG1-Fc in mammalian cells.

A nucleic acid molecule encoding a ScFv-Fc fusion protein (SEQ ID NO: 33) was synthesized, wherein the ScFv refers to an anti-HER2 single chain antibody, the amino acid sequence of the ScFv-Fc fusion protein is as set forth in SEQ ID NO: 34. The ScFv-Fc gene fragment was then subcloned into the vector pcDNA4 (Invitrogen, Cat V86220), to obtain a recombinant expression vector for expressing the ScFv-Fc fusion protein in mammalian cells.

In some cases, a polypeptide of a variable region of a camel single domain antibody (VhH) was fused to the N terminal of the Fc gene fragment to obtain a fusion gene fragment (as set forth in SEQ ID NO: 35) encoding the fusion protein VhH-Fc (as set forth in SEQ ID NO: 36). It was then subcloned into the vector pcDNA4 (Invitrogen, Cat V86220), to obtain a recombinant expression vector for expressing the fusion protein VhH-Fc in mammalian cells.

Then, the amino acid modifications as listed in Table 1 above were respectively introduced into the ScFv-Fc (groups 1-17), the VhH-Fc (groups 2, 4, 9-12, 14, 15 and 17), and the Fc gene fragment (groups 1-8) by overlapping PCR, wherein chain A refers to the Fc subunit in ScFv-Fc and chain B refers to the independent Fc subunit or the Fc subunit in VhH-Fc. The gene fragments with amino acid modifications were respectively subcloned into the vector pcDNA4 (Invitrogen, Cat V86220), to obtain recombinant expression vectors for expressing the modified ScFv-Fc fusion proteins, the modified Fc proteins, and the modified VhH-Fc fusion proteins in mammalian cells.

Then, suspend-cultured HEK293 cells (ATCC CRL-1573™) were transfected with the constructed expression vectors with PEI. For each group, the expression vector expressing the A chain (ScFv-Fc fusion protein) and that expressing the B chain (Fc protein or VhH-Fc fusion protein) were co-transfected at a ratio of 1:1. After culturing for 5-6 days, supernatant of the transient expression products was collected, and the expression products comprising corresponding protein heterodimers were preliminarily purified using ProteinA affinity chromatography. Each of the preliminarily purified expression products comprises the homodimer protein ScFv-Fc/ScFv-Fc, the homodimer protein Fc/Fc (or the homodimer protein VhH-Fc/VhH-Fc) and the heterodimer protein ScFv-Fc/Fc (or the heterodimer protein ScFv-Fc/VhH-Fc), present in various percentages, respectively. Since the molecular weight of these proteins (i.e., the homodimers and the heterodimers) are different, their corresponding percentage could be determined according to corresponding band intensities reflected on non-reduced SDS-PAGE gels. The intensities were quantified and the results are summarized in tables 2-5 below.

TABLE 2

Percentage of homodimer proteins and heterodimer proteins in expression products

| Group | ScFv-Fc homodimer (%) | ScFv-Fc/Fc heterodimer (%) | Fc homodimer (%) |
|---|---|---|---|
| 1 | 24 | 58 | 18 |
| 2 | 10 | 70 | 20 |
| 3 | 25 | 57 | 18 |
| 4 | 10 | 77 | 13 |

TABLE 3

Percentage of homodimer proteins and heterodimer proteins in expression products

| Group | ScFv-Fc homodimer (%) | ScFv-Fc/Fc heterodimer (%) | Fc homodimer (%) |
|---|---|---|---|
| 2 | 17 | 60 | 23 |
| 5 | 14 | 72 | 14 |
| 6 | 14 | 62 | 24 |
| 4 | 21 | 69 | 10 |
| 7 | 24 | 64 | 12 |
| 8 | 21 | 71 | 8 |

TABLE 4

Percentage of homodimer proteins and heterodimer proteins in expression products

| Group | ScFv-Fc homodimer (%) | ScFv-Fc/VhH-Fc heterodimer (%) | VhH-Fc homodimer (%) |
|---|---|---|---|
| 4 | 13 | 68 | 19 |
| 9 | 7 | 80 | 13 |
| 10 | 15 | 85 | 0 |
| 11 | 14 | 83 | 3 |
| 12 | 10 | 84 | 6 |

TABLE 5

Percentage of homodimer proteins and heterodimer proteins in expression products

| Group | ScFv-Fc homodimer (%) | ScFv-Fc/VhH-Fc heterodimer (%) | VhH-Fc homodimer (%) |
|---|---|---|---|
| 2 | 9 | 64 | 27 |
| 14 | 6 | 81 | 13 |
| 15 | 5 | 88 | 7 |
| 17 | 9 | 84 | 7 |

As can be seen from tables 2-5 above, all groups of modifications promoted heterodimer formation very effectively. For illustrative purposes, the modifications in group 10 (modifications in chain A: T366W+K409A; modifications in chain B: T366S+L368G+Y407A+F405K) were used in the following examples to generate the immunoconjugate or the protein mixtures of the present disclosure.

1.2 Preparation of T-Fc9, T-LC and T-HC

Full length amino acid sequences of the heavy chain and light chain of Trastuzumab were obtained according to U.S. Pat. No. 7,879,325B2 (incorporated herein by reference). Then, corresponding DNA sequences encoding these amino acid sequences were obtained using online tool DNAworks (helixweb.nih.gov). Nucleic acid molecules encoding the light chain of Trastuzumab (T-LC) were then synthesized. The amino acid sequence of T-LC is as set forth in SEQ ID NO: 37, and the corresponding polynucleotide sequence encoding it is as set forth in SEQ ID NO: 38. Nucleic acid molecules encoding the heavy chain of Trastuzumab (T-HC) were then synthesized. The amino acid sequence of T-HC is as set forth in SEQ ID NO: 156, and the corresponding polynucleotide sequence encoding it is as set forth in SEQ ID NO: 157. Then, point mutations (T366W and K409A) were introduced into the polynucleotide sequences encoding the Fc region of Trastuzumab heavy chain gene, and nucleic acid molecules encoding the modified Trastuzumab heavy chain were synthesized (referred to herein as T-Fc9), the corresponding polypeptide encoded was named as T-Fc9. The amino acid sequences of T-Fc9 is as set forth in SEQ ID NO: 39, and the polynucleotide sequence encoding it is as set forth in SEQ ID NO:40.

1.3 Preparation of P-Fc9 and P-LC

Full length amino acid sequences of the heavy chain and light chain of Pertuzumab were obtained according to U.S. Pat. No. 7,879,325B2 (incorporated herein by reference). Then, corresponding DNA sequences encoding these amino acid sequences were obtained using online tool DNAworks (helixweb.nih.gov). Nucleic acid molecules encoding the light chain of Pertuzumab (P-LC) were then synthesized. The amino acid sequence of P-LC is as set forth in SEQ ID NO:41, and the corresponding polynucleotide sequence encoding it is as set forth in SEQ ID NO: 42. Then, point mutations (T366W and K409A) were introduced into the polynucleotide sequences encoding the Fc region of Pertuzumab heavy chain gene, and nucleic acid molecules encoding the modified Pertuzumab heavy chain were synthesized (referred to herein as P-Fc9), the corresponding polypeptide encoded was named as P-Fc9. The amino acid sequences of P-Fc9 is as set forth in SEQ ID NO: 43, and the polynucleotide sequence encoding it is as set forth in SEQ ID NO: 44.

1.4 Preparation of Mab806-Fc9 and Mab806-LC

Full length amino acid sequences of the heavy chain and light chain of Mab806 were obtained according to U.S. Pat. No. 7,589,180B2 (incorporated herein by reference). Then, corresponding DNA sequences encoding these amino acid sequences were obtained using online tool DNAworks (helixweb.nih.gov). Nucleic acid molecules encoding the light chain of Mab806 (Mab806-LC) were then synthesized. The amino acid sequence of Mab806-LC is as set forth in SEQ ID NO:45, and the corresponding polynucleotide sequence encoding it is as set forth in SEQ ID NO: 46. Then, point mutations (T366W and K409A) were introduced into the polynucleotide sequences encoding the Fc region of Mab806 heavy chain gene, and nucleic acid molecules encoding the modified Mab806 heavy chain were synthesized (referred to herein as Mab806-Fc9), the corresponding polypeptide encoded was named as Mab806-Fc9. The amino acid sequences of Mab806-Fc9 is as set forth in SEQ ID NO: 47, and the polynucleotide sequence encoding it is as set forth in SEQ ID NO: 48.

1.5 Preparation of 5E5-Fc9 and 5E5-LC

Full length amino acid sequences of the heavy chain and light chain of 5E5 were obtained according to U.S. Pat. No. 8,440,798B2 (incorporated herein by reference). Then, corresponding DNA sequences encoding these amino acid sequences were obtained using online tool DNAworks (helixweb.nih.gov). Nucleic acid molecules encoding the light chain of 5E5 (5E5-LC) were then synthesized. The amino acid sequence of 5E5-LC is as set forth in SEQ ID NO: 49, and the corresponding polynucleotide sequence encoding it is as set forth in SEQ ID NO: 50. Then, point mutations (T366W and K409A) were introduced into the polynucleotide sequences encoding the Fc region of 5E5 heavy chain gene, and nucleic acid molecules encoding the modified 5E5 heavy chain were synthesized (referred to herein as 5E5-Fc9), the corresponding polypeptide encoded was named as 5E5-Fc9. The amino acid sequences of 5E5-Fc9 is as set forth in SEQ ID NO: 51, and the polynucleotide sequence encoding it is as set forth in SEQ ID NO: 52.

1.6 Preparation of hu56-Fc9

Full length amino acid sequences of the heavy chain variable region of hu56 were obtained according to CN106397592A. Then, corresponding DNA sequences encoding these amino acid sequences were obtained using online tool DNAworks (helixweb.nih.gov). Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366W and K409A) were introduced into the IgG1-Fc fragment, and the polypeptide obtained thereby is referred to as Fc9. Then, a linker sequence "GAP" (SEQ ID NO: 53) was added to the N-terminus of the Fc9, to obtain linker-Fc9. The corresponding DNA sequence encoding it was then designed using online tool DNAworks (helixweb.nih.gov). Polynucleotide sequences encoding the heavy chain variable region of hu56 were added to the 5' end of the polynucleotide sequences encoding the linker-Fc9, thereby obtaining and synthesizing a polynucleotide sequence encoding the fusion protein hu56-Fc9. The amino acid sequence of hu56-Fc9 is as set forth in SEQ ID NO: 54, and the polynucleotide sequence encoding it is as set forth in SEQ ID NO: 55.

1.7 Preparation of hu56di-Fc9

Full length amino acid sequences of the heavy chain variable region of hu56 were obtained according to CN106397592A. Then, corresponding DNA sequences encoding these amino acid sequences were obtained using online tool DNAworks (helixweb.nih.gov). Two copies of the heavy chain variable region of hu56 were linked by a linker "GAP" (SEQ ID NO: 53) to obtain hu56di. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366W and K409A) were introduced into the IgG1-Fc fragment, and the polypeptide obtained thereby is referred to as Fc9. Then, a linker sequence "EPKSS" (SEQ ID NO: 58) was added to the N-terminus of the Fc9, to obtain linker-Fc9. The corresponding DNA sequence encoding it was then designed using online tool DNAworks (helixweb.nih.gov). Polynucleotide sequences encoding hu56di were added to the 5' end of the polynucleotide sequences encoding the linker-Fc9, thereby obtaining and synthesizing a polynucleotide sequence encoding the fusion protein hu56di-Fc9. The amino acid sequence of hu56di-Fc9 is as set forth in SEQ ID NO:56, and the polynucleotide sequence encoding it is as set forth in SEQ ID NO: 57.

1.8 Preparation of mPD-L1-Fc9

An anti-mouse PD-L1 ScFv molecule (B50-6-ScFv) was obtained according to CN105777906A, and a nucleic acid molecule encoding a mPD-L1-ScFv-Fc fusion protein was synthesized. Nucleic acid molecules encoding the heavy chain of mPD-L1-ScFv-Fc were then synthesized. The amino acid sequence of mPD-L1-ScFv-Fc is as set forth in SEQ ID NO: 158, and the corresponding polynucleotide sequence encoding it is as set forth in SEQ ID NO: 159. Then, point mutations (T366W and K409A) were introduced into the nucleic acid molecule encoding the mPD-L1-ScFv-Fc fusion protein to obtain mPD-L1-ScFv-Fc9, the corresponding polypeptide encoded was named as mPD-L1-Fc9, and the amino acid sequence thereof is as set forth in SEQ ID NO:59, and the polynucleotide sequence encoding it is as set forth in SEQ ID NO: 60.

1.9 Preparation of CD47-muFc

The amino acid sequence of the human CD47 extracellular domain (i.e., the 19th residue to the 141th residue in Q08722) was obtained according to the amino acid sequence of human CD47 (Q08722) in the protein database Uniprot. According to the amino acid sequence of the constant region of murine immunoglobulin gamma1 (P01868) in the protein database Uniprot, the amino acid sequence of muFc (i.e., the 112th residue to the 213th residue in P01868) was obtained. The DNAworks Online Tool (helixweb.nih.gov) was used to design the corresponding coding DNA sequence to obtain the CD47-muFc fusion protein gene, and the DNA fragment was obtained by artificial synthesis. The synthetic gene sequences were cloned into commercial vector pcDNA4/myc-HisA (Invitrogen, V863-20) by Fermentas HindIII and EcoRI. The recombinant plasmids were then sequenced for confirmation, thereby obtaining the plasmid DNA of pcDNA4-CD47-muFc. The amino acid sequences of CD47-muFc is as set forth in SEQ ID NO: 61, and the polynucleotide sequence encoding it is as set forth in SEQ ID NO: 62.

1.10 Preparation of CD47-EGFP

The full length amino acid sequence of the human CD47 was obtained according to the amino acid sequence of human CD47 (Q08722) in the protein database Uniprot. According to the amino acid sequence of the Enhanced Green Fluorescent Protein, EGFP (C5MKY7) in the protein database Uniprot, the amino acid sequence of EGFP was obtained. The DNAworks Online Tool (helixweb.nih.gov) was as used to design the corresponding coding DNA sequence to obtain the CD47-EGFP fusion protein gene, and the DNA fragment was obtained by artificial synthesis. The synthetic gene sequences were cloned into commercial vector pcDNA4/myc-HisA (Invitrogen, V863-20) by Fermentas HindIII and EcoRI. The recombinant plasmids were sequenced for confirmation, thereby obtaining the plasmid DNA of pcDNA4-CD47-EGFP. The amino acid sequences of CD47-EGFP is as set forth in SEQ ID NO: 63, and the polynucleotide sequence encoding it is as set forth in SEQ ID NO: 64.

1.11 Preparation of SIRPα-Fc6

First of all, sequence information of human SIRPα (NM 080792.2) was obtained from the National Center for Biotechnology Information (NCBI), and the full-length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "GGGGS" (SEQ ID NO: 65) was added to the N-terminus of the Fc6, to obtain linker-Fc6. The corresponding DNA sequence encoding it was then designed using online tool DNAworks (helixweb.nih.gov). Polynucleotide sequences encoding human SIRPα were added to the 5' end of the polynucleotide sequences encoding the linker-Fc6, thereby obtaining and synthesizing a polynucleotide sequence encoding the fusion protein human SIRPα-Fc6. The amino acid sequence of human SIRPα-Fc6 (SIRPα-Fc6) is as set forth in SEQ ID NO:66, and the polynucleotide sequence encoding it is as set forth in SEQ ID NO: 67.

1.12 Preparation of SIRPα-Fc IgG1

First of all, sequence information of human SIRPα (NM_080792.2) was obtained from the National Center for Biotechnology Information (NCBI), and the full-length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Then, a linker sequence "GAPGG" (SEQ ID NO: 68) was added to the N-terminus of the IgG1-Fc, to obtain linker- IgG1-Fc. The corresponding DNA sequence encoding it was then designed using online tool DNAworks (helixweb.nih.gov). Polynucleotide sequences encoding human SIRPα were added to the 5' end of the polynucleotide sequences encoding the linker-IgG1-Fc, thereby obtaining and synthesizing a polynucleotide sequence encoding the fusion protein human SIRPα-Fc IgG1. The amino acid sequence of human SIRPα-Fc IgG1 (short for SIRPα-Fc IgG1) is as set forth in SEQ ID NO: 69, and the polynucleotide sequence encoding it is as set forth in SEQ ID NO: 70.

1.13 Preparation of hu56-Fc6-SIRPα

Full length amino acid sequences of the heavy chain variable region of hu56 were obtained according to CN106397592A. Then, corresponding DNA sequences encoding these amino acid sequences were obtained using online tool DNAworks (helixweb.nih.gov). Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "GGGGS" (SEQ ID NO: 65) was added to the N-terminus of the Fc6, to obtain linker-Fc6, and a linker sequence "(GGGGS)$_3$" (SEQ ID NO: 71) was added to the C-terminus of the linker-Fc6, to obtain linker-Fc6-linker. The sequence information of human SIRPα (NM_080792.2) was obtained from the National Center for Biotechnology Information (NCBI), and the full-length polynucleotide sequences encoding it were obtained. Polynucleotide sequences encoding human SIRPα were added to the 3' end of the polynucleotide sequences encoding the linker-Fc6-linker, thereby obtaining and synthesizing a polynucleotide sequence encoding the fusion protein linker-Fc6-SIRPα. Then, the heavy chain variable region of hu56 was fused to the N-terminus of linker-Fc6-SIRPα, to obtain hu56-Fc6-SIRPα. The amino acid sequence of hu56-Fc6-SIRPα is as set forth in SEQ ID NO: 72, and the polynucleotide sequence encoding it is as set forth in SEQ ID NO: 73.

1.14 Preparation of ate-Fc9 and ate-LC

Full length amino acid sequences of the heavy chain and light chain of atezolizumab were obtained from www.imgt.org. Then, corresponding DNA sequences encoding these amino acid sequences were obtained using online tool DNAworks (helixweb.nih.gov). Nucleic acid molecules encoding the light chain of atezolizumab (ate-LC) were then synthesized. The amino acid sequence of ate-LC is as set forth in SEQ ID NO: 74, and the corresponding polynucleotide sequence encoding it is as set forth in SEQ ID NO:75. Then, point mutations (T366W and K409A) were introduced into the polynucleotide sequences encoding the Fc region of amatuximab heavy chain gene, and nucleic acid molecules encoding the modified atezolizumab heavy chain were synthesized (referred to herein as ate-Fc9), the corresponding polypeptide encoded was named as ate-Fc9. The amino acid sequences of ate-Fc9 is as set forth in SEQ ID NO: 76, and the polynucleotide sequence encoding it is as set forth in SEQ ID NO: 77.

1.15 Preparation of ave-Fc9 and ave-LC

Full length amino acid sequences of the heavy chain and light chain of avelumab were obtained from www.imgt.org. Then, corresponding DNA sequences encoding these amino acid sequences were obtained using online tool DNAworks (helixweb.nih.gov). Nucleic acid molecules encoding the light chain of avelumab (ave-LC) were then synthesized. The amino acid sequence of ave-LC is as set forth in SEQ ID NO: 78, and the corresponding polynucleotide sequence encoding it is as set forth in SEQ ID NO: 79. Then, point mutations (T366W and K409A) were introduced into the polynucleotide sequences encoding the Fc region of avelumab heavy chain gene, and nucleic acid molecules encoding the modified avelumab heavy chain were synthesized (referred to herein as ave-Fc9), the corresponding polypeptide encoded was named as ave-Fc9. The amino acid sequences of ave-Fc9 is as set forth in SEQ ID NO: 80, and the polynucleotide sequence encoding it is as set forth in SEQ ID NO: 81.

1.16 Preparation of dur-Fc9 and dur-LC

Full length amino acid sequences of the heavy chain and light chain of durvalumab were obtained from www.imgt.org. Then, corresponding DNA sequences encoding these amino acid sequences were obtained using online tool DNAworks (helixweb.nih.gov). Nucleic acid molecules encoding the light chain of durvalumab (dur-LC) were then synthesized. The amino acid sequence of dur-LC is as set forth in SEQ ID NO: 82, and the corresponding polynucleotide sequence encoding it is as set forth in SEQ ID NO: 83. Then, point mutations (T366W and K409A) were introduced into the polynucleotide sequences encoding the Fc region of durvalumab heavy chain gene, and nucleic acid molecules encoding the modified durvalumab heavy chain were synthesized (referred to herein as dur-Fc9), the corresponding polypeptide encoded was named as dur-Fc9. The amino acid sequences of dur-Fc9 is as set forth in SEQ ID NO: 84, and the polynucleotide sequence encoding it is as set forth in SEQ ID NO: 85.

1.17 Preparation of CV1-Fc6 and CV1-Fc

First of all, sequence information and the synthesis approach of CV1 were described in Weiskopf K. et. al. Engineered SIRPα variants as immunotherapeutic adjuvants to anti-cancer antibodies, Science, 2013, 341(6141): 88-91. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "GGGGS" (SEQ ID NO: 65) was added to the N-terminus of the Fc6, to obtain linker-Fc6. The corresponding DNA sequence encoding it was then designed using online tool DNAworks (helixweb.nih.gov). Polynucleotide sequences encoding CV1 were added to the 5' end of the polynucleotide sequences encoding the linker-Fc6, thereby obtaining and synthesizing a polynucleotide sequence encoding the fusion protein human CV1-Fc6. The amino acid sequence of CV1-Fc6 is as set forth in SEQ ID NO:148, and the polynucleotide sequence encoding it is as set forth in SEQ ID NO: 149.

Amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Then, a linker sequence "GAPGG" (SEQ ID NO: 68) was added to the N-terminus of the IgG1-Fc, to obtain linker-IgG1-Fc. The corresponding DNA sequence encoding it was then designed using online tool DNAworks (helixweb.nih.gov). Polynucleotide sequences encoding human CV1 were added to the 5' end of the polynucleotide sequences encoding the linker-IgG1-Fc, thereby obtaining and synthesizing a polynucleotide sequence encoding the fusion protein human CV1-Fc. The amino acid sequence of human CV1-Fc is as set forth in SEQ ID NO: 154, and the polynucleotide sequence encoding it is as set forth in SEQ ID NO: 155.

1.18 Preparation of mCD47-ScFv-Fc6

A anti-mouse CD47 ScFv molecule (miap-301-ScFv) was synthesized. Nucleic acid molecules encoding the heavy chain of mCD47-ScFv-Fc were then synthesized. The amino acid sequence of mCD47-ScFv-Fc is as set forth in SEQ ID NO: 160, and the corresponding polynucleotide sequence encoding it is as set forth in SEQ ID NO: 161. Then, point mutations (T366S, L368G, Y407A and F405K) were introduced into the nucleic acid molecule encoding the mCD47-ScFv-Fc fusion protein, to obtain mCD47-ScFv-Fc6, the corresponding polypeptide encoded was named as mCD47-ScFv-Fc6, and the amino acid sequence thereof is as set forth in SEQ ID NO:162, and the polynucleotide sequence encoding it is as set forth in SEQ ID NO: 163.

1.19 Preparation of mSIRPα-Fc6 and mSIRPα-Fc

First of all, sequence information of mouse SIRPα (NM_001177647.2) was obtained from the National Center for Biotechnology Information (NCBI), and the full-length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Then, a linker sequence "GAPGG" (SEQ ID NO: 68) was added to the N-terminus of the IgG1-Fc, to obtain linker-IgG1-Fc. The corresponding DNA sequence encoding it was then designed using online tool DNAworks (helixweb.nih.gov). Polynucleotide sequences encoding mSIRPα were added to the 5' end of the polynucleotide sequences encoding the linker-IgG1-Fc, thereby obtaining and synthesizing a polynucleotide sequence encoding the fusion protein mSIRPα-Fc. The amino acid sequence of mSIRPα-Fc is as set forth in SEQ ID NO: 152, and the polynucleotide sequence encoding it is as set forth in SEQ ID NO: 153. Afterwards, point mutations (T366S, L368G, Y407A and F405K) were introduced into the IgG1-Fc fragment, and the polypeptide obtained thereby is referred to as Fc6. Then, a linker sequence "GGGGS" (SEQ ID NO: 65) was added to the N-terminus of the Fc6, to obtain linker-Fc6. The corresponding DNA sequence encoding it was then designed using online tool DNAworks (helixweb.nih.gov). Polynucleotide sequences encoding mouse SIRPα were added to the 5' end of the polynucleotide sequences encoding the linker-Fc6, thereby obtaining and synthesizing a polynucleotide sequence encoding the fusion protein mouse SIRPα-Fc6. The amino acid sequence of mouse SIRPα-Fc6 (mSIRPα-Fc6) is as set forth in SEQ ID NO:150, and the polynucleotide sequence encoding it is as set forth in SEQ ID NO: 151.

1.20 Preparation of AB6.12-HC and AB6.12-LC

Full length amino acid sequences of the heavy chain and light chain of AB6.12 were obtained according to WO2014123580A (incorporated herein by reference). Then, corresponding DNA sequences encoding these amino acid sequences were obtained using online tool DNAworks (helixweb.nih.gov). Nucleic acid molecules encoding the light chain of AB6.12 (AB6.12-LC) were then synthesized. The amino acid sequence of AB6.12-LC is as set forth in SEQ ID NO: 166, and the corresponding polynucleotide sequence encoding it is as set forth in SEQ ID NO: 167. Nucleic acid molecules encoding the heavy chain of AB6.12 (AB6.12-HC) were then synthesized. The amino acid sequence of AB6.12-HC is as set forth in SEQ ID NO: 164, and the corresponding polynucleotide sequence encoding it is as set forth in SEQ ID NO: 165.

Example 2 Construction of Recombinant Plasmids

The nucleic acid molecules (encoding T-Fc9, P-Fc9, Mab806-Fc9, 5E5-Fc9, hu56-Fc9, hu56di-Fc9, ate-Fc9, ave-Fc9, dur-Fc9, mPD-L1-Fc9, T-LC (Trastuzumab light chain), P-LC (Pertuzumab light chain), Mab806-LC (Mab806 light chain), 5E5-LC (5E5 light chain), AB6.12-LC (AB6.12 light chain), ate-LC, ave-LC, dur-LC, SIRPα-Fc6, SIRPα-Fc IgG1, CV1-Fc6, hu56-Fc6-SIRPα, mSIRPα-Fc6, T-HC (Trastuzumab heavy chain), AB6.12-HC (AB6.12 heavy chain), CV1-Fc, scFv-Fc and mCD47-scFv-Fc6, respectively) obtained according to Example 1 were digested with HindIII and EcoRI (Takara), and then sub-cloned into the vector pcDNA4/myc-HisA (Invitrogen, V863-20), respectively. The plasmids obtained were verified by sequencing, and the correct recombinant plasmids were named as: pcDNA4-T-Fc9, pcDNA4-P-Fc9, pcDNA4-Mab806-Fc9, pcDNA4-5E5-Fc9, pcDNA4-hu56-Fc9, pcDNA4-hu56di-Fc9, pcDNA4-ate-Fc9, pcDNA4-ave-Fc9, pcDNA4-dur-Fc9, pcDNA4-mPD-L1-Fc9, pcDNA4-T-LC, pcDNA4-P-LC, pcDNA4-Mab806-LC, pcDNA4-5E5-LC, pcDNA4-AB6.12-LC, pcDNA4-ate-LC, pcDNA4-ave-LC, pcDNA4-dur-LC, pcDNA4-SIRPα-Fc6, pcDNA4-SIRPα-Fc IgG1, pcDNA4-CV1-Fc6, pcDNA4-hu56-Fc6-SIRPα, pcDNA4-mSIRPα-Fc6, pcDNA4-T-HC, pcDNA4-AB6.12-HC, pcDNA4-CV1-Fc, pcDNA4-scFv-Fc and pcDNA4-mCD47-scFv-Fc6, respectively.

Example 3 Expression and Purification of Proteinaceous Heterodimers

Two days before transfection, 12×600 mL suspension domesticated HEK293 (ATCC, CRL-1573™) cells were prepared for transient transfection, the cells were seeded at a density of 0.8×10⁶ cells/ml. Two days later, three aliquots of cell suspension were centrifuged, and then resuspended in 600 mL Freestyle293 culture medium.

The recombinant expression vectors obtained from Example 2 were divided into the following groups:

Group 1: pcDNA4-T-Fc9 (200 µg)+pcDNA4-T-LC (200 µg)+pcDNA4-SIRPα-Fc6(200 µg)

Group 2: pcDNA4-P-Fc9 (200 µg)+pcDNA4-P-LC (200 µg)+pcDNA4-SIRPα-Fc6(200 µg)

Group 3: pcDNA4-Mab806-Fc9 (200 µg)+pcDNA4-Mab806-LC (200 µg)+pcDNA4-SIRPα-Fc6(200 µg)

Group 4: pcDNA4-5E5-Fc9(200 µg)+pcDNA4-5E5-LC (200 µg)+pcDNA4-SIRPα-Fc6(200 µg)

Group 5: pcDNA4-hu56di-Fc9(200 µg)+pcDNA4-SIRPα-Fc6(200 µg)

Group 6: pcDNA4-mPD-L1-Fc9(200 µg)+pcDNA4-mSIRPα-Fc6(200 µg)

Group 7: pcDNA4-SIRPα-Fc IgG1 (200 µg) Group 8: pcDNA4-CD47-muFc (200 µg)

Group 9: pcDNA4-CD47-EGFP (200 µg)

Group 10: pcDNA4-hu56-Fc9(200 µg)+pcDNA4-hu56-Fc6-SIRPα(200 µg)

Group 11: pcDNA4-ate-Fc9(200 µg)+pcDNA4-ate-LC (200 µg)+pcDNA4-SIRPα-Fc6(200 µg)

Group 12: pcDNA4-ave-Fc9(200 µg)+pcDNA4-ave-LC (200 µg)+pcDNA4-SIRPα-Fc6(200 µg)

Group 13: pcDNA4-dur-Fc9(200 µg)+pcDNA4-dur-LC (200 µg)+pcDNA4-SIRPα-Fc6(200 µg)

Group 14: pcDNA4-hu56di-Fc9(200 µg)+pcDNA4-CV1-Fc6(200 µg)

Group 15: pcDNA4-mPD-L1-Fc9(200 µg)+pcDNA4-CV1-Fc6(200 µg)

Group 16: pcDNA4-T-Fc9 (200 µg)+pcDNA4-T-LC (200 µg)+pcDNA4-mSIRPα-Fc6(200 µg)

Group 17: pcDNA4-mPD-L1-scFv-Fc9 (200 µg)+pcDNA4-mCD47-scFv-Fc6 (200 µg)

Group 18: pcDNA4-mSIRPα-Fc (200 µg)

Group 19: pcDNA4-T-HC (200 µg)+pcDNA4-T-LC (200 µg)

Group 20: pcDNA4-AB6.12-HC (200 µg)+pcDNA4-AB6.12-LC (200 µg)

Group 21: pcDNA4-mPD-L1-scFv-Fc (200 µg)

Group 22: pcDNA4-mCD47-scFv-Fc (200 µg)

Group 23: pcDNA4-CV1-Fc (200 µg)

All proteins were made in transiently transfected 293F cells. Briefly, FreeStyle 293F cells (Invitrogen) were grown in 293F medium (Invitrogen), transfected with non-linearized plasmid DNA and 293Fectin reagent (Invitrogen) and grown in shaker flask batches in volumes 80-100 mL/flask at 37° C., 5% $CO_2$ for 6 days. All proteins were purified by one-step protein A chromatography. The quality of each protein was determined by SDS-PAGE. Similarly, the expression and purification results of the other immunoconjugates of the present application were verified and confirmed with SDS-PAGE.

The immunoconjugates thus obtained are named as (from Group 1 to Group 23, respectively): Tmab-SIRPα, Pmab-SIRPα, Mab806-SIRPα, 5E5-SIRPα, hu56di-SIRPα, mPD-L1-mSIRPα, SIRPα-Fc IgG1, CD47-muFc, CD47-EGFP, hu56-Fc6-SIRPα, ate-SIRPα, ave-SIRPα, dur-SIRPα, hu56di-CV1, mPD-L1-CV1, Tmab-mSIRPα, mPD-L1-mCD47, mSIRPα-Fc, KN034(Herceptin), AB6.12 IgG1, a-mPD-L1, a-mCD47 and CV1-Fc.

Figure 2:
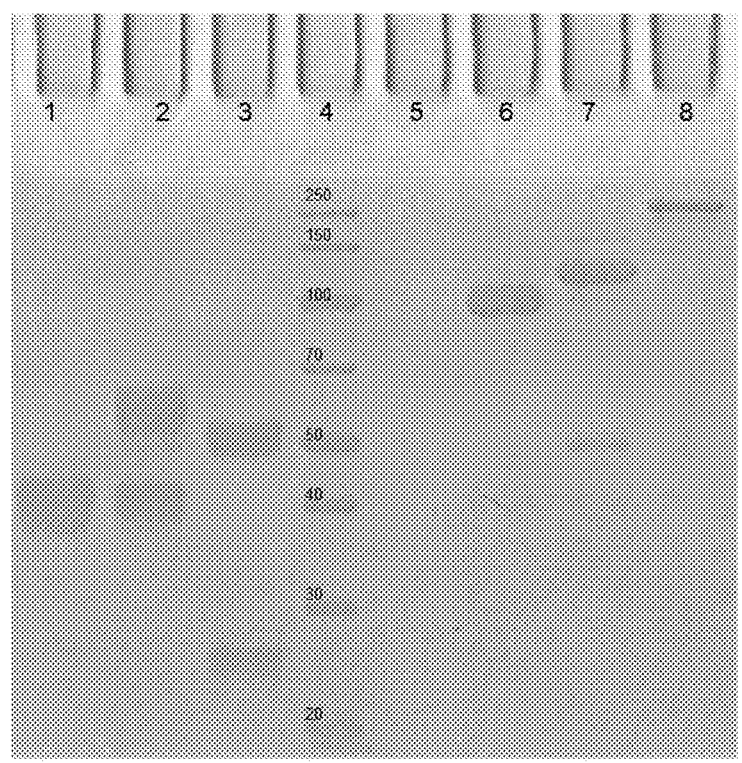
FIG. 2 illustrates the purification result of the immunoconjugate of the present disclosure, as shown by SDS-PAGE analysis.

In FIG. 2, lane 1 was loaded with SIRPα-Fc IgG1 (reducing); lane 2 was loaded with hu56di-SIRPα(reducing); lane 3 was loaded with AB6.12 IgG1(reducing); lane 4 was loaded with a protein marker; lane 5 was blank; lane 6 was loaded with SIRPα-Fc IgG1(non-reducing); lane 7 was loaded with hu56di-SIRPα(non-reducing); and lane 8 was loaded with AB6.12 IgG1(non-reducing). The results of FIG. 2 demonstrate that the immunoconjugate of the present disclosure was successfully expressed and purified.

Figure 1B:
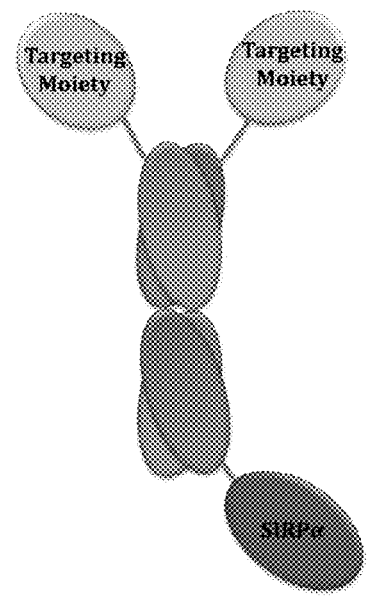

FIG. 1a-1b illustrate examples of the immunoconjugate of the present disclosure. Among the above obtained immunoconjugates (e.g., proteinaceous heterodimers), an ate-SIRPα may be an exemplary embodiment of immunoconjugate shown in FIG. 1a, while hu56-Fc6-SIRPα may be an exemplary embodiment of immunoconjugate shown in FIG. 1b.

Example 4 Binding Kinetics of the Immunoconjugate of the Present Disclosure

Binding kinetics of a hu56di-SIRPα immunoconjugate or control antibodies (SIRPα-Fc IgG1 and AB6.12 IgG1) were determined by the bio-layer inferometry (BLI) method using Octet K2 system (FortéBio). All experiments were performed at 25° C. under a PBS buffer containing 0.5% BSA and 0.5% Tween 20, pH 7.2. CD47-muFc was immobilized onto AHC Biosensors, which were subsequently used in association (with hu56di-SIRPα, SIRPα-Fc IgG1 or AB6.12 IgG1) and dissociation measurements each performed for a time window of 40 seconds and 300 seconds, respectively. After the above steps, the subtracted binding interference data were applied to the calculations of binding constants using the FortéBio analysis software provided with the instrument.

Unexpectedly, hu56di-SIRPα and SIRPα-Fc IgG1 has comparable binding affinity to CD47, as Table 6 depicted.

TABLE 6

| Sample | KD (M) | kon(1/Ms) | kdis(1/s) | Full $X^2$ | Full $R^2$ |
|---|---|---|---|---|---|
| SIRPα-Fc IgG1 | 5.81E−09 | 6.50E+05 | 3.77E−03 | 0.4161 | 0.9783 |
| hu56di-SIRPα | 5.30E−09 | 1.14E+06 | 6.07E−03 | 0.0924 | 0.9748 |
| AB6.12 IgG1 | 1.98E−10 | 6.51E+05 | 1.29E−04 | 0.0349 | 0.9994 |

Example 5 FACS Binding Affinity of the Immunoconjugate of the Present Disclosure The hu56di-SIRPα, SIRPα-Fc IgG1 and AB6.12 IgG1 were compared regarding their binding activities to cell surface human CD47. Briefly, cells expressing CD47-EGFP were incubated with hu56di-SIRPα, SIRPα-Fc IgG1 and AB6.12 IgG1 of various concentrations at 4° C. for 30 min. The cells were then washed to remove any unbound protein and then incubated with an anti-hIgG Fc gamma specific PE antibody (eBiosciences Cat #12-4998-82) at 4° C. for 20 min. The cells were then analyzed by flow cytometry (Life Technology).

Figure 3:
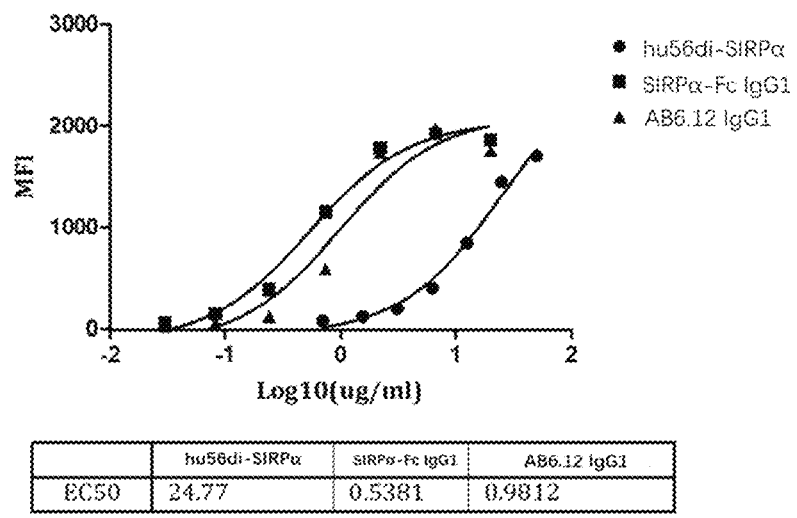
FIG. 3 illustrates the binding affinity of the immunoconjugate of the present disclosure, as shown by FACS analysis.

As shown in FIG. 3, the horizontal coordinate is the concentration of hu56di-SIRPα, SIRPα-Fc IgG1 and AB6.12 IgG1, and the vertical coordinate is the value of MFI. As expected, the binding affinity of hu56di-SIRPα was much lower than that of SIRPα-Fc IgG1 or AB6.12 IgG1, due to the single arm of SIRPα.

Example 6 In Vitro Pro-Phagocytosis Activity of the Immunoconjugate of the Present Disclosure Human macrophages were generated by monocytes from Ficoll-purified human peripheral blood mononuclear cells. Monocytes were cultured in media containing human monocyte colony stimulating factor 1 (CSF-1) at 50 ng/ml and human interleukin 10 (IL-10) at 25 ng/ml for at least 1 week to promote development into macrophages. $1 \times 10^7$ Jurket cells were labelled with 5 µM CFSE at 37° C. for 20 min. After labelling, the Jurket cells were incubated with PBS, hu56di-SIRPα or isotype controls (human IgG1) for 15 min at room temperature (RT). $1 \times 10^5$ Jurket cells were then added to the individual wells, mixed with $1 \times 10^5$ macrophage and incubated in a 37° C., 5% $CO_2$ humidified cell incubator for 2 hours. After the incubation, the wells were washed and the macrophages were analyzed by flow cytometry (Life Technology).

Figure 4:
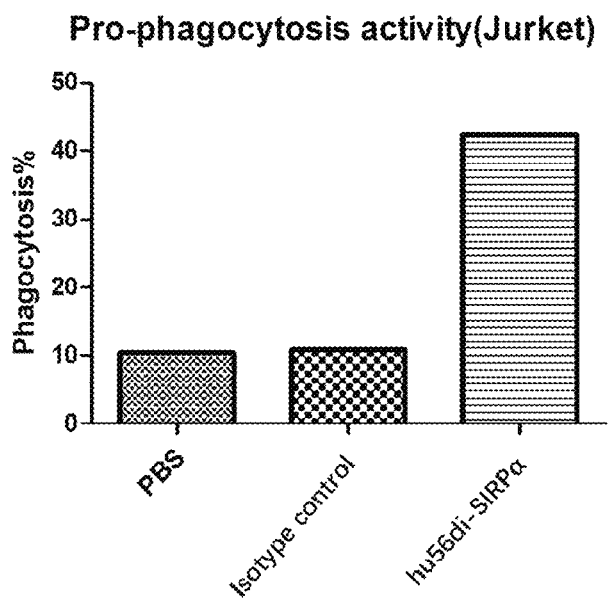
FIG. 4 illustrates the results of in vitro pro-phagocytosis activity of the immunoconjugate of the present disclosure.

The results are shown in FIG. 4. The horizontal coordinate is PBS, isotype control (human IgG1) and hu56di-SIRPα, and the vertical coordinate is the percentage of phagocytosis. It can be seen that hu56di-SIRPα exhibits strong pro-phagocytosis activity compared with PBS and isotype control group.

Example 7 Dual Antigen Tumor Binding of the Immunoconjugate of the Present Disclosure Tumor binding affinity of dual antigen and mono antigen were determined by FACS. A375 cell (expressing CD47) and A375-PD-L1 tumor cells (expressing both CD47 and PD-L1) were incubated with various concentration of hu56di-SIRPα at 4° C. for 30 min. Then cells were washed to remove unbound proteins and incubated with an anti-hIgG Fc gamma specific PE antibody (eBiosciences Cat #12-4998-82) at 4° C. for 20 min. The cells were analyzed by flow cytometry (Life Technology).

Figure 5:
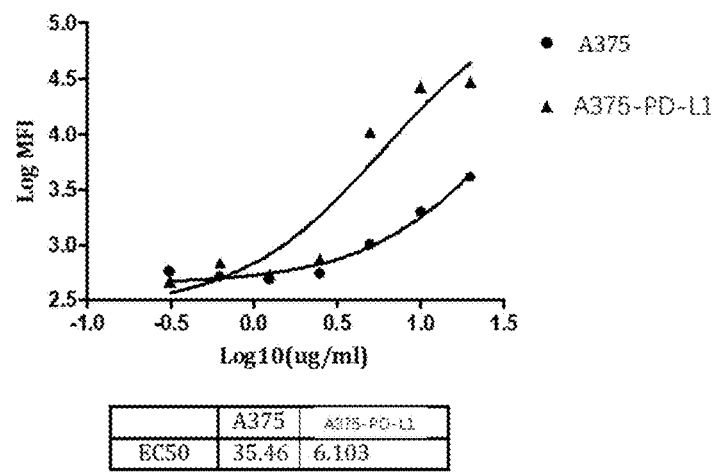
FIG. 5 illustrates the results of tumor binding affinity of the immunoconjugate of the present disclosure.

The results are shown in FIG. 5. The horizontal coordinate is the concentration of hu56di-SIRPα, and the vertical coordinate is the log value of MFI. The result demonstrates that comparing to cells expressing only mono antigen, for cells expressing dual antigens, the binding affinity of hu56di-SIRPα increases significantly.

Example 8 Tumor Binding in Excess Erythrocyte Antigen Sink

An important concern about CD47-based therapeutics is the expression of the target on the surface of erythrocyte, which has the potential to act as a large antigen sink and cause hematological toxicity. Indeed, anemia has been reported in animal treated with SIRPα-Fc IgG1 and CD47-specific antibodies. The binding of hu56di-SIRPα to tumor cell in excess human erythrocytes antigen sink was therefore assessed by flow cytometry. A375 cell (expressing CD47) and A375-PD-L1 tumor cells (expressing both CD47 and PD-L1) were mixed with a 15-fold excess of RBCs, and then incubated with 20 μg/ml hu56di-SIRPα, SIRPα-Fc IgG1 or AB6.12 IgG1 or isotype control (human IgG1) at 4° C. for 30 min. Then the cells were washed to remove unbound proteins and incubated with an anti-hIgG Fc gamma specific PE antibody at 4° C. for 20 min. The cells were analyzed by flow cytometry (Life Technology). The gate of erythrocytes was assessed by anti-human CD235a (eBiosciences Cat #12-9987-80).

Figure 6A:
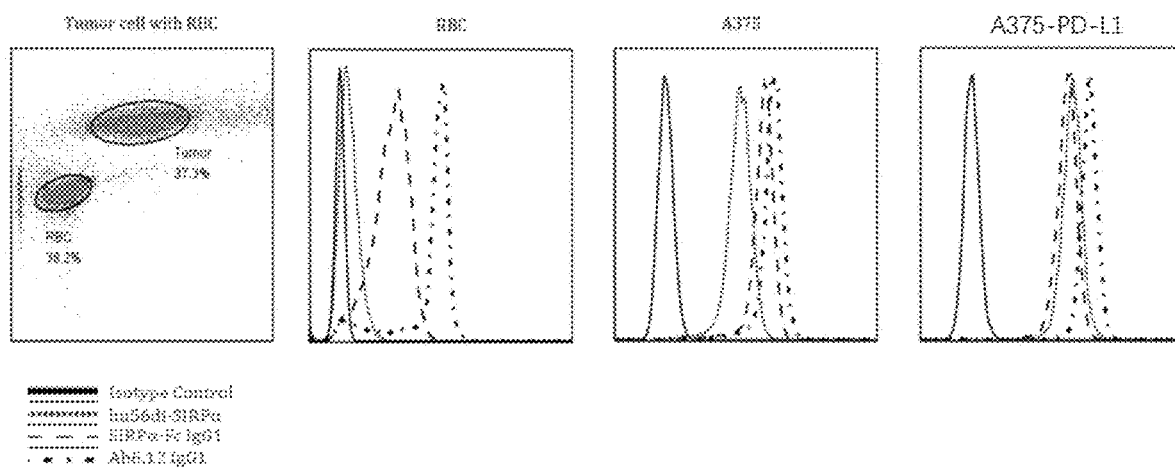

The results are shown in FIG. 6a. 15-folds excess of RBCs are mixed with various concentrations of hu56di-SIRPα, and the binding of RBC is shown. As shown in FIG. 6a, hu56di-SIRPα bound preferentially to tumor cells other than RBC. The MFI of hu56di-SIRPα binding with RBCs was similar to the isotype control. In contrast, SIRPα-Fc IgG1 and AB6.12 IgG1 bound tumor cells and RBCs at the same time. For tumor binding, the results of hu56di-SIRPα were very similar to that of SIRPα-Fc IgG1 and AB6.12 IgG1, when the tumor cells expressed dual antigen.

Similarly, the binding of hu56-SIRPα, ate-SIRPα, hu56-Fc6-SIRPα, SIRPα-Fc IgG1, and AB6.12 IgG1 to tumor cell in excess human erythrocytes antigen sink was therefore assessed by flow cytometry.

A375-PD-L1 tumor cells (expressing both CD47 and PD-L1) were mixed with a 15-fold excess of RBCs, and then incubated with 20 μg/ml hu56di-SIRPα, ate-SIRPα, hu56-Fc6-SIRPα, SIRPα-Fc IgG1, AB6.12 IgG1. or isotype control (human IgG1) at 4° C. for 30 min. Then the cells were washed to remove unbound proteins and incubated with an anti-hIgG Fc gamma specific PE antibody at 4° C. for 20 min. The cells were analyzed by flow cytometry (Life Technology). The gate of erythrocytes was assessed by anti-human CD235a (eBiosciences Cat #12-9987-80).

Figure 6B:
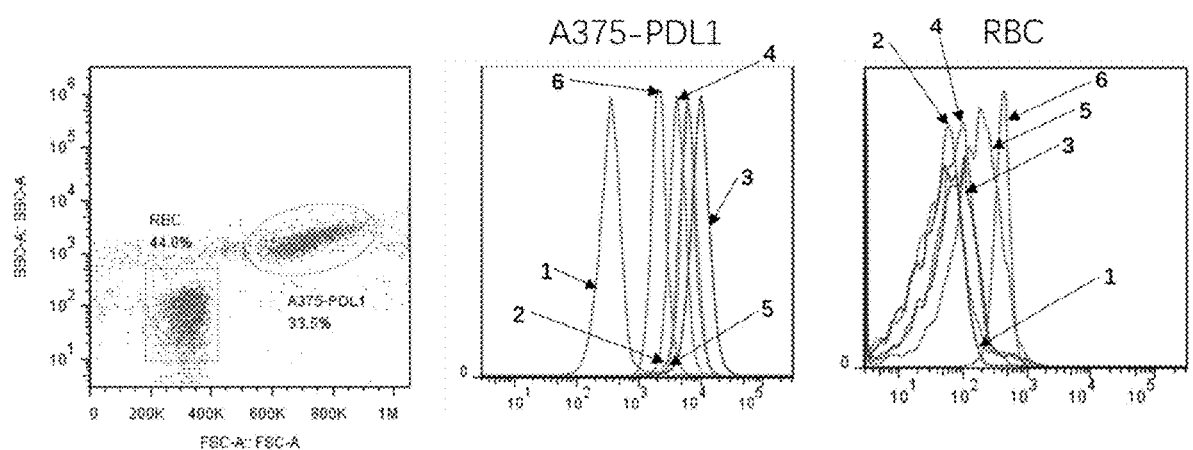

The results are shown in FIG. 6b. In FIG. 6b, serial number of 1, 2, 3, 4, 5 and 6 correspond to isotype control (human IgG1), hu56di-SIRPα, ate-SIRPα, hu56-Fc6-SIRPα, SIRPα-Fc IgG1 and AB6.12 IgG1, respectively. It was found that hu56di-SIRPα, ate-SIRPα and hu56-Fc6-SIRPα exhibits stronger binding to tumor cells than AB6.12 IgG1. Besides, hu56di-SIRPα, ate-SIRPα and hu56-Fc6-SIRPα almost do not bind to RBC. In comparison, SIRPα-Fc IgG1 bind to RBC and AB6.12 IgG1 exhibiting strong binding to RBC.

Similarly, MCF7 tumor cells were mixed with a 15-fold excess of RBCs, and then incubated with 20 μg/ml Tmab-SIRPα, SIRPα-Fc IgG1, AB6.12 IgG1 or isotype control (human IgG1) at 4° C. for 30 min. Then the cells were washed to remove unbound proteins and incubated with an anti-hIgG Fc gamma specific PE antibody at 4° C. for 20 min. The cells were analyzed by flow cytometry (Life Technology). The gate of erythrocytes was assessed by anti-human CD235a (eBiosciences Cat #12-9987-80).

Similarly, T47D tumor cells were mixed with a 15-fold excess of RBCs, and then incubated with 20 μg/ml 5E5-SIRPα, SIRPα-Fc IgG1, AB6.12 IgG1 or isotype control (human IgG1) at 4° C. for 30 min. Then the cells were washed to remove unbound proteins and incubated with an anti-hIgG Fc gamma specific PE antibody at 4° C. for 20 min. The cells were analyzed by flow cytometry (Life Technology). The gate of erythrocytes was assessed by anti-human CD235a (eBiosciences Cat #12-9987-80).

Similarly, U87 tumor cells were mixed with a 15-fold excess of RBCs, and then incubated with 20 μg/ml mAb806-SIRPα, SIRPα-Fc IgG1, AB6.12 IgG1 or isotype control (human IgG1) at 4° C. for 30 min. Then the cells were washed to remove unbound proteins and incubated with an anti-hIgG Fc gamma specific PE antibody at 4° C. for 20 min. The cells were analyzed by flow cytometry (Life Technology). The gate of erythrocytes was assessed by anti-human CD235a (eBiosciences Cat #12-9987-80).

Figures 6C, 6D:
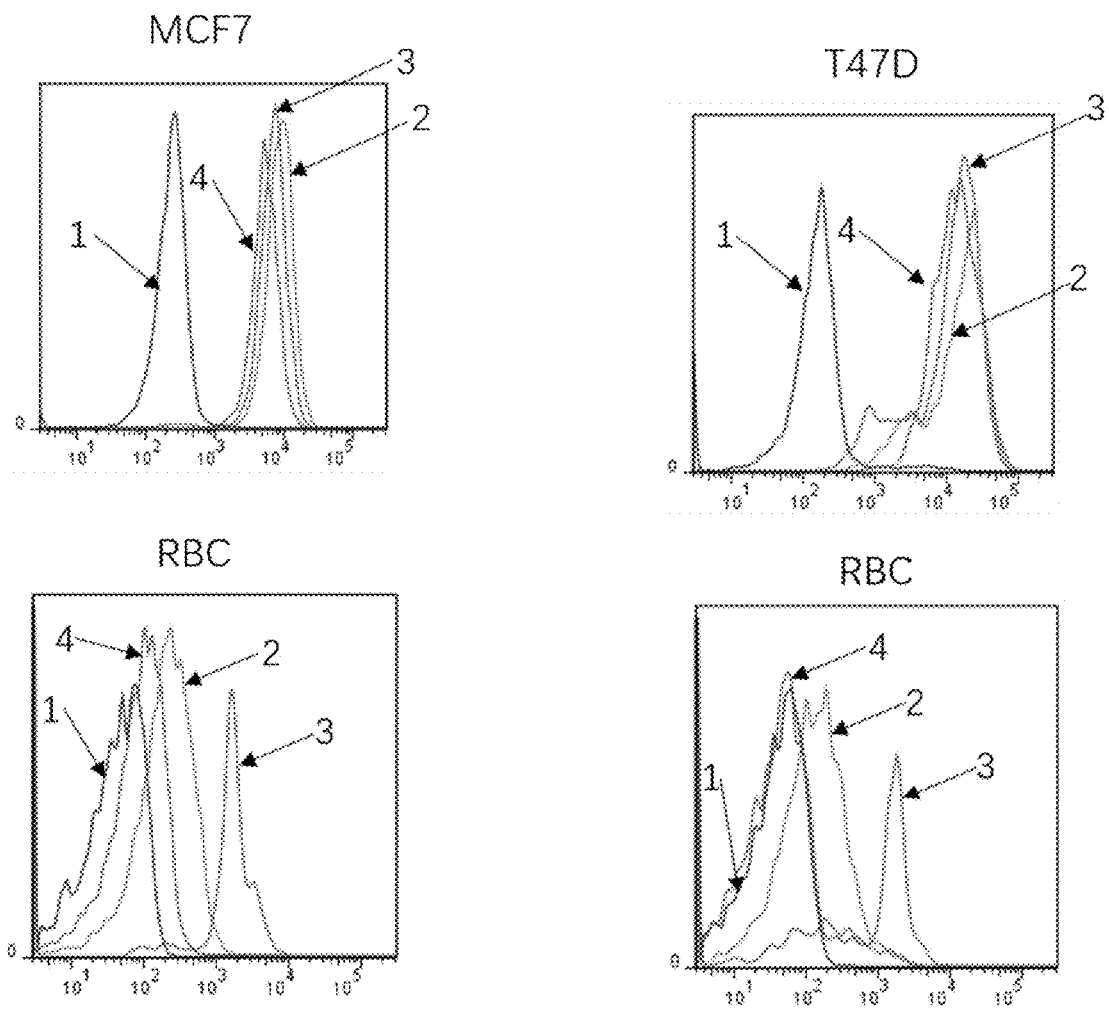

The results are shown in FIG. 6c-6e. In FIG. 6c, serial number of 1, 2, 3 and 4 correspond to isotype control (human IgG1), SIRPα-Fc IgG1, AB6.12 IgG1, and Tmab-SIRPα, respectively. FIG. 6c shows the binding of isotype control (human IgG1), SIRPα-Fc IgG1, AB6.12 IgG1. and Tmab-SIRPα to MCF7 tumor cells and RBC. In FIG. 6d, serial numbers of 1, 2, 3 and 4 correspond to isotype control (human IgG1), SIRPα-Fc IgG1, AB6.12 IgG1., and 5E5-SIRPα, respectively. FIG. 6d shows the binding of isotype control (human IgG1), SIRPα-Fc IgG1, AB6.12 IgG1., and 5E5-SIRPα to T47D tumor cells and RBC. In FIG. 6e, serial number of 1, 2, 3 and 4 correspond to isotype control (human IgG1), SIRPα-Fc IgG1, AB6.12 IgG1. and mAb806-SIRPα. FIG. 6e shows the binding of isotype control (human IgG1), SIRPα-Fc IgG1, AB6.12 IgG1. and mAb806-SIRPα. It was found that the three heterodimers of Tmab-SIRPα, 5E5-SIRPα and mAb806-SIRPα almost do not bind to RBC, and their binding to corresponding tumor cells is comparable to SIRPα-Fc IgG1 and AB6.12 IgG1.

Similarly, fresh RBC cell was diluted 2500 times, then it was incubated with 20 μg ml$^{-1}$ isotype control (human IgG1), hu56di-SIRPα, hu56di-CV1, SIRPα-Fc IgG1 and AB6.12 IgG1, respectively. The results were shown in FIG. 6f, in which serial numbers of 1, 2, 3, 4 and 5 correspond to isotype control, hu56di-SIRPα, hu56di-CV1, SIRPα-Fc IgG1 and AB6.12 IgG1. FIG. 6f shows that hu56di-CV1 exhibits stronger binding to RBC than hu56di-SIRPα, hu56di-CV1 exhibits comparable binding to RBC with AB6.12 IgG1, and SIRPα-Fc IgG1 exhibits weaker binding to RBC than hu56di-CV1 and AB6.12 IgG1. Thus, it can be inferred that hu56di-SIRPα exhibits better safety than hu56di-CV1, SIRPα-Fc IgG1 and AB6.12 IgG1.

Figure 6G:
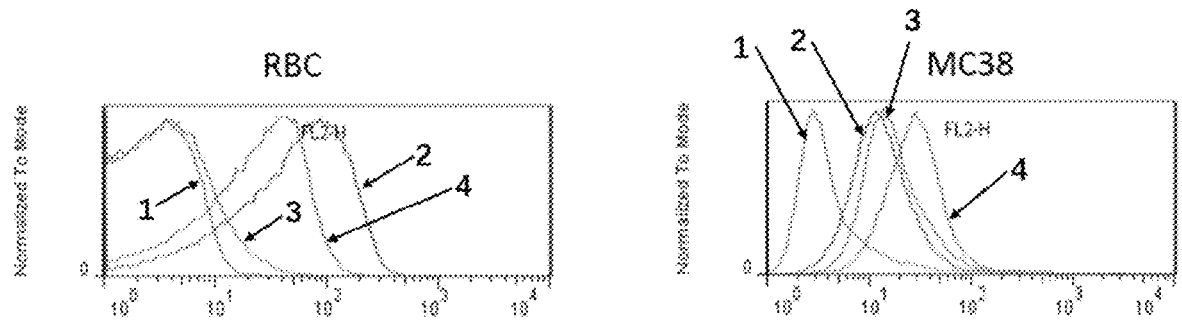
Figure 6H:
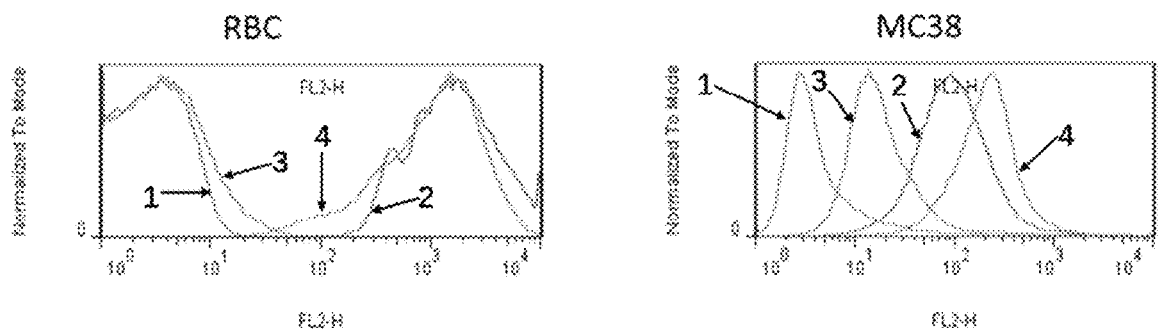

Similarly, MC38 tumor cells were mixed with a 15-fold excess of mouse RBCs, and then incubated with 20 μg/ml, a-mPD-L1, mSIRPα-Fc, CV1-Fc, mPD-L1-CV1, mPD-L1-mSIRPα or isotype control (human IgG1) at 4° C. for 30 min. Then the cells were washed to remove unbound proteins and incubated with an anti-hIgG Fc gamma specific PE antibody at 4° C. for 20 min. The cells were analyzed by flow cytometry (Life Technology). The gate of erythrocytes was assessed by anti-mouse RBC antibody (abcam Cat #ab106101). The results are shown in FIG. 6g and FIG. 6h. In FIG. 6g, serial numbers of 1, 2, 3 and 4 correspond to isotype control (human IgG1), mSIRPα-Fc, a-mPD-L1 and mPD-L1-mSIRPα. In FIG. 6h, serial numbers of 1, 2, 3 and 4 correspond to isotype control (human IgG1), CV1-Fc, a-mPD-L1 and mPD-L1-CV1. FIG. 6g and FIG. 6h show that mPD-L1-CV1 exhibits stronger binding to RBC than mPD-L1-mSIRPα, mPD-L1-CV1 exhibits comparable binding to RBC with CV1-Fc, and mSIRPα-Fc exhibits weaker binding to RBC than mPD-L1-CV1. Thus, it can be inferred that mPD-L1-mSIRPα exhibits better safety than mPD-L1-CV1 and mSIRPα-Fc.

Example 9 Platelets Binding of the Immunoconjugate of the Present Disclosure

Platelets also express CD47 as self-antigen to prevent phagocytosis of macrophage. It has been reported that SIRPα-Fc induced thrombocytopenia after being injected into human. Hence, platelets binding of hu56di-SIRPα was examined using flow cytometry. Platelets were separated from fresh blood by centrifugation. Firstly, fresh blood was centrifuged at 200 g for 10 min to get platelet-rich plasma (PRP), then PRP was centrifuged at 1800 g for 10 min to get platelets. The platelets were incubated with 20 µg/ml of hu56di-SIRPα, SIRPα-Fc IgG1 or AB6.12 IgG1 or isotype control (human IgG1) at 4° C. for 30 min. Then, the platelets were washed to remove unbound proteins and incubated with an anti-hIgG Fc APC antibody at 4° C. for 20 min. The platelets were then incubated with anti-human CD42b PE antibody at 4° C. for 20 min. The platelets were analyzed by flow cytometry (Life Technology). The gate of platelets was assessed by anti-human CD42b (Biolegend Cat #303906). The median fluorescence intensity (MFI) of APC in CD42b-positive population indicated drug binding with platelets.

Figure 7:
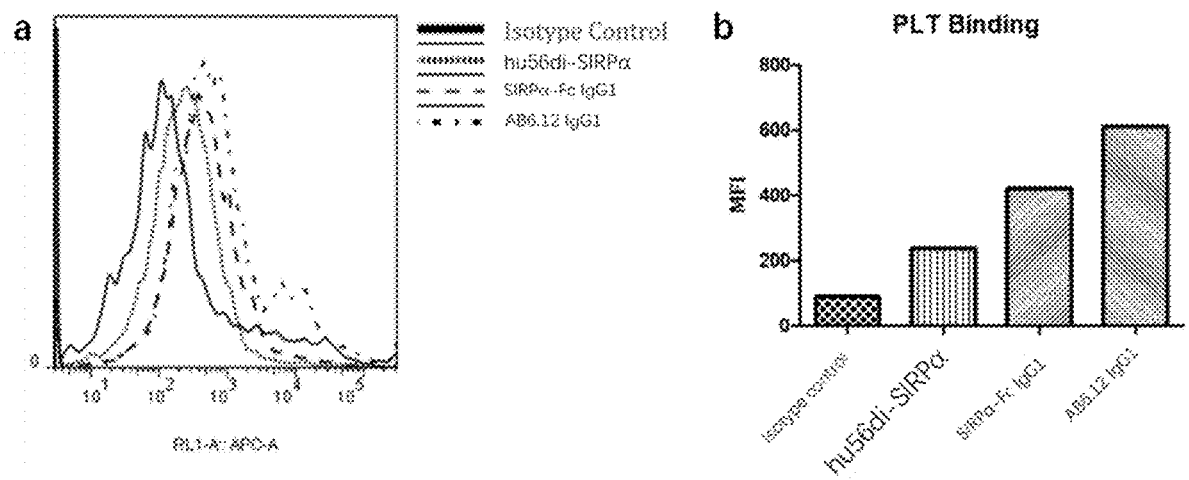
FIGS. 7a-7b illustrate the platelets binding result of the immunoconjugate of the present disclosure.

The results are shown in FIG. 7. In FIG. 7a, the horizontal coordinate is the concentration of hu56di-SIRPα, SIRPα-Fc IgG1, AB6.12 IgG1 or the isotype control, and the vertical coordinate shows the MFI value. The quantified results are shown in FIG. 7b. As can be seen from FIG. 7, the binding of hu56di-SIRPα with the platelets was much lower than that of SIRPα-Fc IgG1 and AB6.12 IgG1.

Example 10 In Vivo Anti-Tumor Efficacy and Safety

The CD47 binding site on SIRPα is located in the IgV loop domain. The extracellular IgV domain is relatively well conserved (>75%) in both mouse and human SIRPα, but the binding to CD47 is species specific. Human SIRPα bound strongly to CD47 of NOD mice, but did not bind to CD47 of C57BL/6 mice. Hence, a mPD-L1-mSIRPα was constructed to evaluate anti-tumor efficacy in MC38 syngeneic model.

Figure 8A:
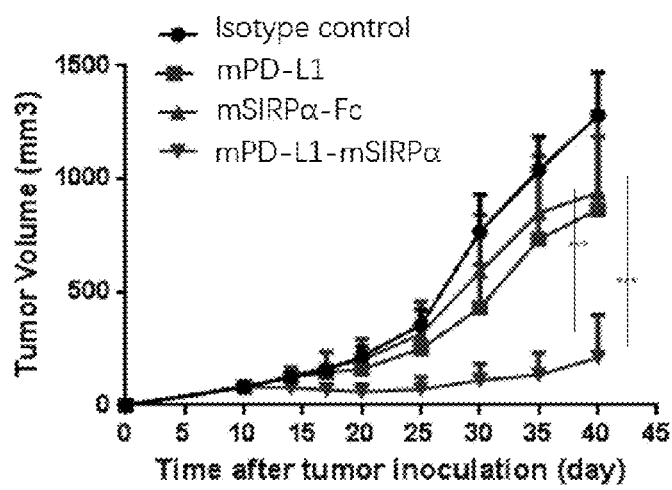
FIGS. 8a-8i illustrate the in vivo anti-tumor efficacy and safety of the immunoconjugate of the present disclosure.
Figure 8B:
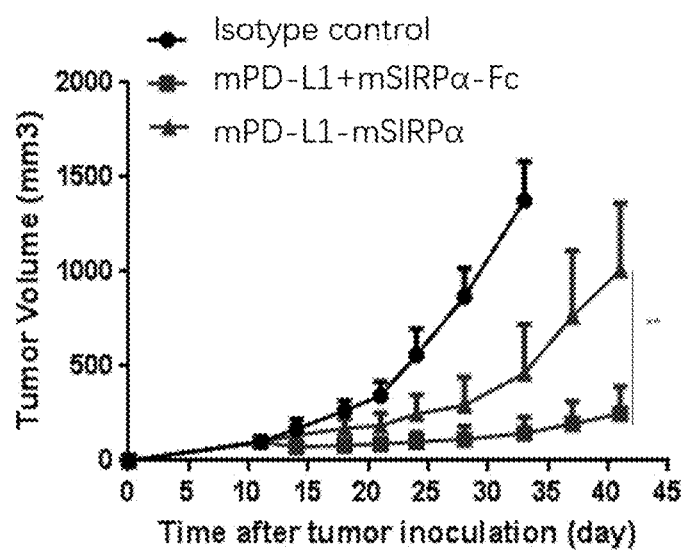
Figure 8C:
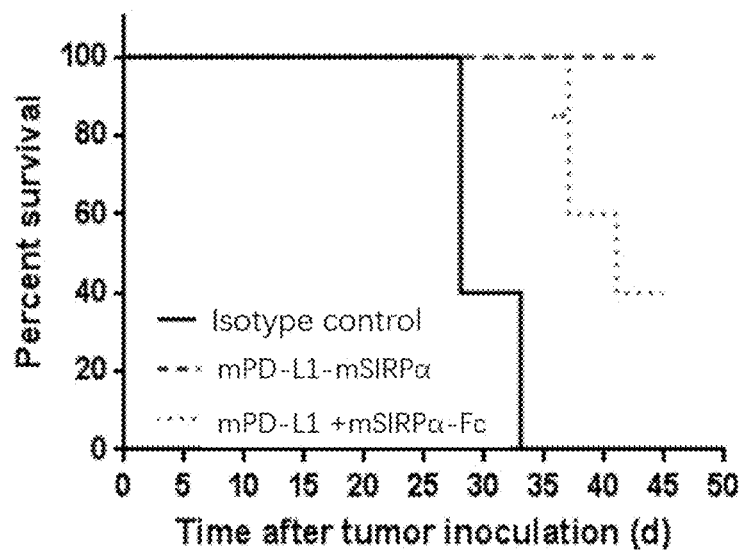
Figure 8D:
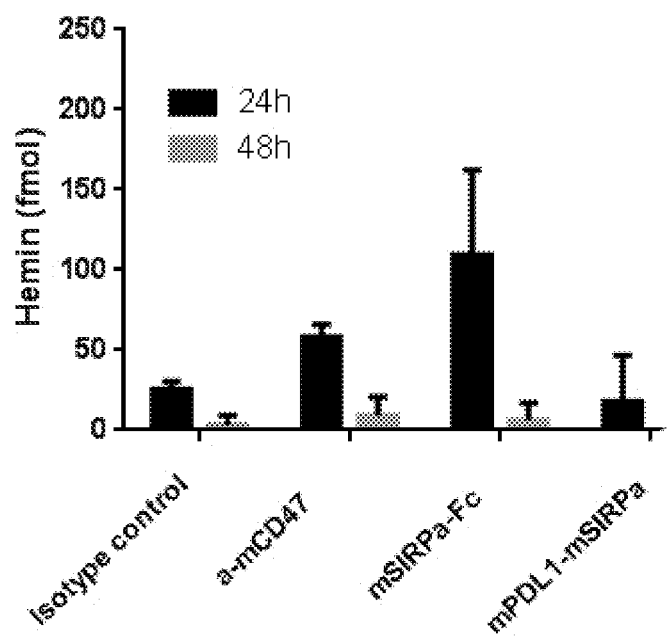

The results are shown in FIGS. 8a-8d. The horizontal coordinate is the time after tumor inoculation, and the vertical coordinate is the value of tumor volume (FIG. 8a and FIG. 8b), the percentage of survival (FIG. 8c), and the fmol of Hemin (FIG. 8d). C57BL/6 mice were inoculated with MC38 tumor cells. When tumors were well established, human IgG isotype control, a-mPD-L1, mSIRPα-Fc or mPD-L1-mSIRPα was intratumorally administered and tumor growth was monitored. Comparing to the isotype control (hIgG1), the mPD-L1 antibody, and the mSIRPα-Fc, mPD-L1-mSIRPα significantly inhibited tumor growth (FIG. 8a).

For clinical administration, to evaluate whether systemic treatment with mPD-L1-mSIRPα could inhibit tumor growth, isotype control, mPD-L1-mSIRPα and a mixture of a-mPD-L1 antibody with mSIRPα-Fc was intraperitoneally administered into established tumor-bearing mice and tumor growth was monitored. Comparing to human IgG isotype control and the mixture of mPD-L1 antibody with mSIRPα-Fc, systemic mPD-L1-mSIRPα treatment consistently and significantly slowed tumor growth and prolonged the survival of tumor-bearing mice (FIGS. 8b and 8c). To determine whether or not mPD-L1-mSIRPα could selectively bind to tumor cells while protecting RBC in vivo, hemin in serum of tumor-bearing mice treated with human IgG isotype control, a-mCD47, mSIRPα-Fc or mPD-L1-mSIRPα was measured. Comparing to a-mCD47 and mSIRPα-Fc treatment, mPD-L1-mSIRPα protected RBC from immune lysis (FIG. 8d).

Similarly, mPD-L1-mCD47, mPD-L1-mSIRPα and mPD-L1-CV1 were constructed to evaluate anti-tumor efficacy in MC38 syngeneic model.

Figure 8E:
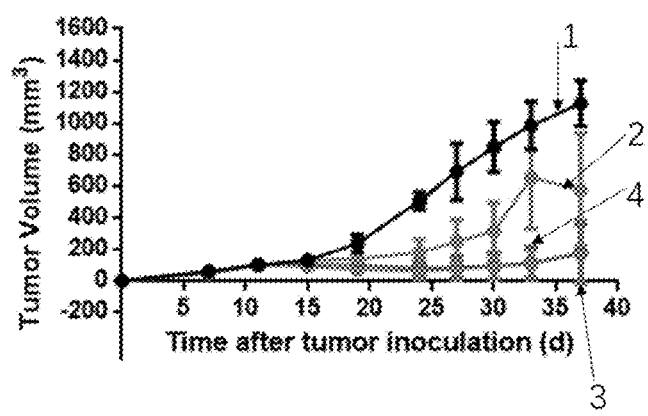
Figure 8F:
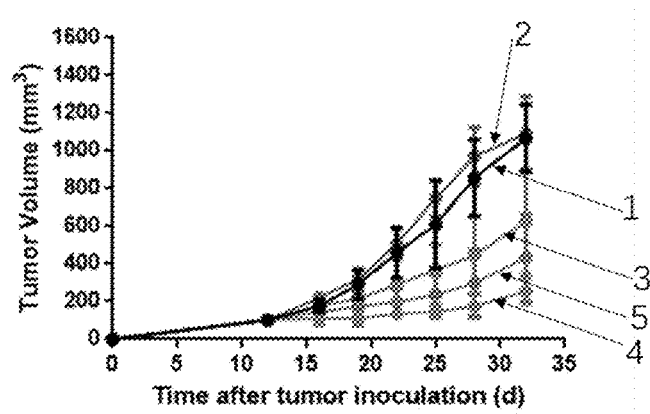
Figure 8G:
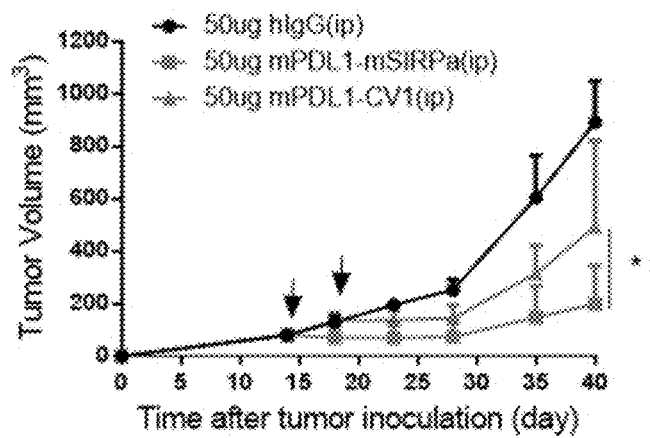

In FIG. 8e, serial number 1, 2, 3 and 4 correspond to isotype control (hIgG1), mPD-L1-mCD47, mPD-L1-mSIRPα and mPD-L1-CV1. In FIG. 8f, serial number 1, 2, 3, 4 and 5 correspond to untreated sample, isotype control (hIgG1), mPD-L1-mCD47, mPD-L1-mSIRPα and mPD-L1-CV1. FIG. 8e and FIG. 8f show that mPD-L1-mSIRPα and mPD-L1-CV1 exhibit no therapeutic difference in big dose since small but enough mPD-L1-CV1 can reach tumor and bind with tumor cells with higher affinity although mPD-L1-CV1 has a higher binding with RBCs. FIG. 8g shows that mPD-L1-mSIRPα is better than mPD-L1-CV1 in small dose since mPD-L1-CV1 cannot reach tumor due to its higher binding with RBCs.

Figure 8H:
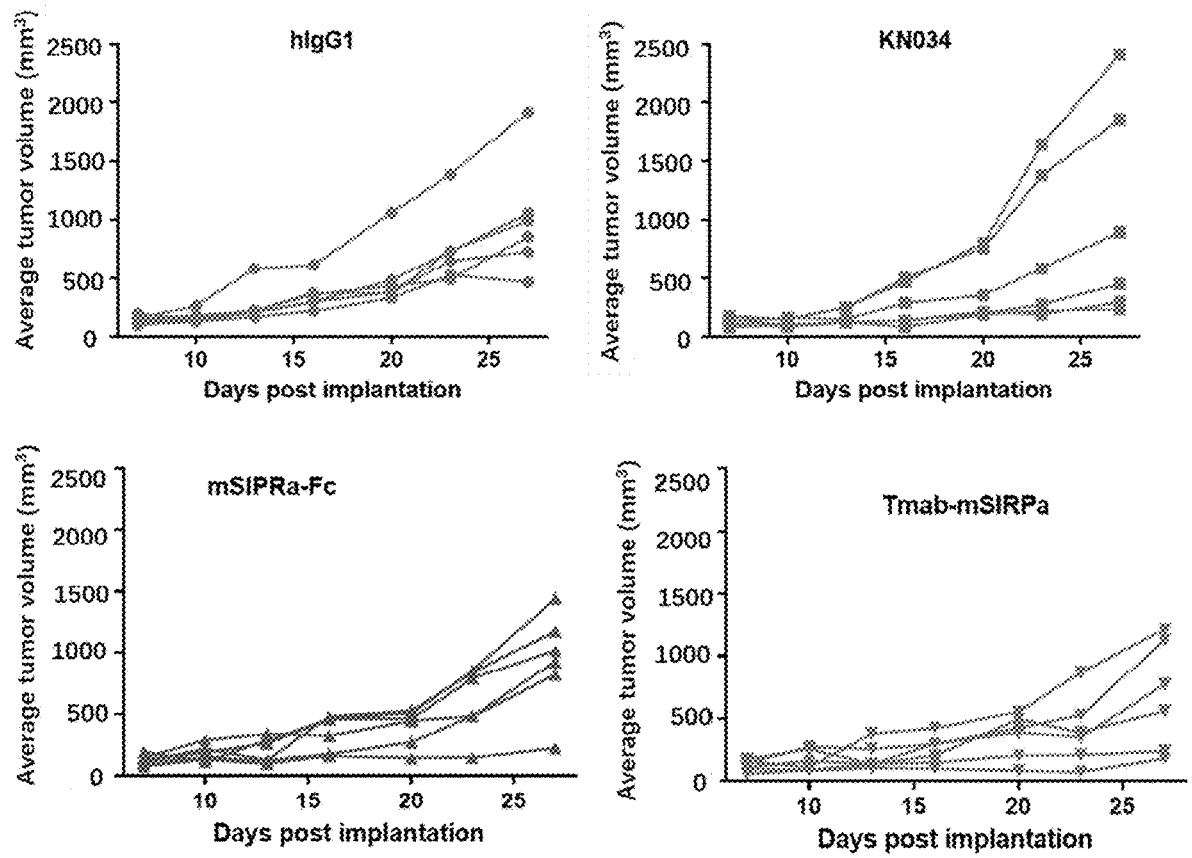
Figure 8I:
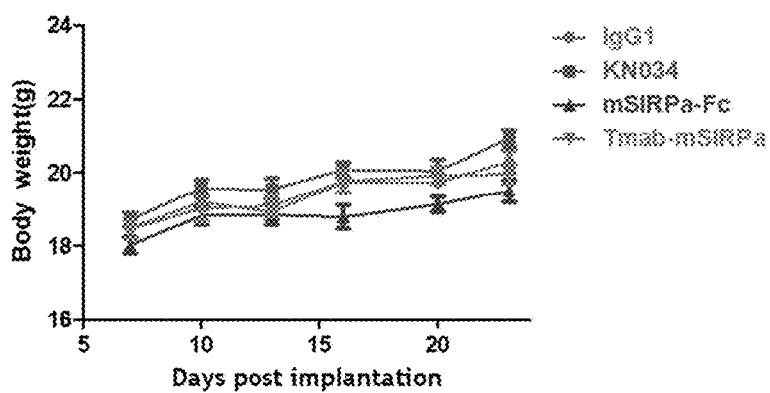

Similarly, Tmab-mSIRPα, mSIRPα-Fc, IgG1 Isotype and KN034 (Herceptin) were constructed to evaluate anti-tumor efficacy in MC38-HER2 syngeneic model with C57BL/6 mouse. Table 7 provides the specific treatment information for above-mentioned drugs. FIG. 8h shows that Tmab-mSIRPα inhibited tumor growth obviously better than mSIRPα-Fc, IgG1 Isotype and KN034 (Herceptin). FIG. 8i shows the body weight of the mice after tumor implantation.

TABLE 7

| Treatment | Dose (mg/kg) | Dosing Route | Schedule |
| --- | --- | --- | --- |
| IgG1 isotype | 6.55 | i.p | BIW × 3 dose |
| KN034 (Herceptin) | 6.55 | i.p | BIW × 3 dose |
| mSIRPα-Fc | 3.55 | i.p | BIW × 3 dose |
| Tmab-mSIRPα | 5 | i.p | BIW × 3 dose |

Example 11 Combination with Chemotherapy

Further, potential synergistic effects of the immunoconjugate of the present disclosure with chemotherapy were tested.

Figure 9:
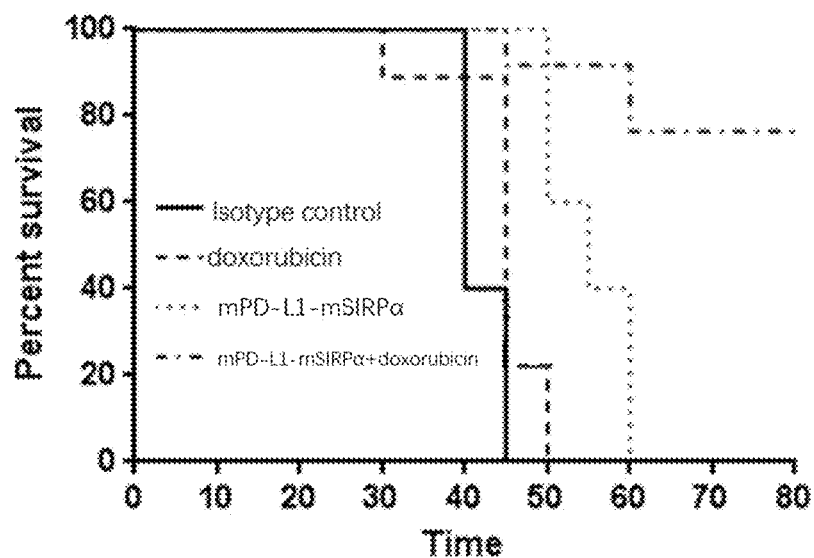
FIG. 9 illustrate the effect of the immunoconjugate of the present disclosure when used in combination with a chemotherapy.

Then, the effects of mPD-L1-mSIRPα in combination with doxorubicin were examined. As shown in FIG. 9, the horizontal coordinate is the day after the treatment, and the vertical coordinate is the percentage of survival of the mice after the treatment. C57BL/6 mice was inoculated with MC38 tumor cells, 11 days later, doxorubicin was administered intratumorally, and mPD-L1-mSIRPα was administered 1 day later. Comparing to the isotype control, doxorubicin alone, or mPD-L1-mSIRPα alone, the combination of doxorubicin with mPD-L1-mSIRPα further significantly inhibited tumor growth and prolonged survival of tumor-bearing mice (FIG. 9).

Example 12 In Vivo Anti-Tumor Efficacy in Humanized Mouse Models

In vivo anti-tumor efficacies of the immunoconjugate of the present disclosure were also tested in humanized mouse models.

Figure 10:
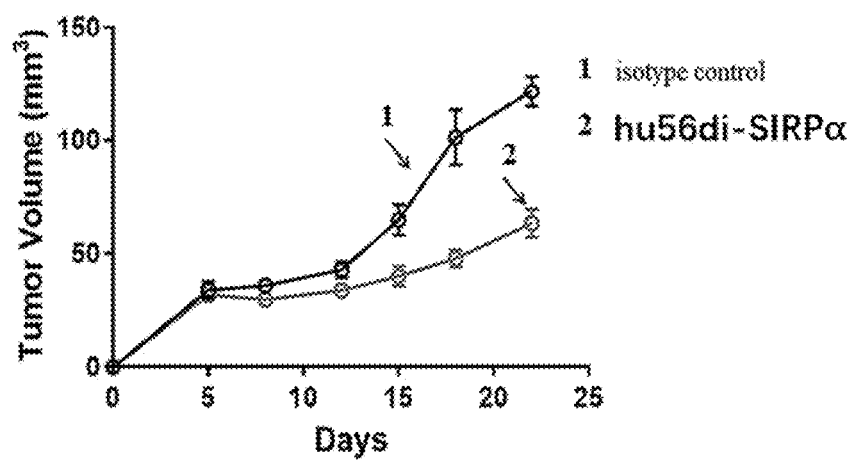
FIG. 10 illustrates the in vivo effect of the immunoconjugate of the present disclosure.

Humanized NSG-SGM3 mice were obtained from Jackson Lab, female, 3 wks old. Tumor implant was performed by 12 wks of age. The humanized NSG-SGM3 mice were respectively inoculated with 2×10⁶ MDA-MB-231 tumor cells i.v. on day 0. Then, starting from day 5, 5 doses of the hu56di-SIRPα or isotype control (human IgG1) were administrated to the tumor-bearing humanized NSG-SGM3 mice respectively (for each agent, two doses were administered per week). Then, tumor volume was measured, and the results are shown in FIG. 10. FIG. 10 shows the tumor volume of humanized NSG-SGM3 mice after being administrated with hu56di-SIRPα or isotype control. In FIG. 10, the horizontal ordinate is the days after inoculation, while the vertical ordinate is the tumor volume. These results demonstrate that the immunoconjugate of the present disclosure effectively inhibits tumor growth in vivo.

The effects of the other immunoconjugates (e.g., Tmab-SIRPα, Pmab-SIRPα, Mab806-SIRPα, 5E5-SIRPα, hu56-Fc6-SIRPα, ate-SIRPα, ave-SIRPα and dur-SIRPα) of the present disclosure were also tested, and similar results were observed.

While preferred embodiments of the present application have been shown and described herein, it will be obvious to those skilled in the art that such embodiments are provided by way of example only. It is not intended that the application be limited by the specific examples provided within the specification. While the application has been described with reference to the aforementioned specification, the descriptions and illustrations of the embodiments herein are not meant to be construed in a limiting sense. Numerous variations, changes, and substitutions will now occur to those skilled in the art without departing from the application. Furthermore, it shall be understood that all aspects of the application are not limited to the specific depictions, configurations or relative proportions set forth herein which depend upon a variety of conditions and variables. It should be understood that various alternatives to the embodiments of the application described herein may be employed in practicing the application. It is therefore contemplated that the application shall also cover any such alternatives, modifications, variations or equivalents. It is intended that the following claims define the scope of the application and that methods and structures within the scope of these claims and their equivalents be covered thereby.

What is claimed is:

1. An immunoconjugate, which is a proteinaceous heterodimer consisting of a first member and a second member, said first member, called the first Fc subunit, comprises a targeting moiety fused to the first subunit of the human IgG Fc domain, and said second member, called the second Fc subunit, comprises a single copy of a signal regulatory protein α, or SIRPα, fused to the second subunit of the human IgG Fc domain, wherein said first Fc subunit associates with said second Fc subunit to form said proteinaceous heterodimer and wherein said first Fc subunit comprises a first modification, and the second Fc subunit comprises a second modification, and the first modification and the second modification consist of substitution mutations selected from any one of the following groups;
1) the first modification: Y349C and T366W; and the second modification: D356C, T366S, L368A, Y407V and F405K;
2) the first modification: Y349C, T366W, and F405K; and the second modification: D356C, T366S, L368A and Y407V;
3) the first modification: Y349C, T366W and K409E; and the second modification: D356C, T366S, L368A, Y407V and F405K;
4) the first modification: Y349C, T366W and K409A; and the second modification: D356C, T366S, L368A, Y407V and F405K;
5) the first modification: Y349C, T366W, F405K, K360E and Q347E; and the second modification: D356C, T366S, L368A, Y407V and Q347R;
6) the first modification: Y349C, T366W, F405K and Q347R; and the second modification: D356C, T366S, L368A, Y407V, K360E and Q347E;
7) the first modification: Y349C, T366W, K409A, K360E and Q347E; and the second modification: D356C, T366S, L368A, Y407V, F405K and Q347R;
8) the first modification: Y349C, T366W, K409A and Q347R; and the second modification: D356C, T366S, L368A, Y407V, F405K, K360E and Q347E;
9) the first modification: T366W, K409A and K392D; and the second modification: T366S, L368A, Y407V, D399S and F405K;
10) the first modification: T366W and K409A; and the second modification: T366S, L368G, Y407A and F405K;
11) the first modification: T366W, K409A and Y349D; and the second modification: T366S, L368A, Y407V, F405K and E357A;
12) the first modification: T366W, K409A, Y349D and S354D; and the second modification: T366S, L368A, Y407V, F405K and E357A;
13) the first modification: T366W and F405K; and the second modification: T366S, L368A, Y407V and K409A;
14) the first modification: T366W, F405K and D399S; and the second modification: T366S, L368A, Y407V, K409A and K392D;
15) the first modification: T366W and F405K; and the second modification: T366S, L368G, Y407A and K409A;
16) the first modification: T366W, F405K and Y349D; and the second modification: T366S, L368A, Y407V, K409A and E357A;
17) the first modification: T366W, F405K, Y349D and S354D; and the second modification: T366S, L368A, Y407V, K409A and E357A;
wherein the position of the amino acid is determined according to the EU index of the KABAT number; and wherein said Fc domain is a human IgG Fc domain;
wherein said targeting moiety comprises an antigen-binding domain of an anti-PD-L1 antibody, and said SIRPα has an amino acid sequence as set forth in SEQ ID NO: 122 or 123.

2. The immunoconjugate according to claim 1, wherein said single copy of SIRPα is directly or indirectly fused to said second Fc subunit comprising said second modification.

3. The immunoconjugate according to claim 1, wherein said anti-PD-L1 antibody is selected from the group consisting of Atezolizumab, Avelumab, Durvalumab, KN035 and hu56.

4. The immunoconjugate according to claim 1, wherein said targeting moiety is directly or indirectly fused to the amino-terminal amino acid of one of the two subunits of the Fc domain, and said single copy of SIRPα is directly or indirectly fused to the amino-terminal amino acid of the other one of the two subunits of the Fc domain.

5. The immunoconjugate according to claim 4, wherein the immunoconjugate comprises two of said targeting moiety, which are a first targeting moiety and a second targeting moiety.

6. The immunoconjugate according to claim 5, wherein said first targeting moiety is directly or indirectly fused to one of said two subunits of the Fc domain, and said second targeting moiety is directly or indirectly fused to the other one of said two subunits of the Fc domain.

7. The immunoconjugate according to claim 5, which is a proteinaceous heterodimer comprising a first member and a second member different from said first member, wherein:
said first member comprises said first targeting moiety fused to one of the two subunits of the Fc domain;
said second member comprises said single copy of SIRPα, said second targeting moiety and the other one of the two subunits of the Fc domain, with said single copy of SIRPα fused to one terminal of the Fc subunit and said second targeting moiety fused to the other terminal of the Fc subunit; and
said first Fc subunit associates with said second Fc subunit to form said heterodimer.

8. The immunoconjugate according to claim 5, wherein said first targeting moiety is directly or indirectly fused to the amino-terminal amino acid of one of the two subunits of the Fc domain, said second targeting moiety is directly or indirectly fused to the amino-terminal amino acid of the other one of the two subunits of the Fc domain, and said single copy of SIRPα is directly or indirectly fused to the carboxy-terminal amino acid of the first or the second Fc subunit.

9. An isolated nucleic acid or isolated nucleic acids encoding the immunoconjugate according to claim 1.

10. A vector or vectors comprising the isolated nucleic acid or isolated nucleic acids according to claim 9.

11. An isolated host cell comprising the isolated nucleic acid or isolated nucleic acids according to claim 9 or the vector or vectors according to claim 10.

12. A method for producing an immunoconjugate according to claim 1, comprising (i) culturing the host cell of claim 11 under conditions to effect expression and formation of the immunoconjugate, and (ii) harvesting the immunoconjugate formed.

13. A pharmaceutical composition comprising an effective amount of an immunoconjugate according to claim 1, and optionally a pharmaceutically acceptable excipient.

14. The pharmaceutical composition according to claim 13, further comprising an effective amount of an additional therapeutically active component for cancer treatment, wherein said additional therapeutically active component is cytotoxic agent for chemotherapy.

15. The pharmaceutical composition according to claim 14, wherein said cytotoxic agent is doxorubicin.

16. A method of treating cancer, comprising administrating the immunoconjugate according to claim 1 in combination with the additional therapeutically active component as defined in claim 14 to a subject in need thereof.

17. The method according to claim 16, wherein said cancer is selected from the group consisting of: breast cancer, melanoma, and colon cancer.

18. A method for producing an immunoconjugate according to claim 1, comprising (i) culturing a host cell comprising a vector or vectors comprising an isolated nucleic acid or isolated nucleic acids encoding the immunoconjugate under conditions to effect expression and formation of the immunoconjugate, and (ii) harvesting the immunoconjugate formed.

* * * * *

SEQUENCE LISTING

```
<160> NUMBER OF SEQ ID NOS: 167

<210> SEQ ID NO 1
<211> LENGTH: 227
<212> TYPE: PRT
<213> ORGANISM: Artificial Sequence
<220> FEATURE:
<223> OTHER INFORMATION: Y349C+T366W

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 2
<211> LENGTH: 227
<212> TYPE: PRT
<213> ORGANISM: Artificial Sequence
<220> FEATURE:
<223> OTHER INFORMATION: D356C+T366S+L368A+Y407V+F405K

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Cys Glu Leu Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 3
<211> LENGTH: 227
<212> TYPE: PRT
<213> ORGANISM: Artificial Sequence
<220> FEATURE:
<223> OTHER INFORMATION: Y349C+T366W+F405K

<400> SEQUENCE: 3

Asp Lys Thr His Thr Cys Pro Pro Cys Pro Ala Pro Glu Leu Leu Gly

-continued

```
                1               5                      10                      15
        Gly Pro Ser Val Phe Leu Phe Pro Pro Lys Pro Lys Asp Thr Leu Met
                        20                      25                      30

Ile Ser Arg Thr Pro Glu Val Thr Cys Val Val Val Asp Val Ser His
                        35                      40                      45

Glu Asn Pro Glu Val Lys Phe Asn Trp Tyr Val Asp Gly Val Glu Val
         50                      55                      60

His Asn Ala Lys Thr Lys Pro Arg Glu Glu Gln Tyr Asn Ser Thr Tyr
         65                      70                      75                      80

Arg Val Val Ser Val Leu Thr Val Leu His Gln Asp Trp Leu Asn Gly
                        85                      90                      95

Lys Glu Tyr Lys Cys Lys Val Ser Asn Lys Ala Leu Pro Ala Pro Ile
                        100                     105                     110

Glu Lys Thr Ile Ser Lys Ala Lys Gly Gln Pro Arg Glu Pro Gln Val
                        115                     120                     125

Cys Thr Leu Pro Pro Ser Arg Asp Glu Leu Thr Lys Asn Gln Val Ser
                        130                     135                     140

Leu Trp Cys Leu Val Lys Gly Phe Tyr Pro Ser Asp Ile Ala Val Glu
        145                     150                     155                     160

Trp Glu Ser Asn Gly Gln Pro Glu Asn Asn Tyr Lys Thr Thr Pro Pro
                        165                     170                     175

Val Leu Asp Ser Asp Gly Ser Phe Lys Leu Tyr Ser Lys Leu Thr Val
                        180                     185                     190

Asp Lys Ser Arg Trp Gln Gln Gly Asn Val Phe Ser Cys Ser Val Met
                        195                     200                     205

His Glu Ala Leu His Asn His Tyr Thr Gln Lys Ser Leu Ser Leu Ser
                        210                     215                     220

Pro Gly Lys
        225

<210> SEQ ID NO 4
        <211> LENGTH: 227
        <212> TYPE: PRT
        <213> ORGANISM: Artificial Sequence
        <220> FEATURE:
        <223> OTHER INFORMATION: D356C+T366S+L368A+Y407V

<400> SEQUENCE: 4

Asp Lys Thr His Thr Cys Pro Pro Cys Pro Ala Pro Glu Leu Leu Gly
        1               5                       10                      15

Gly Pro Ser Val Phe Leu Phe Pro Pro Lys Pro Lys Asp Thr Leu Met
                        20                      25                      30

Ile Ser Arg Thr Pro Glu Val Thr Cys Val Val Val Asp Val Ser His
                        35                      40                      45

Glu Asp Pro Glu Val Lys Phe Asn Trp Tyr Val Asp Gly Val Glu Val
         50                      55                      60

His Asn Ala Lys Thr Lys Pro Arg Glu Glu Gln Tyr Asn Ser Thr Tyr
         65                      70                      75                      80

Arg Val Val Ser Val Leu Thr Val Leu His Gln Asp Trp Leu Asn Gly
                        85                      90                      95

Lys Glu Tyr Lys Cys Lys Val Ser Asn Lys Ala Leu Pro Ala Pro Ile
                        100                     105                     110

Glu Lys Thr Ile Ser Lys Ala Lys Gly Gln Pro Arg Glu Pro Gln Val
                        115                     120                     125

Tyr Thr Leu Pro Pro Ser Arg Cys Glu Leu Thr Lys Asn Gln Val Ser
```

```
                130                 135                 140
Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 227
<212> TYPE: PRT
<213> ORGANISM: Artificial Sequence
<220> FEATURE:
<223> OTHER INFORMATION: Y349C+T366W+K409E

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Glu Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 6
<211> LENGTH: 227
<212> TYPE: PRT
```

<213> ORGANISM: Artificial Sequence
<220> FEATURE:
<223> OTHER INFORMATION: Y349C+T366W+K409A

<400> SEQUENCE: 6

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 7
<211> LENGTH: 227
<212> TYPE: PRT
<213> ORGANISM: Artificial Sequence
<220> FEATURE:
<223> OTHER INFORMATION: Y349C+T366W+F405K+K360E+Q347E

<400> SEQUENCE: 7

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Glu Val
        115                 120                 125
Cys Thr Leu Pro Pro Ser Arg Asp Glu Leu Thr Glu Asn Gln Val Ser
    130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Lys Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 8
<211> LENGTH: 227
<212> TYPE: PRT
<213> ORGANISM: Artificial Sequence
<220> FEATURE:
<223> OTHER INFORMATION: D356C+T366S+L368A+Y407V+Q347R

<400> SEQUENCE: 8

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Arg Val
        115                 120                 125
Tyr Thr Leu Pro Pro Ser Arg Cys Glu Leu Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
```

Pro Gly Lys
225

<210> SEQ ID NO 9
<211> LENGTH: 227
<212> TYPE: PRT
<213> ORGANISM: Artificial Sequence
<220> FEATURE:
<223> OTHER INFORMATION: Y349C+T366W+F405K+Q347R

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
        115                 120                 125

Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 10
<211> LENGTH: 227
<212> TYPE: PRT
<213> ORGANISM: Artificial Sequence
<220> FEATURE:
<223> OTHER INFORMATION: D356C+T366S+L368A+Y407V+K360E+Q347E

<400> SEQUENCE: 10

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Tyr Thr Leu Pro Pro Ser Arg Cys Glu Leu Thr Glu Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 11
<211> LENGTH: 227
<212> TYPE: PRT
<213> ORGANISM: Artificial Sequence
<220> FEATURE:
<223> OTHER INFORMATION: Y349C+T366W+K409A+K360E+Q347E

<400> SEQUENCE: 11

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Cys Thr Leu Pro Pro Ser Arg Asp Glu Leu Thr Glu Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly Lys
225

<210> SEQ ID NO 12
<211> LENGTH: 227
<212> TYPE: PRT
<213> ORGANISM: Artificial Sequence
<220> FEATURE:
<223> OTHER INFORMATION: D356C+T366S+L368A+Y407V+F405K+Q347R

<400> SEQUENCE: 12

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly Lys
225

<210> SEQ ID NO 13
<211> LENGTH: 227
<212> TYPE: PRT
<213> ORGANISM: Artificial Sequence
<220> FEATURE:
<223> OTHER INFORMATION: Y349C+T366W+K409A+Q347R

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met

```
                    20                  25                  30

Ile Ser Arg Thr Pro Glu Val Thr Cys Val Val Val Asp Val Ser His
            35                  40                  45

Glu Asn Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                    85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
        115                 120                 125

Cys Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 14
<211> LENGTH: 227
<212> TYPE: PRT
<213> ORGANISM: Artificial Sequence
<220> FEATURE:
<223> OTHER INFORMATION: D356C+T366S+L368A+Y407V+F405K+K360E+Q347E

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                    85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Tyr Thr Leu Pro Pro Ser Arg Cys Glu Leu Thr Glu Asn Gln Val Ser
130                 135                 140

Leu Ser Cys Ala Val Lys Gly Phe Tyr Pro Ser Asp Ile Ala Val Glu
```

```
                145                 150                 155                 160

Trp Glu Ser Asn Gly Gln Pro Glu Asn Tyr Lys Thr Thr Pro Pro
                165                 170                 175

Val Leu Asp Ser Asp Gly Ser Phe Lys Leu Val Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
        210                 215                 220

Pro Gly Lys
225

<210> SEQ ID NO 15
<211> LENGTH: 227
<212> TYPE: PRT
<213> ORGANISM: Artificial Sequence
<220> FEATURE:
<223> OTHER INFORMATION: T366W+K409A+K392D

<400> SEQUENCE: 15

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asn Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Tyr Ser Ala Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
        210                 215                 220

Pro Gly Lys
225

<210> SEQ ID NO 16
<211> LENGTH: 227
<212> TYPE: PRT
<213> ORGANISM: Artificial Sequence
<220> FEATURE:
<223> OTHER INFORMATION: T366S+L368A+Y407V+D399S+F405K
```

<400> SEQUENCE: 16

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Ser Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 17
<211> LENGTH: 227
<212> TYPE: PRT
<213> ORGANISM: Artificial Sequence
<220> FEATURE:
<223> OTHER INFORMATION: T366W+K409A

<400> SEQUENCE: 17

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 18
<211> LENGTH: 227
<212> TYPE: PRT
<213> ORGANISM: Artificial Sequence
<220> FEATURE:
<223> OTHER INFORMATION: T366S+L368G+Y407A+F405K

<400> SEQUENCE: 18

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Ser Cys Gly Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Ala Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

```
<210> SEQ ID NO 19
<211> LENGTH: 227
<212> TYPE: PRT
<213> ORGANISM: Artificial Sequence
<220> FEATURE:
<223> OTHER INFORMATION: T366W+K409A+Y349D

<400> SEQUENCE: 19

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 20
<211> LENGTH: 227
<212> TYPE: PRT
<213> ORGANISM: Artificial Sequence
<220> FEATURE:
<223> OTHER INFORMATION: T366S+L368A+Y407V+F405K+E357A

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Ala Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 21
<211> LENGTH: 227
<212> TYPE: PRT
<213> ORGANISM: Artificial Sequence
<220> FEATURE:
<223> OTHER INFORMATION: T366W+K409A+Y349D+S354D

<400> SEQUENCE: 21

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Asp Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
    210                 215                 220

Pro Gly Lys
225

<210> SEQ ID NO 22
<211> LENGTH: 227
<212> TYPE: PRT
<213> ORGANISM: Artificial Sequence
<220> FEATURE:
<223> OTHER INFORMATION: T366W+F405K

<400> SEQUENCE: 22

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 23
<211> LENGTH: 227
<212> TYPE: PRT
<213> ORGANISM: Artificial Sequence
<220> FEATURE:
<223> OTHER INFORMATION: T366S+L368A+Y407V+K409A

<400> SEQUENCE: 23

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

```
            35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
            130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Ala Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
210                 215                 220
Pro Gly Lys
225

<210> SEQ ID NO 24
<211> LENGTH: 227
<212> TYPE: PRT
<213> ORGANISM: Artificial Sequence
<220> FEATURE:
<223> OTHER INFORMATION: T366W+F405K+D399S

<400> SEQUENCE: 24

Asp Lys Thr His Thr Cys Pro Pro Cys Pro Ala Pro Glu Leu Leu Gly
  1               5                  10                  15
Gly Pro Ser Val Phe Leu Phe Pro Pro Lys Pro Lys Asp Thr Leu Met
                 20                  25                  30
Ile Ser Arg Thr Pro Glu Val Thr Cys Val Val Val Asp Val Ser His
             35                  40                  45
Glu Asn Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
            130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
```

```
                165                 170                 175
Val Leu Ser Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 25
<211> LENGTH: 227
<212> TYPE: PRT
<213> ORGANISM: Artificial Sequence
<220> FEATURE:
<223> OTHER INFORMATION: T366S+L368A+Y407V+K409A+K392D

<400> SEQUENCE: 25

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 26
<211> LENGTH: 227
<212> TYPE: PRT
<213> ORGANISM: Artificial Sequence
<220> FEATURE:
<223> OTHER INFORMATION: T366S+L368G+Y407A+K409A

<400> SEQUENCE: 26
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Ser Cys Gly Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Ala Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 27
<211> LENGTH: 227
<212> TYPE: PRT
<213> ORGANISM: Artificial Sequence
<220> FEATURE:
<223> OTHER INFORMATION: T366W +F405K +Y349D

<400> SEQUENCE: 27

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asn Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125
```

```
Asp Thr Leu Pro Pro Ser Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 28
<211> LENGTH: 227
<212> TYPE: PRT
<213> ORGANISM: Artificial Sequence
<220> FEATURE:
<223> OTHER INFORMATION: T366S+L368A+Y407V +K409A +E357A

<400> SEQUENCE: 28

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Ala Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 29
<211> LENGTH: 227
```

```
<212> TYPE: PRT
<213> ORGANISM: Artificial Sequence
<220> FEATURE:
<223> OTHER INFORMATION: T366W+F405K+Y349D+S354D

<400> SEQUENCE: 29

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Asp Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 30
<211> LENGTH: 227
<212> TYPE: PRT
<213> ORGANISM: Artificial Sequence
<220> FEATURE:
<223> OTHER INFORMATION: wildtype human IgG1-Fc region amino acid

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly Lys
225

<210> SEQ ID NO 31
<211> LENGTH: 681
<212> TYPE: DNA
<213> ORGANISM: Artificial Sequence
<220> FEATURE:
<223> OTHER INFORMATION: Fc gene fragment

<400> SEQUENCE: 31
gacaagaccc acacctgccc ccctgcccc gccccgagc tgctgggcgg ccccagcgtg       60
ttcctgttcc cccccaagcc caaggacacc ctgatgatca gccgcacccc cgaggtgacc    120
tgcgtggtgg tggacgtgag ccacgagaac cccgaggtga agttcaactg gtacgtggac    180
ggcgtggagg tgcacaacgc caagaccaag ccccgcgagg agcagtacaa cagcacctac    240
cgcgtggtga gcgtgctgac cgtgctgcac caggactggc tgaacggcaa ggagtacaag    300
tgcaaggtga gcaacaaggc cctgcccgcc cccatcgaga agaccatcag caaggccaag    360
ggccagcccc gcgagcccca ggtgtacacc ctgcccccca gccgcgacga gctgaccaag    420
aaccaggtga gcctgacctg cctggtgaag ggcttctacc ccagcgacat cgccgtggag    480
tgggagagca acggccagcc cgagaacaac tacaagacca cccccccgt gctggacagc    540 gacggcagct tcttcctgta cagcaagctg accgtggaca gagccgctg gcagcagggc    600 aacgtgttca gctgcagcgt gatgcacgag gccctgcaca accactacac ccagaagagc    660
ctgagcctga gccccggcaa g                                              681

<210> SEQ ID NO 32
<211> LENGTH: 741
<212> TYPE: DNA
<213> ORGANISM: Artificial Sequence
<220> FEATURE:
<223> OTHER INFORMATION: polynucleotide fragment encoding a mouse
      kappaIII signal peptide

<400> SEQUENCE: 32
atggagaccg acaccctgct gctgtgggtg ctgctgctgt gggtgcccgg cagcaccggc       60
gacaagaccc acacctgccc ccctgcccc gccccgagc tgctgggcgg ccccagcgtg       120
ttcctgttcc cccccaagcc caaggacacc ctgatgatca gccgcacccc cgaggtgacc    180

```
tgcgtggtgg tggacgtgag ccacgagaac cccgaggtga agttcaactg gtacgtggac    240
ggcgtggagg tgcacaacgc caagaccaag ccccgcgagg agcagtacaa cagcacctac    300
cgcgtggtga gcgtgctgac cgtgctgcac caggactggc tgaacggcaa ggagtacaag    360
tgcaaggtga gcaacaaggc cctgcccgcc cccatcgaga gaccatcag caaggccaag    420 ggccagcccc gcgagcccca ggtgtacacc ctgccccca gccgcgacga gctgaccaag    480
aaccaggtga gcctgacctg cctggtgaag ggcttctacc ccagcgacat cgccgtggag    540
tgggagagca acggccagcc cgagaacaac tacaagacca ccccccccgt gctggacagc    600
gacggcagct tcttcctgta cagcaagctg accgtggaca gagccgctg cagcagggc    660 aacgtgttca gctgcagcgt gatgcacgag gccctgcaca accactacac ccagaagagc    720
ctgagcctga gccccggcaa g                                              741

<210> SEQ ID NO 33
<211> LENGTH: 1473
<212> TYPE: DNA
<213> ORGANISM: Artificial Sequence
<220> FEATURE:
<223> OTHER INFORMATION: gene  of ScFv-Fc fusion protein

<400> SEQUENCE: 33
atggagaccg acaccctgct gctgtgggtg ctgctgctgt gggtgcccgg cagcaccggc     60
gaggtgcagc tgctggagag cggcggcggc gtggtgcagc ccggccgcag cctgcgcctg    120
agctgcatcg ccagcggctt caccttcagc agctacccca tgacctgggt gcgccaggcc    180
cccggcaagg gcctggagtg gtggccagc atcagctacg acggcagcta caagtacaag    240
gccgacagca tgaagggccg cctgaccatc agccgcgaca acagcaagaa caccctgtac    300
ctggagatga acagcctgac cgccgaggac accgccgtgt actactgcgc ccgcaccgcc    360
ttcttcaacg cctacgactt ctggggccag ggcaccctgg tgaccgtgag cagcgccagc    420
accaagggcc ccagcgtggg cggcggcggc agcggcggcg gcggcagcga gatcgtgatg    480
acccagagcc ccgccaccct gagcgtgagc cccggcgagc gcgccaccct gagctgccgc    540
gccagccaga gcgtgcgcag caacctggcc tggtaccagc agaagcccgg ccaggccccc    600
cgcctgctga tctacgccgc cagcacccgc gccaccggca tccccgcccg cttcagcggc    660
agcggcagcg gcaccgagtt caccctgacc atcagcagcc tgcagagcga ggacttcgcc    720
gtgtactact gccagcagta caacgagtgg ttccgcacca cggccaggg caccaaggtg    780 gagatcaagc gcgacaagac ccacacctgc cccccctgcc ccgcccccga gctgctgggc    840
ggccccagcg tgttcctgtt ccccccaag cccaaggaca ccctgatgat cagccgcacc    900
cccgaggtga cctgcgtggt ggtggacgtg agccacgaga ccccgaggt gaagttcaac    960 tggtacgtgg acggcgtgga ggtgcacaac gccaagacca gccccgcga ggagcagtac    1020 aacagcacct accgcgtggt gagcgtgctg accgtgctgc accaggactg gctgaacggc    1080
aaggagtaca agtgcaaggt gagcaacaag gccctgcccg cccccatcga aagaccatc    1140 agcaaggcca agggccagcc ccgcgagccc caggtgtaca ccctgccccc cagccgcgac    1200
gagctgacca gaaccaggt gagcctgacc tgcctggtga agggcttcta ccccagcgac    1260
atcgccgtgg agtgggagag caacggccag cccgagaaca actacaagac cacccccccc    1320
gtgctggaca gcgacggcag cttcttcctg tacagcaagc tgaccgtgga caagagccgc    1380
tggcagcagg gcaacgtgtt cagctgcagc gtgatgcacg aggccctgca caaccactac    1440
acccagaaga gcctgagcct gagccccggc aag                                1473
```

<210> SEQ ID NO 34
<211> LENGTH: 471
<212> TYPE: PRT
<213> ORGANISM: Artificial Sequence
<220> FEATURE:
<223> OTHER INFORMATION: ScFv-Fc fusion protein

<400> SEQUENCE: 34

```
Glu Val Gln Leu Leu Glu Ser Gly Gly Val Val Gln Pro Gly Arg
1               5                   10                  15

Ser Leu Arg Leu Ser Cys Ile Ala Ser Gly Phe Thr Phe Ser Ser Tyr
                20                  25                  30

Pro Met Thr Trp Val Arg Gln Ala Pro Gly Lys Gly Leu Glu Trp Val
                35                  40                  45

Ala Ser Ile Ser Tyr Asp Gly Ser Tyr Lys Tyr Lys Ala Asp Ser Met
        50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
                100                 105                 110

Leu Val Thr Val Ser Ser Ala Ser Thr Lys Gly Pro Ser Val Gly Gly
                115                 120                 125

Gly Gly Ser Gly Gly Gly Gly Ser Glu Ile Val Met Thr Gln Ser Pro
        130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
                180                 185                 190

Gly Ile Pro Ala Arg Phe Ser Gly Ser Gly Ser Gly Thr Glu Phe Thr
                195                 200                 205

Leu Thr Ile Ser Ser Leu Gln Ser Glu Asp Phe Ala Val Tyr Tyr Cys
        210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asn Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365
```

```
        Glu Pro Gln Val Tyr Thr Leu Pro Pro Ser Arg Asp Glu Leu Thr Lys
            370                 375                 380

Asn Gln Val Ser Leu Thr Cys Leu Val Lys Gly Phe Tyr Pro Ser Asp
        385                 390                 395                 400

Ile Ala Val Glu Trp Glu Ser Asn Gly Gln Pro Glu Asn Asn Tyr Lys
                        405                 410                 415

Thr Thr Pro Pro Val Leu Asp Ser Asp Gly Ser Phe Phe Leu Tyr Ser
                    420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
            450                 455                 460

Leu Ser Leu Ser Pro Gly Lys
        465                 470

<210> SEQ ID NO 35
<211> LENGTH: 1121
<212> TYPE: DNA
<213> ORGANISM: Artificial Sequence
<220> FEATURE:
<223> OTHER INFORMATION: a fusion gene fragment encoding the fusion
      protein VhH-Fc

<400> SEQUENCE: 35
atggagaccg acaccctgct gctgtgggtg ctgctgctgt gggtgcccgg cagcaccggc      60
caggtgcagc tgcaggagtc tgggggaggc tcggtgcagg ctggagggtc tctgagactc     120
tcctgtgcag cctctgaata catctacagt agctactgca tggcctggtt ccgccaggct     180
ccagggaagg agcgcgaggg ggtcgcagtt attgggagtg atggtagcac aagctacgca     240
gactccgtga aggccgatt caccatctcc aaagacaacg ccaagaacac tctgtatctg     300
caaatgaaca gcctgaaacc tgaggacact gccatgtact actgtgcggc catcggtggt     360
tactgctacc aaccacccta tgagtaccag tactggggcc aggggaccca ggtcaccgtc     420
tcccagaacc gaaaagcagc gacaagaccc acacctgccc ccctgccccc gccccgagc     480 tgctgggcgg ccccagcgtg ttcctgttcc ccccaagcc aaggacacc ctgatgatca     540 gccgcacccc cgaggtgacc tgcgtggtgg tggacgtgag ccacgagaac cccgaggtga     600
agttcaactg gtacgtggac ggcgtggagg tgcacaacgc caagaccaag ccccgcgagg     660
agcagtacaa cagcacctac cgcgtggtga gcgtgctgac cgtgctgcac caggactggc     720
tgaacggcaa ggagtacaag tgcaaggtga gcaacaaggc cctgcccgcc cccatcgaga     780
agaccatcag caaggccaag ggccagcccc gcgagcccca ggtgtacacc ctgccccca     840 gccgcgacga gctgaccaag aaccaggtga gcctgacctg cctggtgaag ggcttctacc     900
ccagcgacat cgccgtggag tgggagagca cggccagcc cgagaacaac tacaagacca     960
ccccccccgt gctggacagc gacggcagct tcttcctgta cagcaagctg accgtggaca    1020
agagccgctg gcagcagggc aacgtgttca gctgcagcgt gatgcacgag gccctgcaca    1080
accactacac ccagaagagc ctgagcctga gccccggcaa g                        1121

<210> SEQ ID NO 36
<211> LENGTH: 354
<212> TYPE: PRT
<213> ORGANISM: Artificial Sequence
<220> FEATURE:
<223> OTHER INFORMATION: fusion protein VhH-Fc
```

<400> SEQUENCE: 36

Gln Val Gln Leu Gln Glu Ser Gly Gly Gly Ser Val Gln Ala Gly Gly
1               5                   10                  15

Ser Leu Arg Leu Ser Cys Ala Ala Ser Glu Tyr Ile Tyr Ser Ser Tyr
            20                  25                  30

Cys Met Ala Trp Phe Arg Gln Ala Pro Gly Lys Glu Arg Glu Gly Val
        35                  40                  45

Ala Val Ile Gly Ser Asp Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65              70                  75                  80

Gln Met Asn Ser Leu Lys Pro Glu Asp Thr Ala Met Tyr Tyr Cys Ala
                85                  90                  95

Ala Ile Gly Gly Tyr Cys Tyr Gln Pro Pro Tyr Glu Tyr Gln Tyr Trp
            100                 105                 110

Gly Gln Gly Thr Gln Val Thr Val Ser Ser Glu Pro Lys Ser Ser Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys

<210> SEQ ID NO 37
<211> LENGTH: 214
<212> TYPE: PRT
<213> ORGANISM: Artificial Sequence
<220> FEATURE:
<223> OTHER INFORMATION: amino acid sequence of T-LC

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 708
<212> TYPE: DNA
<213> ORGANISM: Artificial Sequence
<220> FEATURE:
<223> OTHER INFORMATION: gene of T-LC

<400> SEQUENCE: 38
gacatccaga tgacccagag ccccagcagc ctgagcgcca gcgtgggcga ccgcgtgacc      60
atcacctgcc gcgccagcca ggacgtgaac accgccgtgg cctggtacca gcagaagccc     120
ggcaaggccc ccaagctgct gatctacagc gccagcttcc tgtacagcgg cgtgcccagc     180
cgcttcagcg gcagccgcag cggcaccgac ttcaccctga ccatcagcag cctgcagccc     240
gaggacttcg ccacctacta ctgccagcag cactacacca ccccccccac cttcggccag     300
ggcaccaagg tggagatcaa atactactgc cagcagaaca caactggcc caccaccttc     360 ggcgccggca ccaagctgga gctgaagcgc accgtggccg cccccagcgt gttcatcttc     420 cccccagcg acgagcagct gaagagcggc accgccagcg tggtgtgcct gctgaacaac     480 ttctacccc gcgaggccaa ggtgcagtgg aaggtggaca acgccctgca gagcggcaac     540
agccaggaga gcgtgaccga gcaggacagc aaggacagca cctacagcct gagcagcacc     600
ctgaccctga gcaaggccga ctacgagaag cacaaggtgt acgcctgcga ggtgacccac     660
cagggcctga gcagccccgt gaccaagagc ttcaaccgcg gcgagtgc                  708

<210> SEQ ID NO 39
```

```
<211> LENGTH: 450
<212> TYPE: PRT
<213> ORGANISM: Artificial Sequence
<220> FEATURE:
<223> OTHER INFORMATION: amino acid sequences of T-Fc9

<400> SEQUENCE: 39
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Asn | Ile | Lys | Asp | Thr |
| | | | 20 | | | | | 25 | | | | | 30 | | |
| Tyr | Ile | His | Trp | Val | Arg | Gln | Ala | Pro | Gly | Lys | Gly | Leu | Glu | Trp | Val |
| | | | 35 | | | | | 40 | | | | | 45 | | |
| Ala | Arg | Ile | Tyr | Pro | Thr | Asn | Gly | Tyr | Thr | Arg | Tyr | Ala | Asp | Ser | Val |
| | 50 | | | | | 55 | | | | | 60 | | | | |
| Lys | Gly | Arg | Phe | Thr | Ile | Ser | Ala | Asp | Thr | Ser | Lys | Asn | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ser | Arg | Trp | Gly | Gly | Asp | Gly | Phe | Tyr | Ala | Met | Asp | Tyr | Trp | Gly | Gln |
| | | | | 100 | | | | | 105 | | | | | 110 | |
| Gly | Thr | Leu | Val | Thr | Val | Ser | Ser | Ala | Ser | Thr | Lys | Gly | Pro | Ser | Val |
| | | | 115 | | | | | 120 | | | | | 125 | | |
| Phe | Pro | Leu | Ala | Pro | Ser | Ser | Lys | Ser | Thr | Ser | Gly | Gly | Thr | Ala | Ala |
| 130 | | | | | 135 | | | | | 140 | | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | | 180 | | | | | 185 | | | | | 190 | |
| Ser | Ser | Ser | Leu | Gly | Thr | Gln | Thr | Tyr | Ile | Cys | Asn | Val | Asn | His | Lys |
| | | | 195 | | | | | 200 | | | | | 205 | | |
| Pro | Ser | Asn | Thr | Lys | Val | Asp | Lys | Arg | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Asp | Glu | Leu | Thr | Lys | Asn | Gln | Val | Ser | Leu |
| | | | 355 | | | | | 360 | | | | | 365 | | |
| Trp | Cys | Leu | Val | Lys | Gly | Phe | Tyr | Pro | Ser | Asp | Ile | Ala | Val | Glu | Trp |
| | | | 370 | | | | | 375 | | | | | 380 | | |

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Ala Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 40
<211> LENGTH: 1350
<212> TYPE: DNA
<213> ORGANISM: Artificial Sequence
<220> FEATURE:
<223> OTHER INFORMATION: gene of T-Fc9

<400> SEQUENCE: 40
gaggtgcagc tggtggagag cggcggcggc ctggtgcagc ccggcggcag cctgcgcctg      60
agctgcgccg ccagcggctt caacatcaag gacacctaca tccactgggt gcgccaggcc     120
cccggcaagg gcctggagtg ggtggcccgc atctacccca ccaacggcta cacccgctac     180
gccgacagcg tgaagggccg cttcaccatc agcgccgaca ccagcaagaa caccgcctac     240
ctgcagatga acagcctgcg cgccgaggac accgccgtgt actactgcag ccgctggggc     300
ggcgacggct tctacgccat ggactactgg ggccagggca ccctggtgac cgtgagcagc     360
gccagcacta agggccctc tgtgtttcca ctcgccctt ctagcaaaag cacttccgga      420
ggaactgccg ctctgggctg tctggtgaaa gattacttcc ccgaaccagt cactgtgtca     480
tggaactctg gagcactgac atctggagtt cacacctttc ctgctgtgct gcagagttct     540
ggactgtact ccctgtcatc tgtggtcacc gtgccatctt catctctggg acccagacc      600 tacatctgta acgtgaacca caaaccctcc aacacaaaag tggacaaacg agtcgaacca     660
aaatcttgtg acaaaaccca cacatgccca ccgtgcccag ctccggaact cctgggcgga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccaag tcgggatgag     1080
ctgaccaaga accaggtcag cctgtggtgc ctggtcaaag gcttctatcc cagcgacatc    1140
gccgtggagt gggagagcaa tgggcagccg gagaacaact acaagaccac gcctcccgtg    1200
ttggactccg acggctcctt cttcctctac agcgcgctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                     1350

<210> SEQ ID NO 41
<211> LENGTH: 214
<212> TYPE: PRT
<213> ORGANISM: Artificial Sequence
<220> FEATURE:
<223> OTHER INFORMATION: amino acid sequence of P-LC
```

<400> SEQUENCE: 41

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 42
<211> LENGTH: 708
<212> TYPE: DNA
<213> ORGANISM: Artificial Sequence
<220> FEATURE:
<223> OTHER INFORMATION: gene of P-LC

<400> SEQUENCE: 42

```
gacatccaga tgacccagag ccccagcagc ctgagcgcca gcgtgggcga ccgcgtgacc    60
atcacctgca aggccagcca ggacgtgagc atcggcgtgg cctggtacca gcagaagccc   120
ggcaaggccc ccaagctgct gatctacagc gccagctacc gctacaccgg cgtgcccagc   180
cgcttcagcg gcagcggcag cggcaccgac ttcaccctga ccatcagcag cctgcagccc   240
gaggacttcg ccacctacta ctgccagcag tactacatct accccctaca cttcggccag   300
ggcaccaagg tggagatcaa gtactactgc cagcagaaca caactggcc caccaccttc   360
ggcgccggca ccaagctgga gctgaagcgc accgtggccg cccccagcgt gttcatcttc   420
ccccccagcg acgagcagct gaagagcggc accgccagcg tggtgtgcct gctgaacaac   480
ttctacccc gcgaggccaa ggtgcagtgg aaggtggaca acgccctgca gagcggcaac   540
agccaggaga gcgtgaccga gcaggacagc aaggacagca cctacagcct gagcagcacc   600
ctgaccctga gcaaggccga ctacgagaag cacaaggtgt acgcctgcga ggtgacccac   660
cagggcctga gcagccccgt gaccaagagc ttcaaccgcg gcgagtgc              708
```

```
<210> SEQ ID NO 43
<211> LENGTH: 449
<212> TYPE: PRT
<213> ORGANISM: Artificial Sequence
<220> FEATURE:
<223> OTHER INFORMATION: amino acid sequences of P-Fc9

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Trp
        355                 360                 365
```

```
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Ala Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Lys

<210> SEQ ID NO 44
<211> LENGTH: 1347
<212> TYPE: DNA
<213> ORGANISM: Artificial Sequence
<220> FEATURE:
<223> OTHER INFORMATION: gene of P-Fc9

<400> SEQUENCE: 44
gaggtgcagc tggtggagag cggcggcggc ctggtgcagc ccggcggcag cctgcgcctg      60
agctgcgccg ccagcggctt caccttcacc gactacacca tggactgggt gcgccaggcc     120
cccggcaagg gcctggagtg gtggccgac gtgaacccca cagcggcgg cagcatctac       180 aaccagcgct tcaagggccg cttcaccctg agcgtggacc gcagcaagaa caccctgtac     240
ctgcagatga acagcctgcg cgccgaggac accgccgtgt actactgcgc cgcaacctg     300 ggccccagct tctacttcga ctactgggc cagggcaccc tggtgaccgt gagcagcgcc      360
agcactaagg gccctctgt gtttccactc gccccttcta gcaaaagcac ttccggagga      420
actgccgctc tgggctgtct ggtgaaagat tacttccccg aaccagtcac tgtgtcatgg     480
aactctggag cactgacatc tggagttcac acctttcctg ctgtgctgca gagttctgga     540
ctgtactccc tgtcatctgt ggtcaccgtg ccatcttcat ctctggggac ccagacctac     600
atctgtaacg tgaaccacaa accctccaac acaaaagtgg acaaacgagt cgaaccaaaa     660
tcttgtgaca aaacccacac atgcccaccg tgcccagctc cggaactcct gggcggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020 gccaagggc agccccgaga accacaggtg tacaccctgc ccccaagtcg ggatgagctg    1080
accaagaacc aggtcagcct gtggtgcctg gtcaaaggct tctatcccag cgacatcgcc    1140
gtggagtggg agagcaatgg gcagccggag aacaactaca agaccacgcc tcccgtgttg    1200
gactccgacg gctccttctt cctctacagc gcgctcaccg tggacaagag caggtggcag    1260
caggggaacg tcttctcatg ctccgtgatg catgaggctc tgcacaacca ctacacgcag    1320
aagagcctct ccctgtctcc gggtaaa                                       1347

<210> SEQ ID NO 45
<211> LENGTH: 214
<212> TYPE: PRT
<213> ORGANISM: Artificial Sequence
<220> FEATURE:
```

<223> OTHER INFORMATION: amino acid sequence of Mab806-LC

<400> SEQUENCE: 45

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 708
<212> TYPE: DNA
<213> ORGANISM: Artificial Sequence
<220> FEATURE:
<223> OTHER INFORMATION: gene of Mab806-LC

<400> SEQUENCE: 46

```
gacatcctga tgacccagag ccccagcagc atgagcgtga gcctgggcga caccgtgagc      60
atcacctgcc acagcagcca ggacatcaac agcaacatcg gctggctgca gcagcgcccc     120
ggcaagagct tcaagggcct gatctaccac ggcaccaacc tggacgacga ggtgcccagc     180
cgcttcagcg gcagcggcag cggcgccgac tacagcctga ccatcagcag cctggagagc     240
gaggacttcg ccgactacta ctgcgtgcag tacgcccagt tcccctggac cttcggcggc     300
ggcaccaagc tggagatcaa gtactactgc agcagaaca acaactggcc caccaccttc     360
ggcgccggca ccaagctgga gctgaagcgc accgtggccg cccccagcgt gttcatcttc     420
cccccagcg acgagcagct gaagagcggc accgccagct ggtgtgcct gctgaacaac     480
ttctacccc gcgaggccaa ggtgcagtgg aaggtggaca acgccctgca gagcggcaac     540
agccaggaga gcgtgaccga gcaggacagc aaggacagca cctacagcct gagcagcacc     600
ctgaccctga gcaaggccga ctacgagaag cacaaggtgt acgcctgcga ggtgacccac     660
cagggcctga gcagccccgt gaccaagagc ttcaaccgcg gcgagtgc                   708
```

<210> SEQ ID NO 47
<211> LENGTH: 446
<212> TYPE: PRT
<213> ORGANISM: Artificial Sequence
<220> FEATURE:
<223> OTHER INFORMATION: amino acid sequences of Mab806-Fc9

<400> SEQUENCE: 47

```
Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Trp Cys Leu Val
        355                 360                 365
```

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Ala Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 48
<211> LENGTH: 1338
<212> TYPE: DNA
<213> ORGANISM: Artificial Sequence
<220> FEATURE:
<223> OTHER INFORMATION: gene of Mab806-Fc9

<400> SEQUENCE: 48

```
gacgtgcagc tgcaggagag cggccccagc ctggtgaagc ccagccagag cctgagcctg      60
acctgcaccg tgaccggcta cagcatcacc agcgacttcg cctggaactg gatccgccag     120
ttccccggca caagctgga gtggatgggc tacatcagct acagcggcaa cacccgctac     180
aaccccagcc tgaagagccg catcagcatc acccgcgaca ccagcaagaa ccagttcttc     240
ctgcagctga cagcgtgac catcgaggac accgccacct actactgcgt gaccgccggc     300
cgcggcttcc cctactgggg ccagggcacc ctggtgaccg tgagcgccgc cagcactaag     360
ggcccctctg tgtttccact cgccccttct agcaaaagca cttccggagg aactgccgct     420
ctgggctgtc tggtgaaaga ttacttcccc gaaccagtca ctgtgtcatg aactctggga     480
gcactgacat ctggagttca ccctttcct gctgtgctgc agagttctgg actgtactcc     540
ctgtcatctg tggtcaccgt gccatcttca tctctgggga cccagaccta catctgtaac     600
gtgaaccaca accctccaa cacaaagtg gacaaacgag tcgaaccaaa atcttgtgac     660
aaaacccaca catgcccacc gtgcccagct ccggaactcc tgggcggacc gtcagtcttc     720
ctcttccccc caaaacccaa ggacaccctc atgatctccc ggaccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccaagtc gggatgagct gaccaagaac    1080
caggtcagcc tgtggtgcct ggtcaaaggc ttctatccca gcgacatcgc cgtggagtgg    1140
gagagcaatg ggcagccgga gaacaactac aagaccacgc ctcccgtgtt ggactccgac    1200
ggctccttct tcctctacag cgcgctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338
```

<210> SEQ ID NO 49
<211> LENGTH: 220
<212> TYPE: PRT
<213> ORGANISM: Artificial Sequence
<220> FEATURE:
<223> OTHER INFORMATION: amino acid sequence of 5E5-LC

<400> SEQUENCE: 49

```
Glu Leu Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 50
<211> LENGTH: 660
<212> TYPE: DNA
<213> ORGANISM: Artificial Sequence
<220> FEATURE:
<223> OTHER INFORMATION: gene of 5E5-LC

<400> SEQUENCE: 50

```
gaactcgtga tgacccagag ccccagctct ctgacagtga cagccggcga gaaagtgacc      60
atgatctgca gtcctccca gagcctgctg aactccggcg accagaagaa ctacctgacc     120
tggtatcagc agaaacccgg ccagcccccc aagctgctga tcttttgggc cagcacccgg     180
gaaagcggcg tgcccgatag attcacaggc agcggctccg gcaccgactt tacccctgacc    240
atcagctccg tgcaggccga ggacctggcc gtgtattact gccagaacga ctacagctac     300
cccctgacct tcggagccgg caccaagctg gaactgaagc gtacggtggc tgccaccatct    360
gtcttcatct tcccgccatc tgatgagcag ttgaaatctg gtaccgctag cgttgtgtgc     420
ctgctgaata acttttatcc acgggaggct aaggtgcagt ggaaagtgga caatgccctc     480
cagagcggaa atagccaaga gtccgttacc gaacaggact ctaaagactc tacatactcc     540
ctgtcctcca cactgaccct ctccaaggcc gactatgaga acacaaggt ttacgcatgc     600
gaggtcacac accagggact ctcctctccc gtgaccaaga gcttcaaccg gggagaatgc    660
```

<210> SEQ ID NO 51

```
<211> LENGTH: 446
<212> TYPE: PRT
<213> ORGANISM: Artificial Sequence
<220> FEATURE:
<223> OTHER INFORMATION: amino acid sequences of 5E5-Fc9

<400> SEQUENCE: 51
```

| | | | | | | | | | | | | | | | |
|---|---|---|---|---|---|---|---|---|---|---|---|---|---|---|---|
| Gln | Val | Gln | Leu | Gln | Gln | Ser | Asp | Ala | Glu | Leu | Val | Lys | Pro | Gly | Ser |
| 1 | | | | 5 | | | | | 10 | | | | | 15 | |
| Ser | Val | Lys | Ile | Ser | Cys | Lys | Ala | Ser | Gly | Tyr | Thr | Phe | Thr | Asp | His |
| | | | 20 | | | | | 25 | | | | | 30 | | |
| Ala | Ile | His | Trp | Val | Lys | Gln | Lys | Pro | Glu | Gln | Gly | Leu | Glu | Trp | Ile |
| | | 35 | | | | | 40 | | | | | 45 | | | |
| Gly | His | Phe | Ser | Pro | Gly | Asn | Thr | Asp | Ile | Lys | Tyr | Asn | Asp | Lys | Phe |
| | 50 | | | | | 55 | | | | | 60 | | | | |
| Lys | Gly | Lys | Ala | Thr | Leu | Thr | Val | Asp | Arg | Ser | Ser | Thr | Ala | Tyr | |
| 65 | | | | | 70 | | | | | 75 | | | | | 80 |
| Met | Gln | Leu | Asn | Ser | Leu | Thr | Ser | Glu | Asp | Ser | Ala | Val | Tyr | Phe | Cys |
| | | | | 85 | | | | | 90 | | | | | 95 | |
| Lys | Thr | Ser | Thr | Phe | Phe | Phe | Asp | Tyr | Trp | Gly | Gln | Gly | Thr | Thr | Leu |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | 115 | | | | | 120 | | | | | 125 | | | |
| Pro | Ser | Ser | Lys | Ser | Thr | Ser | Gly | Gly | Thr | Ala | Ala | Leu | Gly | Cys | Leu |
| | 130 | | | | | 135 | | | | | 140 | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | 195 | | | | | 200 | | | | | 205 | | | |
| Lys | Val | Asp | Lys | Arg | Val | Glu | Pro | Lys | Ser | Cys | Asp | Lys | Thr | His | Thr |
| | 210 | | | | | 215 | | | | | 220 | | | | |
| Cys | Pro | Pro | Cys | Pro | Ala | Pro | Glu | Leu | Leu | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | 275 | | | | | 280 | | | | | 285 | | | |
| Lys | Pro | Arg | Glu | Glu | Gln | Tyr | Asn | Ser | Thr | Tyr | Arg | Val | Val | Ser | Val |
| | 290 | | | | | 295 | | | | | 300 | | | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Ala | Leu | Pro | Ala | Pro | Ile | Glu | Lys | Thr | Ile | Ser |
| | | | | 325 | | | | | 330 | | | | | 335 | |
| Lys | Ala | Lys | Gly | Gln | Pro | Arg | Glu | Pro | Gln | Val | Tyr | Thr | Leu | Pro | Pro |
| | | | 340 | | | | | 345 | | | | | 350 | | |
| Ser | Arg | Asp | Glu | Leu | Thr | Lys | Asn | Gln | Val | Ser | Leu | Trp | Cys | Leu | Val |
| | | 355 | | | | | 360 | | | | | 365 | | | |
| Lys | Gly | Phe | Tyr | Pro | Ser | Asp | Ile | Ala | Val | Glu | Trp | Glu | Ser | Asn | Gly |
| | 370 | | | | | 375 | | | | | 380 | | | | |

Gln Pro Glu Asn Asn Tyr Lys Thr Thr Pro Pro Val Leu Asp Ser Asp
385                 390                 395                 400

Gly Ser Phe Phe Leu Tyr Ser Ala Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 52
<211> LENGTH: 1338
<212> TYPE: DNA
<213> ORGANISM: Artificial Sequence
<220> FEATURE:
<223> OTHER INFORMATION: gene of 5E5-Fc9

<400> SEQUENCE: 52

| | |
|---|---|
| caggtgcagc tgcagcagtc tgatgccgag ctcgtgaagc tggcagcag cgtgaagatc | 60 |
| agctgcaagg ccagcggcta caccttcacc gaccacgcca tccactgggt caagcagaag | 120 |
| cctgagcagg gcctggaatg gatcggccac ttcagccccg caacaccga catcaagtac | 180 |
| aacgacaagt tcaagggcaa ggccaccctg accgtggaca aagcagcag caccgcctac | 240 |
| atgcagctga acagcctgac cagcgaggac agcgccgtgt acttctgcaa gaccagcacc | 300 |
| ttcttttttcg actactgggg ccagggcaca accctgacag tgtctagcgc cagcactaag | 360 |
| gggccctctg tgtttccact cgccccttct agcaaaagca cttccggagg aactgccgct | 420 |
| ctgggctgtc tggtgaaaga ttacttcccc gaaccagtca ctgtgtcatg gaactctgga | 480 |
| gcactgacat ctggagttca ccctttcct gctgtgctgc agagttctgg actgtactcc | 540 |
| ctgtcatctg tggtcaccgt gccatcttca tctctgggga cccagaccta catctgtaac | 600 |
| gtgaaccaca aaccctccaa cacaaaagtg gacaaacgag tcgaaccaaa atcttgtgac | 660 |
| aaaacccaca catgcccacc gtgcccagct ccggaactcc tgggcggacc gtcagtcttc | 720 |
| ctcttccccc caaaacccaa ggacaccctc atgatctccc ggaccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgt | 900 |
| gtggtcagcg tcctcaccgt cctgcaccag gactggctga atggcaagga gtacaagtgc | 960 |
| aaggtctcca acaaagccct cccagcccc atcgagaaaa ccatctccaa agccaagggg | 1020 |
| cagccccgag aaccacaggt gtacaccctg cccccaagtc gggatgagct gaccaagaac | 1080 |
| caggtcagcc tgtggtgcct ggtcaaaggc ttctatccca gcgacatcgc cgtggagtgg | 1140 |
| gagagcaatg gcagccgga gaacaactac aagaccacgc ctcccgtgtt ggactccgac | 1200 |
| ggctccttct cctctacag cgcgctcacc gtggacaaga gcaggtggca gcaggggaac | 1260 |
| gtcttctcat gctccgtgat gcatgaggct ctgcacaacc actacacgca gaagagcctc | 1320 |
| tccctgtctc cgggtaaa | 1338 |

<210> SEQ ID NO 53
<211> LENGTH: 3
<212> TYPE: PRT
<213> ORGANISM: Artificial Sequence
<220> FEATURE:
<223> OTHER INFORMATION: linker1

<400> SEQUENCE: 53

Gly Ala Pro
1

<210> SEQ ID NO 54
<211> LENGTH: 360
<212> TYPE: PRT
<213> ORGANISM: Artificial Sequence
<220> FEATURE:
<223> OTHER INFORMATION: amino acid sequence of hu56-Fc9

<400> SEQUENCE: 54

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Cys Arg Asp Glu Leu Thr
            260                 265                 270

Lys Asn Gln Val Ser Leu Trp Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Ala Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

```
Ser Leu Ser Leu Ser Pro Gly Lys
        355                 360
```

<210> SEQ ID NO 55
<211> LENGTH: 1473
<212> TYPE: DNA
<213> ORGANISM: Artificial Sequence
<220> FEATURE:
<223> OTHER INFORMATION: gene of hu56-Fc9

<400> SEQUENCE: 55

| | |
|---|---:|
| caggtgcagc tggtggagag cggcggcggc ctggtgcagc ccggcggcag cctgaggctg | 60 |
| agctgtgcag ccagcggcaa gatgagcagc aggaggtgca tggcctggtt taggcaggcc | 120 |
| cctggcaaag agcgggagag ggtggccaag ctgctgacaa ctagcggctc cacctacctg | 180 |
| gctgacagcg tgaaaggcag gttcaccatc agcagagaca cagcaaaaa caccgtgtac | 240 |
| ctgcagatga actccctgag ggccgaggac accgcagtgt actattgtgc tgcagactcc | 300 |
| ttcgaggacc ctacttgtac cctggtcact agcagcggcg catttcaata ctggggccag | 360 |
| ggaacactgg tgacagtgag ctccggcgcg ccacaggtgc agctggtgga gagcggcggc | 420 |
| ggcctggtgc agcccggcgg cagcctgagg ctgagctgtg cagccagcgg caagatgagc | 480 |
| agcaggaggt gcatggcctg gtttaggcag gcccctggca agagcgggga gagggtggcc | 540 |
| aagctgctga actagcgg ctccacctac ctggctgaca gcgtgaaagg caggttcacc | 600 |
| atcagcagag acaacagcaa aaacaccgtg tacctgcaga tgaactccct gagggccgag | 660 |
| gacaccgcag tgtactattg tgctgcagac tccttcgagg accctacttg taccctggtc | 720 |
| actagcagcg gcgcatttca atactgggc cagggaacac tggtgacagt gagctccgag | 780 |
| cctaagagca gcgacaaaac tcacacatgc ccaccgtgcc cagctccgga actcctgggc | 840 |
| ggaccgtcag tcttcctctt ccccccaaaa cccaaggaca cctcatgat ctcccggacc | 900 |
| cctgaggtca catgcgtggt ggtggacgtg agccacgaag accctgaggt caagttcaac | 960 |
| tggtacgtgg acggcgtgga ggtgcataat gccaagacaa agccgcggga ggagcagtac | 1020 |
| aacagcacgt accgtgtggt cagcgtcctc accgtcctgc accaggactg gctgaatggc | 1080 |
| aaggagtaca agtgcaaggt ctccaacaaa gccctcccag cccccatcga gaaaaccatc | 1140 |
| tccaaagcca aagggcagcc ccgagaacca caggtgtaca ccctgccccc atgtcgggat | 1200 |
| gagctgacca agaaccaggt cagcctgtgg tgcctggtca aaggcttcta tcccagcgac | 1260 |
| atcgccgtgg agtgggagag caatgggcag ccggagaaca actacaagac cacgcctccc | 1320 |
| gtgttggact ccgacggctc cttcttcctc tacagcgcgc tcaccgtgga caagagcagg | 1380 |
| tggcagcagg ggaacgtctt ctcatgctcc gtgatgcatg aggctctgca caaccactac | 1440 |
| acgcagaaga gcctctccct gtctccgggt aaa | 1473 |

<210> SEQ ID NO 56
<211> LENGTH: 491
<212> TYPE: PRT
<213> ORGANISM: Artificial Sequence
<220> FEATURE:
<223> OTHER INFORMATION: amino acid sequence of hu56di-Fc9

<400> SEQUENCE: 56

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30
```

```
Cys Met Ala Trp Phe Arg Gln Ala Pro Gly Lys Glu Arg Glu Arg Val
         35                  40                  45

Ala Lys Leu Leu Thr Thr Ser Gly Ser Thr Tyr Leu Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala Asp Ser Phe Glu Asp Pro Thr Cys Thr Leu Val Thr Ser Ser
             100                 105                 110

Gly Ala Phe Gln Tyr Trp Gly Gln Gly Thr Leu Val Thr Val Ser Ser
         115                 120                 125

Gly Ala Pro Gln Val Gln Leu Val Glu Ser Gly Gly Gly Leu Val Gln
     130                 135                 140

Pro Gly Gly Ser Leu Arg Leu Ser Cys Ala Ala Ser Gly Lys Met Ser
145                 150                 155                 160

Ser Arg Arg Cys Met Ala Trp Phe Arg Gln Ala Pro Gly Lys Glu Arg
                 165                 170                 175

Glu Arg Val Ala Lys Leu Leu Thr Thr Ser Gly Ser Thr Tyr Leu Ala
             180                 185                 190

Asp Ser Val Lys Gly Arg Phe Thr Ile Ser Arg Asp Asn Ser Lys Asn
         195                 200                 205

Thr Val Tyr Leu Gln Met Asn Ser Leu Arg Ala Glu Asp Thr Ala Val
     210                 215                 220

Tyr Tyr Cys Ala Ala Asp Ser Phe Glu Asp Pro Thr Cys Thr Leu Val
225                 230                 235                 240

Thr Ser Ser Gly Ala Phe Gln Tyr Trp Gly Gln Gly Thr Leu Val Thr
                 245                 250                 255

Val Ser Ser Glu Pro Lys Ser Ser Asp Lys Thr His Thr Cys Pro Pro
             260                 265                 270

Cys Pro Ala Pro Glu Leu Leu Gly Gly Pro Ser Val Phe Leu Phe Pro
         275                 280                 285

Pro Lys Pro Lys Asp Thr Leu Met Ile Ser Arg Thr Pro Glu Val Thr
     290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                 325                 330                 335

Glu Glu Gln Tyr Asn Ser Thr Tyr Arg Val Val Ser Val Leu Thr Val
             340                 345                 350

Leu His Gln Asp Trp Leu Asn Gly Lys Glu Tyr Lys Cys Lys Val Ser
         355                 360                 365

Asn Lys Ala Leu Pro Ala Pro Ile Glu Lys Thr Ile Ser Lys Ala Lys
     370                 375                 380

Gly Gln Pro Arg Glu Pro Gln Val Tyr Thr Leu Pro Pro Cys Arg Asp
385                 390                 395                 400

Glu Leu Thr Lys Asn Gln Val Ser Leu Trp Cys Leu Val Lys Gly Phe
                 405                 410                 415

Tyr Pro Ser Asp Ile Ala Val Glu Trp Glu Ser Asn Gly Gln Pro Glu
             420                 425                 430

Asn Asn Tyr Lys Thr Thr Pro Pro Val Leu Asp Ser Asp Gly Ser Phe
         435                 440                 445

Phe Leu Tyr Ser Ala Leu Thr Val Asp Lys Ser Arg Trp Gln Gln Gly
```

Asn Val Phe Ser Cys Ser Val Met His Glu Ala Leu His Asn His Tyr
465                 470                 475                 480

Thr Gln Lys Ser Leu Ser Leu Ser Pro Gly Lys
                485                 490

<210> SEQ ID NO 57
<211> LENGTH: 1473
<212> TYPE: DNA
<213> ORGANISM: Artificial Sequence
<220> FEATURE:
<223> OTHER INFORMATION: gene of hu56di-Fc9

<400> SEQUENCE: 57

| | |
|---|---|
| caggtgcagc tggtggagag cggcggcggc ctggtgcagc ccggcggcag cctgaggctg | 60 |
| agctgtgcag ccagcggcaa gatgagcagc aggaggtgca tggcctggtt taggcaggcc | 120 |
| cctggcaaag gcgggagag gtggccaag ctgctgacaa ctagcggctc cacctacctg | 180 |
| gctgacagcg tgaaaggcag gttcaccatc agcagagaca acagcaaaaa caccgtgtac | 240 |
| ctgcagatga actccctgag ggccgaggac accgcagtgt actattgtgc tgcagactcc | 300 |
| ttcgaggacc ctacttgtac cctggtcact agcagcggcg catttcaata ctggggccag | 360 |
| ggaacactgg tgacagtgag ctccggcgcg ccacaggtgc agctggtgga gagcggcggc | 420 |
| ggcctggtgc agcccggcgg cagcctgagg ctgagctgtg cagccagcgg caagatgagc | 480 |
| agcaggaggt gcatggcctg gtttaggcag gcccctggca agagcgggga gagggtggcc | 540 |
| aagctgctga caactagcgg ctccacctac ctggctgaca gcgtgaaagg caggttcacc | 600 |
| atcagcagag acaacagcaa aaacaccgtg tacctgcaga tgaactccct gagggccgag | 660 |
| gacaccgcag tgtactattg tgctgcagac tccttcgagg accctacttg taccctggtc | 720 |
| actagcagcg gcgcatttca atactggggc cagggaacac tggtgacagt gagctccgag | 780 |
| cctaagagca gcgacaaaac tcacacatgc ccaccgtgcc cagctccgga actcctgggc | 840 |
| ggaccgtcag tcttcctctt ccccccaaaa cccaaggaca cctcatgat ctcccggacc | 900 |
| cctgaggtca catgcgtggt ggtggacgtg agccacgaag accctgaggt caagttcaac | 960 |
| tggtacgtgg acggcgtgga ggtgcataat gccaagacaa agccgcggga ggagcagtac | 1020 |
| aacagcacgt accgtgtggt cagcgtcctc accgtcctgc accaggactg gctgaatggc | 1080 |
| aaggagtaca agtgcaaggt ctccaacaaa gccctcccag cccccatcga gaaaaccatc | 1140 |
| tccaaagcca agggcagcc cgagaaccca caggtgtaca ccctgccccc atgtcgggat | 1200 |
| gagctgacca gaaccaggt cagcctgtgg tgcctggtca aaggcttcta tcccagcgac | 1260 |
| atcgccgtgg agtgggagag caatgggcag ccggagaaca actacaagac cacgcctccc | 1320 |
| gtgttggact ccgacggctc cttcttcctc tacagcgcgc tcaccgtgga caagagcagg | 1380 |
| tggcagcagg gaacgtcttt ctcatgctcc gtgatgcatg aggctctgca caaccactac | 1440 |
| acgcagaaga gcctctccct gtctccgggt aaa | 1473 |

<210> SEQ ID NO 58
<211> LENGTH: 5
<212> TYPE: PRT
<213> ORGANISM: Artificial Sequence
<220> FEATURE:
<223> OTHER INFORMATION: linker 2

<400> SEQUENCE: 58

Glu Pro Lys Ser Ser

<210> SEQ ID NO 59
<211> LENGTH: 478
<212> TYPE: PRT
<213> ORGANISM: Artificial Sequence
<220> FEATURE:
<223> OTHER INFORMATION: amino acid sequences of mPD-L1-scFv-Fc9

<400> SEQUENCE: 59

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Thr
            20                  25                  30

Lys Ala Ala Trp Tyr Trp Ile Arg Gln Ser Pro Ser Arg Gly Leu Glu
        35                  40                  45

Trp Leu Gly Arg Thr Tyr Phe Arg Ser Lys Trp Tyr Asn Asp Tyr Ala
    50                  55                  60

Asp Ser Val Lys Ser Arg Leu Thr Ile Asn Pro Asp Thr Ser Lys Asn
65                  70                  75                  80

Gln Phe Ser Leu Gln Leu Lys Ser Val Ser Pro Glu Asp Thr Ala Val
                85                  90                  95

Tyr Tyr Cys Ala Arg Gly Gln Tyr Thr Ala Phe Asp Ile Trp Gly Gln
            100                 105                 110

Gly Thr Met Val Thr Val Ser Ser Gly Ile Leu Gly Ser Gly Gly Gly
        115                 120                 125

Gly Ser Gly Gly Gly Gly Ser Gly Gly Gly Gly Ser Gln Ser Ala Leu
    130                 135                 140

Ile Gln Pro Ala Ser Val Ser Gly Ser Pro Gly Gln Ser Ile Thr Ile
145                 150                 155                 160

Ser Cys Thr Gly Thr Ser Ser Asp Val Gly Gly Tyr Asp Leu Val Ser
                165                 170                 175

Trp Tyr Gln Gln Tyr Pro Gly Gln Ala Pro Arg Leu Ile Ile Tyr Glu
            180                 185                 190

Val Ile Lys Arg Pro Ser Gly Ile Ser Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Cys Ser Tyr Ala Gly Arg Arg Leu His Gly
225                 230                 235                 240

Val Phe Gly Gly Gly Thr Gln Leu Thr Val Leu Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
```

```
                    355                 360                 365
Lys Ala Lys Gly Gln Pro Arg Glu Pro Gln Val Tyr Thr Leu Pro Pro
            370                 375                 380
Ser Arg Asp Glu Leu Thr Lys Asn Gln Val Ser Leu Trp Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Val Leu Asp Ser Asp
            420                 425                 430
Gly Ser Phe Phe Leu Tyr Ser Ala Leu Thr Val Asp Lys Ser Arg Trp
                435                 440                 445
Gln Gln Gly Asn Val Phe Ser Cys Ser Val Met His Glu Ala Leu His
            450                 455                 460
Asn His Tyr Thr Gln Lys Ser Leu Ser Leu Ser Pro Gly Lys
465                 470                 475

<210> SEQ ID NO 60
<211> LENGTH: 1434
<212> TYPE: DNA
<213> ORGANISM: Artificial Sequence
<220> FEATURE:
<223> OTHER INFORMATION: gene of mPD-L1-scFv-Fc9

<400> SEQUENCE: 60
caggtacagc tgcagcagtc aggtccagga ctggtgaagc cctcgcagac cctctcactc      60
acctgtgcca tctccgggga cagtgtctct agcaccaagg ctgcttggta ctggatcagg     120
cagtccccct tcgagaggcc tgagtggctg ggaaggacat acttccggtc caagtggtat     180
aatgactatg ccgactctgt gaaaagtcga ttaaccatca cccagacaca tccaagaac      240
cagttctccc tgcaacttaa gtctgtgagt cccgaggaca cggctgtgta ttactgtgca     300
agagggcaat acactgcttt tgatatctgg ggccaaggga caatggtcac cgtctcttca     360
ggaattctag atccggtggc ggtggcagcg gcggtggtg gttccggagg cggcggttct     420
cagtctgctc tgattcagcc tgcctccgtg tctgggtccc ctggacagtc gatcactatc     480
tcctgtactg gcaccagtag tgatgttgga ggttatgacc ttgtctcctg gtaccaacag     540
tacccgggcc aagcccccag actcatcatt tatgaggtca ttaagcggcc ctcagggatt     600
tctgatcgct tctctggttc caagtctggc aacacgcct cctgacaat ctctgggctc      660
caggctgagg acgaggctga ttattattgc tgctcatatg caggtagacg tcttcatggt     720
gtgttcggag gaggcaccca gctgaccgtc ctcgacaaaa ctcacacatg cccaccgtgc     780
ccagctccgg aactcctggg cggaccgtca gtcttcctct tccccccaaa acccaaggac     840
accctcatga tctcccggac ccctgaggtc acatgcgtgg tggtggacgt gagccacgaa     900
gaccctgagg tcaagttcaa ctggtacgtg gacggcgtgg aggtgcataa tgccaagaca     960
aagccgcggg aggagcagta acagcacg taccgtgtgg tcagcgtcct caccgtcctg     1020
caccaggact ggctgaatgg caaggagtac aagtgcaagg tctccaacaa agccctccca    1080
gcccccatcg agaaaaccat ctccaaagcc aaagggcagc cccgagaacc acaggtgtac    1140
accctgcccc caagtcggga tgagctgacc aagaaccagg tcagcctgtg tgcctggtc     1200
aaaggcttct atcccagcga catcgccgtg gagtgggaga gcaatgggca gccggagaac    1260
aactacaaga ccacgcctcc cgtgttggac tccgacggct ccttcttcct ctacagcgcg    1320
ctcaccgtgg acaagagcag gtggcagcag gggaacgtct tctcatgctc cgtgatgcat    1380
```

```
gaggctctgc acaaccacta cacgcagaag agcctctccc tgtctccggg taaa         1434
```

\<210\> SEQ ID NO 61
\<211\> LENGTH: 351
\<212\> TYPE: PRT
\<213\> ORGANISM: Artificial Sequence
\<220\> FEATURE:
\<223\> OTHER INFORMATION: amino acid sequences of CD47-muFc

\<400\> SEQUENCE: 61

```
Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Met Asp Pro Lys Ser Ser Asp
        115                 120                 125

Lys Thr His Thr Cys Pro Pro Cys Pro Ala Pro Glu Val Ser Ser Val
    130                 135                 140

Phe Ile Phe Pro Pro Lys Pro Lys Asp Val Leu Thr Ile Thr Leu Thr
145                 150                 155                 160

Pro Lys Val Thr Cys Val Val Asp Ile Ser Lys Asp Asp Pro Glu
                165                 170                 175

Val Gln Phe Ser Trp Phe Val Asp Asp Val Glu Val His Thr Ala Gln
            180                 185                 190

Thr Gln Pro Arg Glu Glu Gln Phe Asn Ser Thr Phe Arg Ser Val Ser
        195                 200                 205

Glu Leu Pro Ile Met His Gln Asp Trp Leu Asn Gly Lys Glu Phe Lys
    210                 215                 220

Cys Arg Val Asn Ser Ala Ala Phe Pro Ala Pro Ile Glu Lys Thr Ile
225                 230                 235                 240

Ser Lys Thr Lys Gly Arg Pro Lys Ala Pro Gln Val Tyr Thr Ile Pro
                245                 250                 255

Pro Pro Lys Glu Gln Met Ala Lys Asp Lys Val Ser Leu Thr Cys Met
            260                 265                 270

Ile Thr Asp Phe Phe Pro Glu Asp Ile Thr Val Glu Trp Gln Trp Asn
        275                 280                 285

Gly Gln Pro Ala Glu Asn Tyr Lys Asn Thr Gln Pro Ile Met Asn Thr
    290                 295                 300

Asn Gly Ser Tyr Phe Val Tyr Ser Lys Leu Asn Val Gln Lys Ser Asn
305                 310                 315                 320

Trp Glu Ala Gly Asn Thr Phe Thr Cys Ser Val Leu His Glu Gly Leu
                325                 330                 335

His Asn His His Thr Glu Lys Ser Leu Ser His Ser Pro Gly Lys
            340                 345                 350
```

<210> SEQ ID NO 62
<211> LENGTH: 1053
<212> TYPE: DNA
<213> ORGANISM: Artificial Sequence
<220> FEATURE:
<223> OTHER INFORMATION: gene of CD47-muFc

<400> SEQUENCE: 62

```
cagctactat ttaataaaac aaaatctgta gaattcacgt tttgtaatga cactgtcgtc    60
attccatgct tgttactaa tatggaggca caaaacacta ctgaagtata cgtaaagtgg    120
aaatttaaag gaagagatat ttacaccttt gatggagctc taaacaagtc cactgtcccc    180
actgacttta gtagtgcaaa aattgaagtc tcacaattac taaaaggaga tgcctctttg    240
aagatggata agagtgatgc tgtctcacac acaggaaact acacttgtga agtaacagaa    300
ttaaccagag aaggtgaaac gatcatcgag ctaaaatatc gtgttgtttc atggttttct    360
ccaatggatc gaaatcctc tgacaaaact cacacatgcc caccgtgccc agctccggaa    420
gtatcatctg tcttcatctt ccccccaaag cccaaggatg tgctcaccat tactctgact    480
cctaaggtca cgtgtgttgt ggtagacatc agcaaggatg atcccgaggt ccagttcagc    540
tggtttgtag atgatgtgga ggtgcacaca gctcagacgc aaccccggga ggagcagttc    600
aacagcactt tccgctcagt cagtgaactt cccatcatgc accaggactg gctcaatggc    660
aaggagttca atgcagggt caacagtgca gctttccctg cccccatcga gaaaaccatc    720
tccaaaacca aggcagacc gaaggctcca caggtgtaca ccattccacc tcccaaggag    780
cagatggcca aggataaagt cagtctgacc tgcatgataa cagacttctt ccctgaagac    840
attactgtgg agtggcagtg gaatgggcag ccagcggaga actacaagaa cactcagccc    900
atcatgaaca cgaatggctc ttacttcgtc tacagcaagc tcaatgtgca gaagagcaac    960
tgggaggcag gaaatacttt cacctgctct gtgttacatg agggcctgca caaccaccat    1020
actgagaaga gcctctccca ctctcctggg aaa    1053
```

<210> SEQ ID NO 63
<211> LENGTH: 550
<212> TYPE: PRT
<213> ORGANISM: Artificial Sequence
<220> FEATURE:
<223> OTHER INFORMATION: amino acid sequences of CD47-EGFP

<400> SEQUENCE: 63

```
Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
        115                 120                 125
```

```
Ile Phe Pro Ile Phe Ala Ile Leu Leu Phe Trp Gly Gln Phe Gly Ile
130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
            165                 170                 175

Ile Leu Phe Val Pro Gly Glu Tyr Ser Leu Lys Asn Ala Thr Gly Leu
            180                 185                 190

Gly Leu Ile Val Thr Ser Thr Gly Ile Leu Ile Leu Leu His Tyr Tyr
            195                 200                 205

Val Phe Ser Thr Ala Ile Gly Leu Thr Ser Phe Val Ile Ala Ile Leu
210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
            260                 265                 270

Phe Val Ala Ser Asn Gln Lys Thr Ile Gln Pro Pro Arg Lys Ala Val
            275                 280                 285

Glu Glu Pro Leu Asn Ala Phe Lys Glu Ser Lys Gly Met Met Asn Asp
290                 295                 300

Glu Gly Ala Pro Gly Gly Met Val Ser Lys Gly Glu Glu Leu Phe
305                 310                 315                 320

Thr Gly Val Val Pro Ile Leu Val Glu Leu Asp Gly Asp Val Asn Gly
                325                 330                 335

His Lys Phe Ser Val Ser Gly Glu Gly Glu Gly Asp Ala Thr Tyr Gly
            340                 345                 350

Lys Leu Thr Leu Lys Phe Ile Cys Thr Thr Gly Lys Leu Pro Val Pro
            355                 360                 365

Trp Pro Thr Leu Val Thr Thr Leu Thr Tyr Gly Val Gln Cys Phe Ser
370                 375                 380

Arg Tyr Pro Asp His Met Lys Gln His Asp Phe Phe Lys Ser Ala Met
385                 390                 395                 400

Pro Glu Gly Tyr Val Gln Glu Arg Thr Ile Phe Phe Lys Asp Asp Gly
            405                 410                 415

Asn Tyr Lys Thr Arg Ala Glu Val Lys Phe Glu Gly Asp Thr Leu Val
            420                 425                 430

Asn Arg Ile Glu Leu Lys Gly Ile Asp Phe Lys Glu Asp Gly Asn Ile
            435                 440                 445

Leu Gly His Lys Leu Glu Tyr Asn Tyr Asn Ser His Asn Val Tyr Ile
450                 455                 460

Met Ala Asp Lys Gln Lys Asn Gly Ile Lys Val Asn Phe Lys Ile Arg
465                 470                 475                 480

His Asn Ile Glu Asp Gly Ser Val Gln Leu Ala Asp His Tyr Gln Gln
            485                 490                 495

Asn Thr Pro Ile Gly Asp Gly Pro Val Leu Leu Pro Asp Asn His Tyr
            500                 505                 510

Leu Ser Thr Gln Ser Ala Leu Ser Lys Asp Pro Asn Glu Lys Arg Asp
            515                 520                 525

His Met Val Leu Leu Glu Phe Val Thr Ala Ala Gly Ile Thr Leu Gly
530                 535                 540

Met Asp Glu Leu Tyr Lys
```

<210> SEQ ID NO 64
<211> LENGTH: 1650
<212> TYPE: DNA
<213> ORGANISM: Artificial Sequence
<220> FEATURE:
<223> OTHER INFORMATION: gene of CD47-EGFP

<400> SEQUENCE: 64

```
cagctactat ttaataaaac aaaatctgta gaattcacgt tttgtaatga cactgtcgtc      60
attccatgct tgttactaa tatggaggca caaaacacta ctgaagtata cgtaaagtgg     120
aaatttaaag gaagagatat ttacaccttt gatggagctc taaacaagtc cactgtcccc    180
actgacttta gtagtgcaaa aattgaagtc tcacaattac taaaaggaga tgcctctttg    240
aagatggata agagtgatgc tgtctcacac acaggaaact acacttgtga agtaacagaa    300
ttaaccagag aaggtgaaac gatcatcgag ctaaaatatc gtgttgtttc atggtttct     360
ccaaatgaaa atattcttat tgttattttc ccaattttg ctatactcct gttctgggga    420
cagtttggta ttaaaacact taaatataga tccggtggta tggatgagaa aacaattgct    480
ttacttgttg ctggactagt gatcactgtc attgtcattg ttggagccat tcttttcgtc    540
ccaggtgaat attcattaaa gaatgctact ggccttggtt taattgtgac ttctacaggg    600
atattaatat tacttcacta ctatgtgttt agtacagcga ttggattaac ctccttcgtc    660
attgccatat tggttattca ggtgatagcc tatatcctcg ctgtggttgg actgagtctc    720
tgtattgcgg cgtgtatacc aatgcatggc cctcttctga tttcaggttt gagtatctta    780
gctctagcac aattacttgg actagtttat atgaaatttg tggcttccaa tcagaagact    840
atacaacctc ctaggaaagc tgtagaggaa ccccttaatg cattcaaaga atcaaaagga    900
atgatgaatg atgaaggcgc gccaggaggt ggtatggtga gcaagggcga ggagctgttc    960
accggggtgg tgcccatcct ggtcgagctg gacggcgacg taaacggcca caagttcagc   1020
gtgtccggcg agggcgaggg cgatgccacc tacggcaagc tgaccctgaa gttcatctgc   1080
accaccggca agctgcccgt gccctggccc accctcgtga ccaccctgac ctacggcgtg   1140
cagtgcttca gccgctaccc cgaccacatg aagcagcacg acttcttcaa gtccgccatg   1200
cccgaaggct acgtccagga gcgcaccatc ttcttcaagg acgacggcaa ctacaagacc   1260
cgcgccgagg tgaagttcga gggcgacacc ctggtgaacc gcatcgagct gaagggcatc   1320
gacttcaagg aggacggcaa catcctgggg cacaagctgg agtacaacta caacagccac   1380
aacgtctata tcatggccga caagcagaag aacggcatca aggtgaactt caagatccgc   1440
cacaacatcg aggacggcag cgtgcagctc gccgaccact accagcagaa cacccccatc   1500
ggcgacggcc ccgtgctgct gcccgacaac cactacctga gcacccagtc cgccctgagc   1560
aaagacccca acgagaagcg cgatcacatg gtcctgctgg agttcgtgac cgccgccggg   1620
atcactctcg gcatggacga gctgtacaag                                     1650
```

<210> SEQ ID NO 65
<211> LENGTH: 5
<212> TYPE: PRT
<213> ORGANISM: Artificial Sequence
<220> FEATURE:
<223> OTHER INFORMATION: linker3

<400> SEQUENCE: 65

Gly Gly Gly Gly Ser

<210> SEQ ID NO 66
<211> LENGTH: 350
<212> TYPE: PRT
<213> ORGANISM: Artificial Sequence
<220> FEATURE:
<223> OTHER INFORMATION: amino acid sequence of SIRP-Fc6

<400> SEQUENCE: 66

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Gly Gly Gly Ser Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Ser Cys Gly Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Lys Leu Ala Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350
```

```
<210> SEQ ID NO 67
<211> LENGTH: 1050
<212> TYPE: DNA
<213> ORGANISM: Artificial Sequence
<220> FEATURE:
<223> OTHER INFORMATION: gene of SIRP-Fc6

<400> SEQUENCE: 67
gaggaggagc tgcaggtgat ccagcccgac aagagcgtgt ccgtggctgc cggagagagc      60
gccatcctgc actgcaccgt gacaagcctg atccccgtgg gccccatcca gtggttcaga     120
ggagccggcc ctgccaggga gctgatctac aaccagaagg agggccactt ccccagggtg     180
accaccgtga gcgagagcac caagagggag aacatggact tagcatcag catcagcaac      240
atcaccccccg ccgacgccgg aacctactac tgcgtgaagt tcaggaaggg cagccccgac     300
accgagttca gagcggagc cggcacagag ctgagcgtga gggccaagcc cagcggaggc      360
ggtggatcag acaagaccca cacttgcccc ccttgtcccg ctccggaact cctgggcgga     420
ccgtcagtct tcctcttccc cccaaaaccc aaggacaccc tcatgatctc ccggaccct      480
gaggtcacat gcgtggtggt ggacgtgagc cacgaagacc ctgaggtcaa gttcaactgg     540
tacgtggacg gcgtggaggt gcataatgcc aagacaaagc cgcgggagga gcagtacaac     600
agcacgtacc gtgtggtcag cgtcctcacc gtcctgcacc aggactggct gaatggcaag     660
gagtacaagt gcaaggtctc caacaaagcc ctcccagccc ccatcgagaa aaccatctcc     720
aaagccaaag ggcagccccg agaaccacag gtgtataccc tgcccccatc ccgggatgag     780
ctgaccaaga accaggtcag cctgagttgc ggggtcaaag gcttctatcc cagcgacatc     840
gccgtggagt gggagagcaa tgggcagccg gagaacaact acaagaccac gcctcccgtg     900
ttggactccg acggctcctt caagctcgcc agcaagctca ccgtggacaa gagcaggtgg     960
cagcagggga acgtcttctc atgctccgtg atgcatgagg ctctgcacaa ccactacacg    1020
cagaagagcc tctccctgtc tccgggtaaa                                      1050

<210> SEQ ID NO 68
<211> LENGTH: 5
<212> TYPE: PRT
<213> ORGANISM: Artificial Sequence
<220> FEATURE:
<223> OTHER INFORMATION: linker4

<400> SEQUENCE: 68

Gly Ala Pro Gly Gly
1               5

<210> SEQ ID NO 69
<211> LENGTH: 350
<212> TYPE: PRT
<213> ORGANISM: Artificial Sequence
<220> FEATURE:
<223> OTHER INFORMATION: amino acid sequence of SIRP-Fc IgG1

<400> SEQUENCE: 69

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60
```

```
Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser Gly Ala Pro Gly Gly Asp Lys Thr His Thr
        115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 70
<211> LENGTH: 1050
<212> TYPE: DNA
<213> ORGANISM: Artificial Sequence
<220> FEATURE:
<223> OTHER INFORMATION: gene of SIRP-Fc IgG1

<400> SEQUENCE: 70
gaggaggagc tgcaggtgat ccagcccgac aagagcgtgt ccgtggctgc cggagagagc      60
gccatcctgc actgcaccgt gacaagcctg atccccgtgg gccccatcca gtggttcaga     120
ggagccggcc ctgccaggga gctgatctac aaccagaagg agggccactt ccccagggtg     180
accaccgtga gcgagagcac caagagggag aacatggact ttagcatcag catcagcaac     240
atcacccccg ccgacgccgg aacctactac tgcgtgaagt tcaggaaggg cagccccgac     300
accgagttca agagcggagc cggcacagag ctgagcgtga gggccaagcc cagcggcgcg     360
ccaggaggtg acaaaactca cacatgccca ccgtgcccag caccgaaact cctgggcgga     420
```

```
ccgtcagtct tcctcttccc cccaaaaccc aaggacaccc tcatgatctc ccggacccct    480
gaggtcacat gcgtggtggt ggacgtgagc cacgaagacc ctgaggtcaa gttcaactgg    540
tacgtggacg gcgtggaggt gcataatgcc aagacaaagc cgcgggagga gcagtacaac    600
agcacgtacc gtgtggtcag cgtcctcacc gtcctgcacc aggactggct gaatggcaag    660
gagtacaagt gcaaggtctc caacaaagcc ctcccagccc ccatcgagaa aaccatctcc    720
aaagccaaag gcagccccg agaaccacag gtgtacaccc tgcccccatc ccgggatgag    780
ctgaccaaga accaggtcag cctgacctgc ctggtcaaag gcttctatcc cagcgacatc    840
gccgtggagt gggagagcaa tgggcagccg gagaacaact acaagaccac gcctcccgtg    900
ttggactccg acggctcctt cttcctctac agcaagctca ccgtggacaa gagcaggtgg    960
cagcagggga acgtcttctc atgctccgtg atgcatgagg ctctgcacaa ccactacacg   1020
cagaagagcc tctccctgtc tccgggtaaa                                    1050
```

<210> SEQ ID NO 71
<211> LENGTH: 15
<212> TYPE: PRT
<213> ORGANISM: Artificial Sequence
<220> FEATURE:
<223> OTHER INFORMATION: linker5

<400> SEQUENCE: 71

Gly Gly Gly Gly Ser Gly Gly Gly Gly Ser Gly Gly Gly Gly Ser
1               5                   10                  15

<210> SEQ ID NO 72
<211> LENGTH: 493
<212> TYPE: PRT
<213> ORGANISM: Artificial Sequence
<220> FEATURE:
<223> OTHER INFORMATION: amino acid sequence of hu56-Fc6-SIRP

<400> SEQUENCE: 72

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
                20                  25                  30

Cys Met Ala Trp Phe Arg Gln Ala Pro Gly Lys Glu Arg Glu Arg Val
            35                  40                  45

Ala Lys Leu Leu Thr Thr Ser Gly Ser Thr Tyr Leu Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val

```
            180                 185                 190
Asp Gly Val Glu Val His Asn Ala Lys Thr Lys Pro Arg Glu Glu Gln
            195                 200                 205

Tyr Asn Ser Thr Tyr Arg Val Ser Val Leu Thr Val Leu His Gln
            210                 215             220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Ser Cys Gly Val Lys Gly Phe Tyr Pro Ser
            275                 280                 285

Asp Ile Ala Val Glu Trp Glu Ser Asn Gly Gln Pro Glu Asn Asn Tyr
            290                 295                 300

Lys Thr Thr Pro Pro Val Leu Asp Ser Asp Gly Ser Phe Lys Leu Ala
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys Gly Gly Gly Ser Gly Gly Gly
            355                 360                 365

Gly Ser Gly Gly Gly Gly Ser Glu Glu Glu Leu Gln Val Ile Gln Pro
            370                 375                 380

Asp Lys Ser Val Ser Val Ala Ala Gly Glu Ser Ala Ile Leu His Cys
385                 390                 395                 400

Thr Val Thr Ser Leu Ile Pro Val Gly Pro Ile Gln Trp Phe Arg Gly
                405                 410                 415

Ala Gly Pro Ala Arg Glu Leu Ile Tyr Asn Gln Lys Glu Gly His Phe
            420                 425                 430

Pro Arg Val Thr Thr Val Ser Glu Ser Thr Lys Arg Glu Asn Met Asp
            435                 440                 445

Phe Ser Ile Ser Ile Ser Asn Ile Thr Pro Ala Asp Ala Gly Thr Tyr
450                 455                 460

Tyr Cys Val Lys Phe Arg Lys Gly Ser Pro Asp Thr Glu Phe Lys Ser
465                 470                 475                 480

Gly Ala Gly Thr Glu Leu Ser Val Arg Ala Lys Pro Ser
                485                 490

<210> SEQ ID NO 73
<211> LENGTH: 1479
<212> TYPE: DNA
<213> ORGANISM: Artificial Sequence
<220> FEATURE:
<223> OTHER INFORMATION: gene of hu56-Fc6-SIRP

<400> SEQUENCE: 73
caggtgcagc tggtggagag cggcggcggc ctggtgcagc ccggcggcag cctgaggctg      60
agctgtgcag ccagcggcaa gatgagcagc aggaggtgca tggcctggtt taggcaggcc     120
cctggcaaag agcgggagag ggtggccaag ctgctgacaa ctagcggctc cacctacctg     180
gctgacagcg tgaaaggcag gttcaccatc agcagagaca cagcaaaaa caccgtgtac     240 ctgcagatga actccctgag ggccgaggac accgcagtgt actattgtgc tgcagactcc     300
```

```
ttcgaggacc ctacttgtac cctggtcact agcagcggcg catttcaata ctggggccag    360
ggaacactgg tgacagtgag ctccgagcct aagagcagcg acaaaactca cacatgccca    420
ccgtgcccag ctccggaact cctgggcgga ccgtcagtct tcctcttccc cccaaaaccc    480
aaggacaccc tcatgatctc ccggaccccc gaggtcacat gcgtggtggt ggacgtgagc    540
cacgaagacc ctgaggtcaa gttcaactgg tacgtggacg gcgtggaggt gcataatgcc    600
aagacaaagc cgcgggagga gcagtacaac agcacgtacc gtgtggtcag cgtcctcacc    660
gtcctgcacc aggactggct gaatggcaag gagtacaagt gcaaggtctc caacaaagcc    720
ctcccagccc ccatcgagaa aaccatctcc aaagccaaag ggcagccccg agaaccacag    780
gtgtataccc tgcccccatc ccgggatgag ctgaccaaga accaggtcag cctgagttgc    840
ggggtcaaag gcttctatcc cagcgacatc gccgtggagt gggagagcaa tgggcagccg    900
gagaacaact acaagaccac gcctcccgtg ttggactccg acggctcctt caagctcgcc    960
agcaagctca ccgtggacaa gagcaggtgg cagcagggga acgtcttctc atgctccgtg   1020
atgcatgagg ctctgcacaa ccactacacg cagaagagcc tctccctgtc tccgggtaaa   1080
ggcggcggcg gcagcggggg cggcggcagc ggaggaggcg gcagcgagga ggagctgcag   1140
gtgatccagc ccgacaagag cgtgtccgtg gctgccggag agagcgccat cctgcactgc   1200
accgtgacaa gcctgatccc cgtgggcccc atccagtggt tcagaggagc cggccctgcc   1260
agggagctga tctacaacca gaaggagggc cacttcccca gggtgaccac cgtgagcgag   1320
agcaccaaga gggagaacat ggactttagc atcagcatca gcaacatcac ccccgccgac   1380
gccggaacct actactgcgt gaagttcagg aagggcagcc ccgacaccga gttcaagagc   1440
ggagccggca cagagctgag cgtgagggcc aagcccagc                          1479
```

<210> SEQ ID NO 74
<211> LENGTH: 214
<212> TYPE: PRT
<213> ORGANISM: Artificial Sequence
<220> FEATURE:
<223> OTHER INFORMATION: ate-LC

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 75
<211> LENGTH: 642
<212> TYPE: DNA
<213> ORGANISM: Artificial Sequence
<220> FEATURE:
<223> OTHER INFORMATION: gene of ate-LC

<400> SEQUENCE: 75

```
gacatccaga tgacccagag ccccagcagc ctgagcgcca gcgtgggcga ccgcgtgacc      60
atcacctgcc gcgccagcca ggacgtgagc accgccgtgg cctggtacca gcagaagccc     120
ggcaaggccc ccaagctgct gatctacagc gccagcttcc tgtacagcgg cgtgcccagc     180
cgcttcagcg gcagcggcag cggcaccgac ttcaccctga ccatcagcag cctgcagccc     240
gaggacttcg ccacctacta ctgccagcag tacctgtacc accccgccac cttcggccag     300
ggcaccaagg tggagatcaa gcgcaccgtg gccgccccca gcgtgttcat cttccccccc     360
agcgacgagc agctgaagag cggcaccgcc agcgtggtgt gcctgctgaa caacttctac     420
ccccgcgagg ccaaggtgca gtggaaggtg gacaacgccc tgcagagcgg caacagccag     480
gagagcgtga ccgagcagga cagcaaggac agcacctaca gcctgagcag caccctgacc     540
ctgagcaagg ccgactacga aagcacaag gtgtacgcct gcgaggtgac ccaccagggc     600
ctgagcagcc ccgtgaccaa gagcttcaac cgcggcgagt gc                        642
```

<210> SEQ ID NO 76
<211> LENGTH: 448
<212> TYPE: PRT
<213> ORGANISM: Artificial Sequence
<220> FEATURE:
<223> OTHER INFORMATION: ate-Fc9

<400> SEQUENCE: 76

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125
```

Leu Ala Pro Ser Ser Lys Ser Thr Ser Gly Gly Thr Ala Ala Leu Gly
         130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Ala Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 77
<211> LENGTH: 1344
<212> TYPE: DNA
<213> ORGANISM: Artificial Sequence
<220> FEATURE:
<223> OTHER INFORMATION: gene of ate-Fc9

<400> SEQUENCE: 77
gaggtgcagc tggtggagag cggcggcggc ctggtgcagc ccggcggcag cctgcgcctg      60
agctgcgccg ccagcggctt caccttcagc gacagctgga tccactgggt gcgccaggcc     120
cccggcaagg gcctggagtg ggtggcctgg atcagcccct acggcggcag cacctactac     180
gccgacagcg tgaagggccg cttcaccatc agcgccgaca ccagcaagaa caccgcctac     240
ctgcagatga acagcctgcg cgccgaggac accgccgtgt actactgcgc ccgccgccac     300

```
tggcccggcg gcttcgacta ctggggccag ggcaccctgg tgaccgtgag cagcgccagc    360
actaaggggc cctctgtgtt tccactcgcc ccttctagca aaagcacttc cggaggaact    420
gccgctctgg gctgtctggt gaaagattac ttccccgaac cagtcactgt gtcatggaac    480
tctggagcac tgacatctgg agttcacacc tttcctgctg tgctgcagag ttctggactg    540
tactccctgt catctgtggt caccgtgcca tcttcatctc tggggaccca gacctacatc    600
tgtaacgtga accacaaacc ctccaacaca aaagtggaca aacgagtcga accaaaatct    660
tgtgacaaaa cccacacatg cccaccgtgc ccagctccgg aactcctggg cggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc caagtcggga tgagctgacc   1080
aagaaccagg tcagcctgtg tgtgcctggtc aaaggcttct atcccagcga catcgccgtg   1140
gagtgggaga gcaatgggca gccggagaac aactacaaga ccacgcctcc cgtgttggac   1200
tccgacggct ccttcttcct ctacagcgcg ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 78
<211> LENGTH: 216
<212> TYPE: PRT
<213> ORGANISM: Artificial Sequence
<220> FEATURE:
<223> OTHER INFORMATION: ave-LC

<400> SEQUENCE: 78

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
        210                 215

<210> SEQ ID NO 79
<211> LENGTH: 648
<212> TYPE: DNA
<213> ORGANISM: Artificial Sequence
<220> FEATURE:
<223> OTHER INFORMATION: gene of ave-LC

<400> SEQUENCE: 79
cagagcgccc tgacccagcc cgccagcgtg agcggcagcc ccggccagag catcaccatc    60
agctgcaccg gcaccagcag cgacgtgggc ggctacaact acgtgagctg gtaccagcag   120
caccccggca aggcccccaa gctgatgatc tacgacgtga gcaaccgccc cagcggcgtg   180
agcaaccgct tcagcggcag caagagcggc aacaccgcca gcctgaccat cagcggcctg   240
caggccgagg acgaggccga ctactactgc agcagctaca ccagcagcag cacccgcgtg   300
ttcggcaccg gcaccaaggt gaccgtgctg ggccagccca aggccaaccc caccgtgacc   360
ctgttccccc ccagcagcga ggagctgcag gccaacaagg ccaccctggt gtgcctgatc   420
agcgacttct accccggcgc cgtgaccgtg gcctggaagg ccgacggcag ccccgtgaag   480
gccggcgtgg agaccaccaa gcccagcaag cagagcaaca acaagtacgc cgccagcagc   540
tacctgagcc tgacccccga gcagtggaag agccaccgca gctacagctg ccaggtgacc   600
cacgagggca gcaccgtgga gaagaccgtg gcccccaccg agtgcagc                648

<210> SEQ ID NO 80
<211> LENGTH: 450
<212> TYPE: PRT
<213> ORGANISM: Artificial Sequence
<220> FEATURE:
<223> OTHER INFORMATION: ave-Fc9

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Ala Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 81
<211> LENGTH: 1350
<212> TYPE: DNA
<213> ORGANISM: Artificial Sequence
<220> FEATURE:
<223> OTHER INFORMATION: gene of ave-Fc9

<400> SEQUENCE: 81
gaggtgcagc tgctggagag cggcggcggc ctggtgcagc ccggcggcag cctgcgcctg      60
agctgcgccg ccagcggctt caccttcagc agctacatca tgatgtgggt gcgccaggcc    120
cccggcaagg gcctggagtg ggtgagcagc atctacccca gcggcggcat caccttctac    180
gccgacaccc tgaagggccg cttcaccatc agcgcgaca acagcaagaa cacccctgtac   240 ctgcagatga acagcctgcg cgccgaggac accgccgtgt actactgcgc ccgcatcaag    300
```

```
ctgggcaccg tgaccaccgt ggactactgg ggccagggca ccctggtgac cgtgagcagc    360
gccagcacta agggccctc tgtgtttcca ctcgcccctt ctagcaaaag cacttccgga     420
ggaactgccg ctctgggctg tctggtgaaa gattacttcc ccgaaccagt cactgtgtca    480
tggaactctg gagcactgac atctggagtt cacacctttc ctgctgtgct gcagagttct    540
ggactgtact ccctgtcatc tgtggtcacc gtgccatctt catctctggg acccagacc    600
tacatctgta acgtgaacca caaaccctcc aacacaaaag tggacaaacg agtcgaacca    660
aaatcttgtg acaaaaccca cacatgccca ccgtgcccag ctccggaact cctgggcgga    720
ccgtcagtct tcctcttccc cccaaaaccc aaggacaccc tcatgatctc ccggaccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc    1020
aaagccaaag ggcagccccg agaaccacag gtgtacaccc tgcccccaag tcgggatgag    1080
ctgaccaaga accaggtcag cctgtggtgc ctggtcaaag cttctatcc agcgacatc     1140
gccgtggagt gggagagcaa tgggcagccg gagaacaact acaagaccac gcctcccgtg    1200
ttggactccg acggctcctt cttcctctac agcgcgctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                    1350
```

<210> SEQ ID NO 82
<211> LENGTH: 215
<212> TYPE: PRT
<213> ORGANISM: Artificial Sequence
<220> FEATURE:
<223> OTHER INFORMATION: dur-LC

<400> SEQUENCE: 82

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
                20                  25                  30

Tyr Leu Ala Trp Tyr Gln Gln Lys Pro Gly Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 83
<211> LENGTH: 645
<212> TYPE: DNA
<213> ORGANISM: Artificial Sequence
<220> FEATURE:
<223> OTHER INFORMATION: gene of dur-LC

<400> SEQUENCE: 83

| | | |
|---|---|---|
| gagatcgtgc tgacccagag ccccggcacc ctgagcctga gccccggcga gcgcgccacc | 60 |
| ctgagctgcc gcgccagcca gcgcgtgagc agcagctacc tggcctggta ccagcagaag | 120 |
| cccggccagg cccccgcct gctgatctac gacgccagca gccgcgccac cggcatcccc | 180 |
| gaccgcttca gcggcagcgg cagcggcacc gacttcaccc tgaccatcag ccgcctggag | 240 |
| cccgaggact tcgccgtgta ctactgccag cagtacggca gcctgccctg gaccttcggc | 300 |
| cagggcacca aggtggagat caagcgcacc gtggccgccc ccagcgtgtt catcttcccc | 360 |
| cccagcgacg agcagctgaa gagcggcacc gccagcgtgg tgtgcctgct gaacaacttc | 420 |
| taccccgcg aggccaaggt gcagtggaag gtggacaacg ccctgcagag cggcaacagc | 480 |
| caggagagcg tgaccgagca ggacagcaag acagcaccct acagcctgag cagcaccctg | 540 |
| accctgagca aggccgacta cgagaagcac aaggtgtacg cctgcgaggt gacccaccag | 600 |
| ggcctgagca gccccgtgac caagagcttc aaccgcggcg agtgc | 645 |

<210> SEQ ID NO 84
<211> LENGTH: 451
<212> TYPE: PRT
<213> ORGANISM: Artificial Sequence
<220> FEATURE:
<223> OTHER INFORMATION: dur-Fc9

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Gly Gly Trp Phe Gly Glu Leu Ala Phe Asp Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
    130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Ala Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 85
<211> LENGTH: 1353
<212> TYPE: DNA
<213> ORGANISM: Artificial Sequence
<220> FEATURE:
<223> OTHER INFORMATION: gene of dur-Fc9

<400> SEQUENCE: 85
gaggtgcagc tggtggagag cggcggcggc ctggtgcagc ccggcggcag cctgcgcctg      60
agctgcgccg ccagcggctt caccttcagc cgctactgga tgagctgggt gcgccaggcc     120
cccggcaagg gcctggagtg ggtggccaac atcaagcagg acggcagcga aaagtactac     180
gtggacagcg tgaagggccg cttcaccatc agcgccgaca cgccaagaa cagcctgtac     240 ctgcagatga acagcctgcg cgccgaggac accgccgtgt actactgcgc ccgcgagggc     300
```

```
ggctggttcg gcgagctggc cttcgactac tggggccagg gcaccctggt gaccgtgagc    360
agcgccagca ctaagggcc ctctgtgttt ccactcgccc cttctagcaa aagcacttcc    420
ggaggaactg ccgctctggg ctgtctggtg aaagattact tccccgaacc agtcactgtg    480
tcatggaact ctggagcact gacatctgga gttcacacct tcctgctgt gctgcagagt    540 tctggactgt actccctgtc atctgtggtc accgtgccat cttcatctct ggggacccag    600
acctacatct gtaacgtgaa ccacaaaccc tccaacacaa agtggacaa cgagtcgaa     660 ccaaaatctt gtgacaaaac ccacacatgc ccaccgtgcc cagctccgga actcctgggc    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca gtgcaaggt ctccaacaaa gccctcccag cccccatcga gaaaaccatc    1020
tccaaagcca agggcagcc cgagaaccca caggtgtaca ccctgccccc aagtcgggat    1080
gagctgacca gaaccaggt cagcctgtgg tgcctggtca aaggcttcta tcccagcgac    1140
atcgccgtgg agtgggagag caatgggcag ccggagaaca actacaagac cacgcctccc    1200
gtgttggact ccgacggctc cttcttcctc tacagcgcgc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353
```

<210> SEQ ID NO 86
<211> LENGTH: 11
<212> TYPE: PRT
<213> ORGANISM: Artificial Sequence
<220> FEATURE:
<223> OTHER INFORMATION: Mab806 light chain CDR1

<400> SEQUENCE: 86

His Ser Ser Gln Asp Ile Asn Ser Asn Ile Gly
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Mab806 light chain CDR2

<400> SEQUENCE: 87

His Gly Thr Asn Leu Asp Asp
1               5

<210> SEQ ID NO 88
<211> LENGTH: 9
<212> TYPE: PRT
<213> ORGANISM: Artificial Sequence
<220> FEATURE:
<223> OTHER INFORMATION: Mab806 light chain CDR3

<400> SEQUENCE: 88

Val Gln Tyr Ala Gln Phe Pro Trp Thr
1               5

<210> SEQ ID NO 89
<211> LENGTH: 107

<212> TYPE: PRT
<213> ORGANISM: Artificial Sequence
<220> FEATURE:
<223> OTHER INFORMATION: Mab806 light chain variable region

<400> SEQUENCE: 89

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys
            100                 105

<210> SEQ ID NO 90
<211> LENGTH: 6
<212> TYPE: PRT
<213> ORGANISM: Artificial Sequence
<220> FEATURE:
<223> OTHER INFORMATION: Mab806 heavy chain CDR1

<400> SEQUENCE: 90

Ser Asp Phe Ala Trp Asn
1               5

<210> SEQ ID NO 91
<211> LENGTH: 16
<212> TYPE: PRT
<213> ORGANISM: Artificial Sequence
<220> FEATURE:
<223> OTHER INFORMATION: Mab806 heavy chain CDR2

<400> SEQUENCE: 91

Tyr Ile Ser Tyr Ser Gly Asn Thr Arg Tyr Asn Pro Ser Leu Lys Ser
1               5                   10                  15

<210> SEQ ID NO 92
<211> LENGTH: 7
<212> TYPE: PRT
<213> ORGANISM: Artificial Sequence
<220> FEATURE:
<223> OTHER INFORMATION: Mab806 heavy chain CDR3

<400> SEQUENCE: 92

Ala Gly Arg Gly Phe Pro Tyr
1               5

<210> SEQ ID NO 93
<211> LENGTH: 116
<212> TYPE: PRT
<213> ORGANISM: Artificial Sequence
<220> FEATURE:
<223> OTHER INFORMATION: Mab806 heavy chain variable region

<400> SEQUENCE: 93

Asp Val Gln Leu Gln Glu Ser Gly Pro Ser Leu Val Lys Pro Ser Gln
1               5                   10                  15

-continued

```
Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
            35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ala
        115
```

<210> SEQ ID NO 94
<211> LENGTH: 11
<212> TYPE: PRT
<213> ORGANISM: Artificial Sequence
<220> FEATURE:
<223> OTHER INFORMATION: Trastuzumab light chain CDR1

<400> SEQUENCE: 94

```
Arg Ala Ser Gln Asp Val Asn Thr Ala Val Ala
1               5                   10
```

<210> SEQ ID NO 95
<211> LENGTH: 7
<212> TYPE: PRT
<213> ORGANISM: Artificial Sequence
<220> FEATURE:
<223> OTHER INFORMATION: Trastuzumab light chain CDR2

<400> SEQUENCE: 95

```
Ser Ala Ser Phe Leu Tyr Ser
1               5
```

<210> SEQ ID NO 96
<211> LENGTH: 9
<212> TYPE: PRT
<213> ORGANISM: Artificial Sequence
<220> FEATURE:
<223> OTHER INFORMATION: Trastuzumab light chain CDR3

<400> SEQUENCE: 96

```
Gln Gln His Tyr Thr Thr Pro Pro Thr
1               5
```

<210> SEQ ID NO 97
<211> LENGTH: 107
<212> TYPE: PRT
<213> ORGANISM: Artificial Sequence
<220> FEATURE:
<223> OTHER INFORMATION: Trastuzumab light chain variable region

<400> SEQUENCE: 97

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45
```

```
Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105
```

<210> SEQ ID NO 98
<211> LENGTH: 5
<212> TYPE: PRT
<213> ORGANISM: Artificial Sequence
<220> FEATURE:
<223> OTHER INFORMATION: Trastuzumab heavy chain CDR1

<400> SEQUENCE: 98

```
Asp Thr Tyr Ile His
 1               5
```

<210> SEQ ID NO 99
<211> LENGTH: 17
<212> TYPE: PRT
<213> ORGANISM: Artificial Sequence
<220> FEATURE:
<223> OTHER INFORMATION: Trastuzumab heavy chain CDR2

<400> SEQUENCE: 99

```
Arg Ile Tyr Pro Thr Asn Gly Tyr Thr Arg Tyr Ala Asp Ser Val Lys
 1               5                  10                  15

Gly
```

<210> SEQ ID NO 100
<211> LENGTH: 11
<212> TYPE: PRT
<213> ORGANISM: Artificial Sequence
<220> FEATURE:
<223> OTHER INFORMATION: Trastuzumab heavy chain CDR3

<400> SEQUENCE: 100

```
Trp Gly Gly Asp Gly Phe Tyr Ala Met Asp Tyr
 1               5                  10
```

<210> SEQ ID NO 101
<211> LENGTH: 120
<212> TYPE: PRT
<213> ORGANISM: Artificial Sequence
<220> FEATURE:
<223> OTHER INFORMATION: Trastuzumab heavy chain variable region

<400> SEQUENCE: 101

```
Glu Val Gln Leu Val Glu Ser Gly Gly Leu Val Gln Pro Gly Gly
 1               5                  10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
         50                  55                  60

Lys Gly Arg Phe Thr Ile Ser Ala Asp Thr Ser Lys Asn Thr Ala Tyr
 65                  70                  75                  80
```

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 102
<211> LENGTH: 11
<212> TYPE: PRT
<213> ORGANISM: Artificial Sequence
<220> FEATURE:
<223> OTHER INFORMATION: Pertuzumab light chain CDR1

<400> SEQUENCE: 102

Lys Ala Ser Gln Asp Val Ser Ile Gly Val Ala
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Pertuzumab light chain CDR2

<400> SEQUENCE: 103

Ser Ala Ser Tyr Arg Tyr Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Pertuzumab light chain CDR3

<400> SEQUENCE: 104

Gln Gln Tyr Tyr Ile Tyr Pro Tyr Thr
1               5

<210> SEQ ID NO 105
<211> LENGTH: 107
<212> TYPE: PRT
<213> ORGANISM: Artificial Sequence
<220> FEATURE:
<223> OTHER INFORMATION: Pertuzumab light chain variable region

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

```
<210> SEQ ID NO 106
<211> LENGTH: 5
<212> TYPE: PRT
<213> ORGANISM: Artificial Sequence
<220> FEATURE:
<223> OTHER INFORMATION: Pertuzumab heavy chain CDR1

<400> SEQUENCE: 106

Asp Tyr Thr Met Asp
1               5

<210> SEQ ID NO 107
<211> LENGTH: 17
<212> TYPE: PRT
<213> ORGANISM: Artificial Sequence
<220> FEATURE:
<223> OTHER INFORMATION: Pertuzumab heavy chain CDR2

<400> SEQUENCE: 107

Asp Val Asn Pro Asn Ser Gly Gly Ser Ile Tyr Asn Gln Arg Phe Lys
1               5                   10                  15

Gly

<210> SEQ ID NO 108
<211> LENGTH: 10
<212> TYPE: PRT
<213> ORGANISM: Artificial Sequence
<220> FEATURE:
<223> OTHER INFORMATION: Pertuzumab heavy chain CDR3

<400> SEQUENCE: 108

Asn Leu Gly Pro Ser Phe Tyr Phe Asp Tyr
1               5                   10

<210> SEQ ID NO 109
<211> LENGTH: 119
<212> TYPE: PRT
<213> ORGANISM: Artificial Sequence
<220> FEATURE:
<223> OTHER INFORMATION: Pertuzumab heavy chain variable region

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 110
<211> LENGTH: 17
<212> TYPE: PRT
```

```
<213> ORGANISM: Artificial Sequence
<220> FEATURE:
<223> OTHER INFORMATION: 5E5 light chain CDR1

<400> SEQUENCE: 110

Lys Ser Ser Gln Ser Leu Leu Asn Ser Gly Asp Gln Lys Asn Tyr Leu
1               5                   10                  15

Thr

<210> SEQ ID NO 111
<211> LENGTH: 7
<212> TYPE: PRT
<213> ORGANISM: Artificial Sequence
<220> FEATURE:
<223> OTHER INFORMATION: 5E5 light chain CDR2

<400> SEQUENCE: 111

Trp Ala Ser Thr Arg Glu Ser
1               5

<210> SEQ ID NO 112
<211> LENGTH: 9
<212> TYPE: PRT
<213> ORGANISM: Artificial Sequence
<220> FEATURE:
<223> OTHER INFORMATION: 5E5 light chain CDR3

<400> SEQUENCE: 112

Gln Asn Asp Tyr Ser Tyr Pro Leu Thr
1               5

<210> SEQ ID NO 113
<211> LENGTH: 113
<212> TYPE: PRT
<213> ORGANISM: Artificial Sequence
<220> FEATURE:
<223> OTHER INFORMATION: 5E5 light chain variable region

<400> SEQUENCE: 113

Glu Leu Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
                20                  25                  30

Gly Asp Gln Lys Asn Tyr Leu Thr Trp Tyr Gln Gln Lys Pro Gly Gln
            35                  40                  45

Pro Pro Lys Leu Leu Ile Phe Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 114
<211> LENGTH: 5
<212> TYPE: PRT
<213> ORGANISM: Artificial Sequence
<220> FEATURE:
<223> OTHER INFORMATION: 5E5 heavy chain CDR1

<400> SEQUENCE: 114
```

```
Asp His Ala Ile His
1               5

<210> SEQ ID NO 115
<211> LENGTH: 17
<212> TYPE: PRT
<213> ORGANISM: Artificial Sequence
<220> FEATURE:
<223> OTHER INFORMATION: 5E5 heavy chain CDR2

<400> SEQUENCE: 115

His Phe Ser Pro Gly Asn Thr Asp Ile Lys Tyr Asn Asp Lys Phe Lys
1               5                   10                  15

Gly

<210> SEQ ID NO 116
<211> LENGTH: 7
<212> TYPE: PRT
<213> ORGANISM: Artificial Sequence
<220> FEATURE:
<223> OTHER INFORMATION: 5E5 heavy chain CDR3

<400> SEQUENCE: 116

Ser Thr Phe Phe Phe Asp Tyr
1               5

<210> SEQ ID NO 117
<211> LENGTH: 116
<212> TYPE: PRT
<213> ORGANISM: Artificial Sequence
<220> FEATURE:
<223> OTHER INFORMATION: 5E5 heavy chain variable region

<400> SEQUENCE: 117

Gln Val Gln Leu Gln Gln Ser Asp Ala Glu Leu Val Lys Pro Gly Ser
1               5                   10                  15

Ser Val Lys Ile Ser Cys Lys Ala Ser Gly Tyr Thr Phe Thr Asp His
                20                  25                  30

Ala Ile His Trp Val Lys Gln Lys Pro Glu Gln Gly Leu Glu Trp Ile
            35                  40                  45

Gly His Phe Ser Pro Gly Asn Thr Asp Ile Lys Tyr Asn Asp Lys Phe
        50                  55                  60

Lys Gly Lys Ala Thr Leu Thr Val Asp Arg Ser Ser Thr Ala Tyr
65                  70                  75                  80

Met Gln Leu Asn Ser Leu Thr Ser Glu Asp Ser Ala Val Tyr Phe Cys
                85                  90                  95

Lys Thr Ser Thr Phe Phe Phe Asp Tyr Trp Gly Gln Gly Thr Thr Leu
            100                 105                 110

Thr Val Ser Ser
        115

<210> SEQ ID NO 118
<211> LENGTH: 5
<212> TYPE: PRT
<213> ORGANISM: Artificial Sequence
<220> FEATURE:
<223> OTHER INFORMATION: hu56 heavy chain CDR1

<400> SEQUENCE: 118

Arg Arg Cys Met Ala
1               5
```

<210> SEQ ID NO 119
<211> LENGTH: 17
<212> TYPE: PRT
<213> ORGANISM: Artificial Sequence
<220> FEATURE:
<223> OTHER INFORMATION: hu56 heavy chain CDR2

<400> SEQUENCE: 119

Lys Leu Leu Thr Thr Ser Gly Ser Thr Tyr Leu Ala Asp Ser Val Lys
1               5                   10                  15

Gly

<210> SEQ ID NO 120
<211> LENGTH: 19
<212> TYPE: PRT
<213> ORGANISM: Artificial Sequence
<220> FEATURE:
<223> OTHER INFORMATION: hu56 heavy chain CDR3

<400> SEQUENCE: 120

Asp Ser Phe Glu Asp Pro Thr Cys Thr Leu Val Thr Ser Ser Gly Ala
1               5                   10                  15

Phe Gln Tyr

<210> SEQ ID NO 121
<211> LENGTH: 128
<212> TYPE: PRT
<213> ORGANISM: Artificial Sequence
<220> FEATURE:
<223> OTHER INFORMATION: hu56 heavy variable region

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
                20                  25                  30

Cys Met Ala Trp Phe Arg Gln Ala Pro Gly Lys Glu Arg Glu Arg Val
            35                  40                  45

Ala Lys Leu Leu Thr Thr Ser Gly Ser Thr Tyr Leu Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

<210> SEQ ID NO 122
<211> LENGTH: 473
<212> TYPE: PRT
<213> ORGANISM: Artificial Sequence
<220> FEATURE:
<223> OTHER INFORMATION: SIRPV2 without signal peptide

<400> SEQUENCE: 122

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
                20                  25                  30

```
Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser Ala Pro Val Val Ser Gly Pro Ala Ala Arg
            115                 120                 125

Ala Thr Pro Gln His Thr Val Ser Phe Thr Cys Glu Ser His Gly Phe
            130                 135                 140

Ser Pro Arg Asp Ile Thr Leu Lys Trp Phe Lys Asn Gly Asn Glu Leu
145                 150                 155                 160

Ser Asp Phe Gln Thr Asn Val Asp Pro Val Gly Glu Ser Val Ser Tyr
                165                 170                 175

Ser Ile His Ser Thr Ala Lys Val Val Leu Thr Arg Glu Asp Val His
                180                 185                 190

Ser Gln Val Ile Cys Glu Val Ala His Val Thr Leu Gln Gly Asp Pro
            195                 200                 205

Leu Arg Gly Thr Ala Asn Leu Ser Glu Thr Ile Arg Val Pro Pro Thr
            210                 215                 220

Leu Glu Val Thr Gln Gln Pro Val Arg Ala Glu Asn Gln Val Asn Val
225                 230                 235                 240

Thr Cys Gln Val Arg Lys Phe Tyr Pro Gln Arg Leu Gln Leu Thr Trp
                245                 250                 255

Leu Glu Asn Gly Asn Val Ser Arg Thr Glu Thr Ala Ser Thr Val Thr
                260                 265                 270

Glu Asn Lys Asp Gly Thr Tyr Asn Trp Met Ser Trp Leu Leu Val Asn
            275                 280                 285

Val Ser Ala His Arg Asp Asp Val Lys Leu Thr Cys Gln Val Glu His
            290                 295                 300

Asp Gly Gln Pro Ala Val Ser Lys Ser His Asp Leu Lys Val Ser Ala
305                 310                 315                 320

His Pro Lys Glu Gln Gly Ser Asn Thr Ala Ala Glu Asn Thr Gly Ser
                325                 330                 335

Asn Glu Arg Asn Ile Tyr Ile Val Val Gly Val Val Cys Thr Leu Leu
                340                 345                 350

Val Ala Leu Leu Met Ala Ala Leu Tyr Leu Val Arg Ile Arg Gln Lys
            355                 360                 365

Lys Ala Gln Gly Ser Thr Ser Ser Thr Arg Leu His Glu Pro Glu Lys
            370                 375                 380

Asn Ala Arg Glu Ile Thr Gln Asp Thr Asn Asp Ile Thr Tyr Ala Asp
385                 390                 395                 400

Leu Asn Leu Pro Lys Gly Lys Lys Pro Ala Pro Gln Ala Ala Glu Pro
                405                 410                 415

Asn Asn His Thr Glu Tyr Ala Ser Ile Gln Thr Ser Pro Gln Pro Ala
                420                 425                 430

Ser Glu Asp Thr Leu Thr Tyr Ala Asp Leu Asp Met Val His Leu Asn
            435                 440                 445
```

Arg Thr Pro Lys Gln Pro Ala Pro Lys Pro Glu Pro Ser Phe Ser Glu
            450                 455                 460

Tyr Ala Ser Val Gln Val Pro Arg Lys
465                 470

<210> SEQ ID NO 123
<211> LENGTH: 503
<212> TYPE: PRT
<213> ORGANISM: Artificial Sequence
<220> FEATURE:
<223> OTHER INFORMATION: SIRPV2 with signal peptide

<400> SEQUENCE: 123

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu His Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
        275                 280                 285

Asn Gly Asn Val Ser Arg Thr Glu Thr Ala Ser Thr Val Thr Glu Asn
    290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

```
Gln Pro Ala Val Ser Lys Ser His Asp Leu Lys Val Ser Ala His Pro
                340                 345                 350

Lys Glu Gln Gly Ser Asn Thr Ala Ala Glu Asn Thr Gly Ser Asn Glu
            355                 360                 365

Arg Asn Ile Tyr Ile Val Val Gly Val Val Cys Thr Leu Leu Val Ala
        370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
            420                 425                 430

Leu Pro Lys Gly Lys Lys Pro Ala Pro Gln Ala Ala Glu Pro Asn Asn
        435                 440                 445

His Thr Glu Tyr Ala Ser Ile Gln Thr Ser Pro Gln Pro Ala Ser Glu
450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
                500

<210> SEQ ID NO 124
<211> LENGTH: 11
<212> TYPE: PRT
<213> ORGANISM: Artificial Sequence
<220> FEATURE:
<223> OTHER INFORMATION: ate light chain CDR1

<400> SEQUENCE: 124

Arg Ala Ser Gln Asp Val Ser Thr Ala Val Ala
1               5                   10

<210> SEQ ID NO 125
<211> LENGTH: 7
<212> TYPE: PRT
<213> ORGANISM: Artificial Sequence
<220> FEATURE:
<223> OTHER INFORMATION: ate light chain CDR2

<400> SEQUENCE: 125

Ser Ala Ser Phe Leu Tyr Ser
1               5

<210> SEQ ID NO 126
<211> LENGTH: 9
<212> TYPE: PRT
<213> ORGANISM: Artificial Sequence
<220> FEATURE:
<223> OTHER INFORMATION: ate light chain CDR3

<400> SEQUENCE: 126

Gln Gln Tyr Leu Tyr His Pro Ala Thr
1               5

<210> SEQ ID NO 127
<211> LENGTH: 107
<212> TYPE: PRT
<213> ORGANISM: Artificial Sequence
<220> FEATURE:
<223> OTHER INFORMATION: ate light chain variable region
```

-continued

```
<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 128
<211> LENGTH: 5
<212> TYPE: PRT
<213> ORGANISM: Artificial Sequence
<220> FEATURE:
<223> OTHER INFORMATION: ate heavy chain CDR1

<400> SEQUENCE: 128

Asp Ser Trp Ile His
1               5

<210> SEQ ID NO 129
<211> LENGTH: 17
<212> TYPE: PRT
<213> ORGANISM: Artificial Sequence
<220> FEATURE:
<223> OTHER INFORMATION: ate heavy chain CDR2

<400> SEQUENCE: 129

Trp Ile Ser Pro Tyr Gly Gly Ser Thr Tyr Tyr Ala Asp Ser Val Lys
1               5                   10                  15

Gly

<210> SEQ ID NO 130
<211> LENGTH: 9
<212> TYPE: PRT
<213> ORGANISM: Artificial Sequence
<220> FEATURE:
<223> OTHER INFORMATION: ate heavy chain CDR3

<400> SEQUENCE: 130

Arg His Trp Pro Gly Gly Phe Asp Tyr
1               5

<210> SEQ ID NO 131
<211> LENGTH: 118
<212> TYPE: PRT
<213> ORGANISM: Artificial Sequence
<220> FEATURE:
<223> OTHER INFORMATION: ate heavy variable region

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
```

```
                20                  25                  30
Trp Ile His Trp Val Arg Gln Ala Pro Gly Lys Gly Leu Glu Trp Val
            35                  40                  45

Ala Trp Ile Ser Pro Tyr Gly Gly Ser Thr Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 132
<211> LENGTH: 14
<212> TYPE: PRT
<213> ORGANISM: Artificial Sequence
<220> FEATURE:
<223> OTHER INFORMATION: ave light chain CDR1

<400> SEQUENCE: 132

Thr Gly Thr Ser Ser Asp Val Gly Gly Tyr Asn Tyr Val Ser
 1               5                   10

<210> SEQ ID NO 133
<211> LENGTH: 7
<212> TYPE: PRT
<213> ORGANISM: Artificial Sequence
<220> FEATURE:
<223> OTHER INFORMATION: ave light chain CDR2

<400> SEQUENCE: 133

Asp Val Ser Asn Arg Pro Ser
 1               5

<210> SEQ ID NO 134
<211> LENGTH: 10
<212> TYPE: PRT
<213> ORGANISM: Artificial Sequence
<220> FEATURE:
<223> OTHER INFORMATION: ave light chain CDR3

<400> SEQUENCE: 134

Ser Ser Tyr Thr Ser Ser Ser Thr Arg Val
 1               5                   10

<210> SEQ ID NO 135
<211> LENGTH: 110
<212> TYPE: PRT
<213> ORGANISM: Artificial Sequence
<220> FEATURE:
<223> OTHER INFORMATION: ave light chain variable region

<400> SEQUENCE: 135

Gln Ser Ala Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
```

```
                50              55              60
Ser Gly Ser Lys Ser Gly Asn Thr Ala Ser Leu Thr Ile Ser Gly Leu
 65              70              75              80

Gln Ala Glu Asp Glu Ala Asp Tyr Tyr Cys Ser Ser Tyr Thr Ser Ser
                85              90              95

Ser Thr Arg Val Phe Gly Thr Gly Thr Lys Val Thr Val Leu
            100             105             110
```

<210> SEQ ID NO 136
<211> LENGTH: 5
<212> TYPE: PRT
<213> ORGANISM: Artificial Sequence
<220> FEATURE:
<223> OTHER INFORMATION: ave heavy chain CDR1

<400> SEQUENCE: 136

```
Ser Tyr Ile Met Met
 1               5
```

<210> SEQ ID NO 137
<211> LENGTH: 17
<212> TYPE: PRT
<213> ORGANISM: Artificial Sequence
<220> FEATURE:
<223> OTHER INFORMATION: ave heavy chain CDR2

<400> SEQUENCE: 137

```
Ser Ile Tyr Pro Ser Gly Gly Ile Thr Phe Tyr Ala Asp Thr Val Lys
 1               5                  10                  15

Gly
```

<210> SEQ ID NO 138
<211> LENGTH: 11
<212> TYPE: PRT
<213> ORGANISM: Artificial Sequence
<220> FEATURE:
<223> OTHER INFORMATION: ave heavy chain CDR3

<400> SEQUENCE: 138

```
Ile Lys Leu Gly Thr Val Thr Thr Val Asp Tyr
 1               5                  10
```

<210> SEQ ID NO 139
<211> LENGTH: 120
<212> TYPE: PRT
<213> ORGANISM: Artificial Sequence
<220> FEATURE:
<223> OTHER INFORMATION: ave heavy variable region

<400> SEQUENCE: 139

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Thr Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

```
Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 140
<211> LENGTH: 12
<212> TYPE: PRT
<213> ORGANISM: Artificial Sequence
<220> FEATURE:
<223> OTHER INFORMATION: dur light chain CDR1

<400> SEQUENCE: 140

Arg Ala Ser Gln Arg Val Ser Ser Ser Tyr Leu Ala
1               5                   10

<210> SEQ ID NO 141
<211> LENGTH: 7
<212> TYPE: PRT
<213> ORGANISM: Artificial Sequence
<220> FEATURE:
<223> OTHER INFORMATION: dur light chain CDR2

<400> SEQUENCE: 141

Asp Ala Ser Ser Arg Ala Thr
1               5

<210> SEQ ID NO 142
<211> LENGTH: 9
<212> TYPE: PRT
<213> ORGANISM: Artificial Sequence
<220> FEATURE:
<223> OTHER INFORMATION: dur light chain CDR3

<400> SEQUENCE: 142

Gln Gln Tyr Gly Ser Leu Pro Trp Thr
1               5

<210> SEQ ID NO 143
<211> LENGTH: 108
<212> TYPE: PRT
<213> ORGANISM: Artificial Sequence
<220> FEATURE:
<223> OTHER INFORMATION: dur light chain variable region

<400> SEQUENCE: 143

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 144
```

```
<211> LENGTH: 5
<212> TYPE: PRT
<213> ORGANISM: Artificial Sequence
<220> FEATURE:
<223> OTHER INFORMATION: dur heavy chain CDR1

<400> SEQUENCE: 144

Arg Tyr Trp Met Ser
1               5

<210> SEQ ID NO 145
<211> LENGTH: 17
<212> TYPE: PRT
<213> ORGANISM: Artificial Sequence
<220> FEATURE:
<223> OTHER INFORMATION: dur heavy chain CDR2

<400> SEQUENCE: 145

Asn Ile Lys Gln Asp Gly Ser Glu Lys Tyr Tyr Val Asp Ser Val Lys
1               5                   10                  15

Gly

<210> SEQ ID NO 146
<211> LENGTH: 12
<212> TYPE: PRT
<213> ORGANISM: Artificial Sequence
<220> FEATURE:
<223> OTHER INFORMATION: dur heavy chain CDR3

<400> SEQUENCE: 146

Glu Gly Gly Trp Phe Gly Glu Leu Ala Phe Asp Tyr
1               5                   10

<210> SEQ ID NO 147
<211> LENGTH: 121
<212> TYPE: PRT
<213> ORGANISM: Artificial Sequence
<220> FEATURE:
<223> OTHER INFORMATION: dur heavy variable region

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 148
<211> LENGTH: 351
<212> TYPE: PRT
<213> ORGANISM: Artificial Sequence
<220> FEATURE:
```

<223> OTHER INFORMATION: CV1-Fc6

<400> SEQUENCE: 148

| | | | | | | | | | | | | | | |
|---|---|---|---|---|---|---|---|---|---|---|---|---|---|---|
| Glu | Glu | Glu | Leu | Gln | Ile | Ile | Gln | Pro | Asp | Lys | Ser | Val | Leu | Val | Ala |
| 1 | | | | 5 | | | | | 10 | | | | | 15 | |

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Gly Gly Gly Ser Asp Lys Thr His
        115                 120                 125

Thr Cys Pro Pro Cys Pro Ala Pro Glu Leu Leu Gly Gly Pro Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Ser Cys Gly
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
290                 295                 300

Asp Gly Ser Phe Lys Leu Ala Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys
            340                 345                 350

<210> SEQ ID NO 149
<211> LENGTH: 1053
<212> TYPE: DNA
<213> ORGANISM: Artificial Sequence
<220> FEATURE:
<223> OTHER INFORMATION: gene of CV1-Fc6

<400> SEQUENCE: 149

```
gaagaagaac tgcagatcat ccagccggat aaatctgttc tggttgcggc tggtgaaacc      60
gcgaccctgc gttgcaccat cacctctctg ttcccggttg gtccgatcca gtggttccgt     120
ggtgcgggtc cgggtcgtgt tctgatctac aaccagcgtc agggtccgtt ccgcgtgtt     180
accaccgttt ctgacaccac caaacgtaac aacatggact ctctatatccg tatcggtaac     240
atcaccccag cggacgcggg tacctactac tgcatcaaat ccgtaaggg ttctccggac     300
gacgttgagt tcaagtctgg tgcgggtacc gaactgtctg ttcgtgcgaa accgtctgga     360
ggcggtggat cagacaaaac tcacacatgc ccaccgtgcc cagctccgga actcctgggc     420
ggaccgtcag tcttcctctt cccccaaaa cccaaggaca ccctcatgat ctcccggacc     480
cctgaggtca catgcgtgg ggtggacgtg agccacgaag accctgaggt caagttcaac     540
tggtacgtgg acggcgtgga ggtgcataat gccaagacaa agccgcggga ggagcagtac     600
aacagcacgt accgtgtggt cagcgtcctc accgtcctgc accaggactg gctgaatggc     660
aaggagtaca agtgcaaggt ctccaacaaa gccctcccag cccccatcga gaaaaccatc     720
tccaaagcca agggcagccc cgagaaccca ggtgtgta ccctgccccc atcccgggat     780
gagctgacca gaaccaggt cagcctgagt tgcgcggtca aaggcttcta tcccagcgac     840
atcgccgtgg agtgggagag caatgggcag ccggagaaca actacaagac cacgcctccc     900
gtgttggact ccgacggctc cttcaagctc gtcagcaagc tcaccgtgga caagagcagg     960
tggcagcagg ggaacgtctt ctcatgctcc gtgatgcatg aggctctgca caaccactac    1020
acgcagaaga gcctctccct gtctccgggt aaa                                   1053
```

<210> SEQ ID NO 150
<211> LENGTH: 348
<212> TYPE: PRT
<213> ORGANISM: Artificial Sequence
<220> FEATURE:
<223> OTHER INFORMATION: mSIRP-Fc6

<400> SEQUENCE: 150

```
Lys Glu Leu Lys Val Thr Gln Pro Glu Lys Ser Val Ser Val Ala Ala
1               5                   10                  15

Gly Asp Ser Thr Val Leu Ala Cys Thr Leu Thr Ser Leu Leu Pro Val
            20                  25                  30

Gly Pro Ile Arg Trp Tyr Arg Gly Val Gly Pro Ser Arg Leu Leu Ile
        35                  40                  45

Tyr Ser Phe Ala Gly Glu Tyr Val Pro Arg Ile Arg Ala Val Ser Asp
    50                  55                  60

Thr Thr Lys Arg Asn Asn Met Asp Phe Ser Ile Arg Ile Ser Ala Val
65                  70                  75                  80

Thr Pro Ala Asp Ala Gly Ile Tyr Tyr Cys Val Lys Phe Gln Lys Gly
                85                  90                  95

Ser Ser Glu Pro Asp Thr Glu Ile Gln Ser Gly Gly Gly Thr Glu Val
            100                 105                 110

Tyr Val Leu Ala Gly Gly Gly Ser Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175
```

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Ser Cys Gly Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Lys Leu Ala Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 151
<211> LENGTH: 1044
<212> TYPE: DNA
<213> ORGANISM: Artificial Sequence
<220> FEATURE:
<223> OTHER INFORMATION: gene of mSIRP-Fc6

<400> SEQUENCE: 151
aaggaactga aggtgactca gcctgagaaa tcagtgtctg ttgctgctgg ggattcgacc       60
gttctggcct gcactttgac ctccttgttg ccggtgggac ccattaggtg gtacagagga      120
gtagggccaa gccggctgtt gatctacagt ttcgcaggag aatacgttcc tcgaattaga      180
gctgtttcag atactactaa gagaaacaat atggactttt ccatccgtat cagtgctgtc      240
accccagcag atgctggcat ctactactgt gtgaagttcc agaaaggatc atcagagcct      300
gacacagaaa tacaatctgg aggggggaaca gaggtctatg tactcgccgg aggcggtgga      360
tcagacaaaa ctcacacatg cccaccgtgc ccagctccgg aactcctggg cggaccgtca      420
gtcttcctct tccccccaaa acccaaggac accctcatga tctcccggac ccctgaggtc      480
acatgcgtgg tggtggacgt gagccacgaa gaccctgagg tcaagttcaa ctggtacgtg      540
gacggcgtgg aggtgcataa tgccaagaca aagccgcggg aggagcagta caacagcacg      600
taccgtgtgg tcagcgtcct caccgtcctg caccaggact ggctgaatgg caaggagtac      660
aagtgcaagg tctccaacaa agccctccca gcccccatcg agaaaccat ctccaaagcc      720 aaagggcagc cccgagaacc acaggtgtat accctgcccc catcccggga tgagctgacc      780
aagaaccagg tcagcctgag ttgcggggtc aaaggcttct atcccagcga catcgccgtg      840
gagtgggaga gcaatgggca gccggagaac aactacaaga ccacgcctcc cgtgttggac      900
tccgacggct ccttcaagct cgccagcaag ctcaccgtgg acaagagcag gtggcagcag      960
gggaacgtct tctcatgctc cgtgatgcat gaggctctgc acaaccacta cacgcagaag     1020
agcctctccc tgtctccggg taaa                                            1044

<210> SEQ ID NO 152
<211> LENGTH: 348
<212> TYPE: PRT
<213> ORGANISM: Artificial Sequence
<220> FEATURE:
<223> OTHER INFORMATION: mSIRP-Fc

<400> SEQUENCE: 152

```
Lys Glu Leu Lys Val Thr Gln Pro Glu Lys Ser Val Ser Val Ala Ala
1               5                   10                  15

Gly Asp Ser Thr Val Leu Asn Cys Thr Leu Thr Ser Leu Leu Pro Val
            20                  25                  30

Gly Pro Ile Arg Trp Tyr Arg Gly Val Gly Pro Ser Arg Leu Leu Ile
        35                  40                  45

Tyr Ser Phe Ala Gly Glu Tyr Val Pro Arg Ile Arg Asn Val Ser Asp
    50                  55                  60

Thr Thr Lys Arg Asn Asn Met Asp Phe Ser Ile Arg Ile Ser Asn Val
65                  70                  75                  80

Thr Pro Ala Asp Ala Gly Ile Tyr Tyr Cys Val Lys Phe Gln Lys Gly
                85                  90                  95

Ser Ser Glu Pro Asp Thr Glu Ile Gln Ser Gly Gly Gly Thr Glu Val
            100                 105                 110

Tyr Val Leu Ala Gly Ala Pro Gly Gly Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

<210> SEQ ID NO 153

<211> LENGTH: 1050
<212> TYPE: DNA
<213> ORGANISM: Artificial Sequence
<220> FEATURE:
<223> OTHER INFORMATION: gene of mSIRP-Fc

<400> SEQUENCE: 153

```
aaggaactga aggtgactca gcctgagaaa tcagtgtctg ttgctgctgg ggattcgacc      60
gttctggcct gcactttgac ctccttgttg ccggtgggac ccattaggtg gtacagagga    120
gtagggccaa gccggctgtt gatctacagt ttcgcaggag aatacgttcc tcgaattaga    180
gctgtttcag atactactaa gagaaacaat atggactttt ccatccgtat cagtgctgtc    240
accccagcag atgctggcat ctactactgt gtgaagttcc agaaaggatc atcagagcct    300
gacacagaaa tacaatctgg agggggaaca gaggtctatg tactcgccgg cgcgccagga    360
ggtgacaaaa ctcacacatg cccaccgtgc ccagcaccgg aactcctggg cggaccgtca    420
gtcttcctct tccccccaaa acccaaggac accctcatga tctcccggac ccctgaggtc    480
acatgcgtgg tggtggacgt gagccacgaa gaccctgagg tcaagttcaa ctggtacgtg    540
gacggcgtgg aggtgcataa tgccaagaca aagccgcggg aggagcagta caacagcacg    600
taccgtgtgg tcagcgtcct caccgtcctg caccaggact ggctgaatgg caaggagtac    660
aagtgcaagg tctccaacaa agccctccca gcccccatcg agaaaaccat ctccaaagcc    720
aaagggcagc cccgagaacc acaggtgtac accctgcccc catcccggga tgagctgacc    780
aagaaccagg tcagcctgac ctgcctggtc aaaggcttct atcccagcga catcgccgtg    840
gagtgggaga gcaatgggca gccggagaac aactacaaga ccacgcctcc cgtgttggac    900
tccgacggct ccttcttcct ctacagcaag ctcaccgtgg acaagagcag gtggcagcag    960
gggaacgtct tctcatgctc cgtgatgcat gaggctctgc acaaccacta cacgcagaag   1020
agcctctccc tgtctccggg taaataatag                                    1050
```

<210> SEQ ID NO 154
<211> LENGTH: 351
<212> TYPE: PRT
<213> ORGANISM: Artificial Sequence
<220> FEATURE:
<223> OTHER INFORMATION: CV1-Fc

<400> SEQUENCE: 154

```
Glu Glu Glu Leu Gln Ile Ile Gln Pro Asp Lys Ser Val Leu Val Ala
  1               5                  10                  15

Ala Gly Glu Thr Ala Thr Leu Arg Cys Thr Ile Thr Ser Leu Phe Pro
                 20                  25                  30

Val Gly Pro Ile Gln Trp Phe Arg Gly Ala Gly Pro Gly Arg Val Leu
             35                  40                  45

Ile Tyr Asn Gln Arg Gln Gly Pro Phe Pro Arg Val Thr Thr Val Ser
         50                  55                  60

Asp Thr Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser Gly Ala Pro Gly Gly Asp Lys Thr His
            115                 120                 125

Thr Cys Pro Pro Cys Pro Ala Pro Glu Leu Leu Gly Gly Pro Ser Val
```

```
        130                 135                 140
Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys
            340                 345                 350

<210> SEQ ID NO 155
<211> LENGTH: 1053
<212> TYPE: DNA
<213> ORGANISM: Artificial Sequence
<220> FEATURE:
<223> OTHER INFORMATION: gene of CV1-Fc

<400> SEQUENCE: 155
gaagaagaac tgcagatcat ccagccggat aaatctgttc tggttgcggc tggtgaaacc      60
gcgaccctgc gttgcaccat cacctctctg ttcccggttg gtccgatcca gtggttccgt     120
ggtgcgggtc cgggtcgtgt tctgatctac aaccagcgtc agggtccgtt ccgcgtgtt     180
accaccgttt ctgacaccac caaacgtaac aacatggact ctctatccg tatcggtaac     240
atcaccccag cggacgcggg tacctactac tgcatcaaat ccgtaaggg ttctccggac     300
gacgttgagt tcaagtctgg tgcgggtacc gaactgtctg ttcgtgcgaa accgtctggc     360
gcgccaggag gtgacaaaac tcacacatgc ccaccgtgcc cagcaccgga actcctgggc     420
ggaccgtcag tcttcctctt ccccccaaaa cccaaggaca ccctcatgat ctcccggacc     480
cctgaggtca catgcgtggt ggtggacgtg agccacgaag accctgaggt caagttcaac     540
tggtacgtgg acggcgtgga ggtgcataat gccaagacaa agccgcggga ggagcagtac     600
aacagcacgt accgtgtggt cagcgtcctc accgtcctgc accaggactg gctgaatggc     660
aaggagtaca agtgcaaggt ctccaacaaa gccctcccag cccccatcga gaaaaccatc     720
tccaaagcca aagggcagcc ccgagaacca caggtgtaca ccctgccccc atcccgggat     780
gagctgacca agaaccaggt cagcctgacc tgcctggtca aaggcttcta tcccagcgac     840
```

-continued

```
atcgccgtgg agtgggagag caatgggcag ccggagaaca actacaagac cacgcctccc    900
gtgttggact ccgacggctc cttcttcctc tacagcaagc tcaccgtgga caagagcagg    960
tggcagcagg ggaacgtctt ctcatgctcc gtgatgcatg aggctctgca caaccactac   1020
acgcagaaga gcctctccct gtctccgggt aaa                                1053
```

<210> SEQ ID NO 156
<211> LENGTH: 450
<212> TYPE: PRT
<213> ORGANISM: Artificial Sequence
<220> FEATURE:
<223> OTHER INFORMATION: amino acid of T-HC

<400> SEQUENCE: 156

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                325                 330                 335
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 157
<211> LENGTH: 1350
<212> TYPE: DNA
<213> ORGANISM: Artificial Sequence
<220> FEATURE:
<223> OTHER INFORMATION: gene of T-HC

<400> SEQUENCE: 157
gaagtccagc tggtcgaatc cggtggcggg ctggtccagc caggaggatc tctgagactg      60
tcctgcgccg caagcggctt caacatcaag gatacataca tccactgggt gaggcaggca     120
cccggcaaag gctggagtg gtggcccgg atctacccaa ccaacggtta taccaggtat     180
gccgactcag tcaaaggcag gtttactatt tctgctgaca catcaaagaa tacagcctac     240
ctgcaaatga atagcctgag ggctgaagat accgctgtgt actactgctc agatggggga     300
ggtgatggct tttatgccat ggattattgg ggacaaggca cactcgtgac cgtttcttct     360
gccagcacta agggggcctc tgtgtttcca ctcgccccct tctagcaaaag cacttccgga     420 ggcactgcag cactcgggtg tctggtcaaa gattatttcc ctgagccagt caccgtgagc     480
tggaactctg gcgccctcac ctccggggtt cacacctttc cagccgtcct gcagtcctcc     540
ggcctgtact ccctgagcag cgtcgttacc gtgccatcct cttctctggg acccagaca     600 tacatctgca atgtcaacca taagcctagc aacaccaagg tggacaaaaa ggtcgagcca     660
aagagctgcg ataagacaca cacctgccct ccatgccccg cacctgaact cctgggcggg     720
ccttccgttt tcctgttttc tcccaagccc aaggatacac tgatgattag ccgcaccccc     780
gaagtcactt gcgtggtggt ggatgtgagc catgaagatc cagaagttaa gtttaactgg     840
tatgtggacg gggtcgaggt gcacaatgct aaaacaaagc caggaggaag caatataac     900 tccacataca gagtggtgtc cgttctgaca gtcctgcacc aggactggct gaacgggaag     960
gaatacaagt gcaaggtgtc taataaggca ctgccagccc ccatagagaa gacaatctct    1020
aaagctaaag gccaaccacg cgagcctcag gtctacacac tgccaccatc cagggacgaa    1080
ctgaccaaga tcaggtgag cctgacttgt ctcgtcaaag gattctaccc aagcgacatc    1140
gccgtggagt gggaatccaa cggccaacca gagaacaact acaagaccac cccaccagtc    1200
ctggactctg atgggagctt tttcctgtat tccaagctga cagtggacaa gtctcggtgg    1260
caacagggca acgtgttcag ctgctccgtg atgcatgaag ccctgcataa ccactatacc    1320
```
cagaaaagcc tcagcctgtc ccccgggaaa                                    1350

<210> SEQ ID NO 158
<211> LENGTH: 483
<212> TYPE: PRT
<213> ORGANISM: Artificial Sequence
<220> FEATURE:
<223> OTHER INFORMATION: amino acid of mPD-L1-scFv-Fc

<400> SEQUENCE: 158

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Thr
            20                  25                  30

Lys Ala Ala Trp Tyr Trp Ile Arg Gln Ser Pro Ser Arg Gly Leu Glu
        35                  40                  45

Trp Leu Gly Arg Thr Tyr Phe Arg Ser Lys Trp Tyr Asn Asp Tyr Ala
    50                  55                  60

Asp Ser Val Lys Ser Arg Leu Thr Ile Asn Pro Asp Thr Ser Lys Asn
65                  70                  75                  80

Gln Phe Ser Leu Gln Leu Lys Ser Val Ser Pro Glu Asp Thr Ala Val
                85                  90                  95

Tyr Tyr Cys Ala Arg Gly Gln Tyr Thr Ala Phe Asp Ile Trp Gly Gln
            100                 105                 110

Gly Thr Met Val Thr Val Ser Ser Gly Ile Leu Gly Ser Gly Gly Gly
        115                 120                 125

Gly Ser Gly Gly Gly Gly Ser Gly Gly Gly Gly Ser Gln Ser Ala Leu
    130                 135                 140

Ile Gln Pro Ala Ser Val Ser Gly Ser Pro Gly Gln Ser Ile Thr Ile
145                 150                 155                 160

Ser Cys Thr Gly Thr Ser Ser Asp Val Gly Gly Tyr Asp Leu Val Ser
                165                 170                 175

Trp Tyr Gln Gln Tyr Pro Gly Gln Ala Pro Arg Leu Ile Ile Tyr Glu
            180                 185                 190

Val Ile Lys Arg Pro Ser Gly Ile Ser Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Cys Ser Tyr Ala Gly Arg Arg Leu His Gly
225                 230                 235                 240

Val Phe Gly Gly Gly Thr Gln Leu Thr Val Leu Gly Ala Pro Gly Gly
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

```
Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys

<210> SEQ ID NO 159
<211> LENGTH: 1449
<212> TYPE: DNA
<213> ORGANISM: Artificial Sequence
<220> FEATURE:
<223> OTHER INFORMATION: gene of mPD-L1-scFv-Fc

<400> SEQUENCE: 159
caggtacagc tgcagcagtc aggtccagga ctggtgaagc cctcgcagac cctctcactc      60
acctgtgcca tctccgggga cagtgtctct agcaccaagg ctgcttggta ctggatcagg     120
cagtcccctt cgagaggcct tgagtggctg gaaggacat acttccggtc caagtggtat     180
aatgactatg ccgactctgt gaaaagtcga ttaaccatca cccagacac atccaagaac     240 cagttctccc tgcaacttaa gtctgtgagt cccgaggaca cggctgtgta ttactgtgca     300
agagggcaat acactgcttt tgatatctgg ggccaaggga caatggtcac cgtctcttca     360
ggaattctag gatccggtgg cggtggcagc ggcggtggtg gttccggagg cggcggttct     420
cagtctgctc tgattcagcc tgcctccgtg tctgggtccc ctggacagtc gatcactatc     480
tcctgtactg gcaccagtag tgatgttgga ggttatgacc ttgtctcctg gtaccaacag     540
tacccgggcc aagcccccag actcatcatt tatgaggtca ttaagcggcc ctcagggatt     600
tctgatcgct tctctggttc caagtctggc aacacggcct ccctgacaat ctctgggctc     660
caggctgagg acgaggctga ttattattgc tgctcatatg caggtagacg tcttcatggt     720
gtgttcggag gaggcaccca gctgaccgtc ctcggcgcgc aggaggtga caaaactcac     780 acatgcccac cgtgcccagc accggaactc ctgggcggac cgtcagtctt cctcttcccc     840
ccaaaaccca aggacaccct catgatctcc cggacccctg aggtcacatg cgtggtggtg     900
gacgtgagcc acgaagaccc tgaggtcaag ttcaactggt acgtggacgg cgtggaggtg     960
cataatgcca agacaaagcc gcgggaggag cagtacaaca gcacgtaccg tgtggtcagc    1020
gtcctcaccg tcctgcacca ggactggctg aatggcaagg agtacaagtg caaggtctcc    1080
aacaaagccc tcccagcccc catcgagaaa accatctcca agccaaagg gcagccccga    1140 gaaccacagg tgtacaccct gcccccatcc cgggatgagc tgaccaagaa ccaggtcagc    1200
ctgacctgcc tggtcaaagg cttctatccc agcgacatcg ccgtggagtg ggagagcaat    1260
gggcagccgg agaacaacta caagaccacg cctcccgtgt ggactccga cggctccttc    1320
```

```
ttcctctaca gcaagctcac cgtggacaag agcaggtggc agcagggaa cgtcttctca    1380 tgctccgtga tgcatgaggc tctgcacaac cactacacgc agaagagcct ctccctgtct   1440
ccgggtaaa                                                            1449
```

<210> SEQ ID NO 160
<211> LENGTH: 475
<212> TYPE: PRT
<213> ORGANISM: Artificial Sequence
<220> FEATURE:
<223> OTHER INFORMATION: amino acid of mCD47-scFv-Fc

<400> SEQUENCE: 160

```
Gln Val Lys Leu Leu Gln Ser Gly Ala Ala Leu Val Lys Pro Gly Ala
1               5                   10                  15

Ser Val Lys Met Ser Cys Gln Ala Ser Gly Tyr Ser Phe Thr Asp Tyr
            20                  25                  30

Trp Val Thr Trp Val Lys Gln Ser His Gly Gln Ser Leu Glu Trp Ile
        35                  40                  45

Gly Glu Ile Tyr Pro Ser Asn Thr Val Thr Asn Phe Asn Asp Asn Phe
    50                  55                  60

Lys Gly Lys Ala Thr Leu Thr Val Asp Lys Ser Ser Thr Thr Ala Tyr
65                  70                  75                  80

Met Glu Leu Ser Arg Leu Thr Ser Glu Asp Ser Ala Ile Tyr Tyr Cys
                85                  90                  95

Thr Arg Leu Gly Asn Ser Gly Tyr Arg Val Gly Trp Phe Leu Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Asp Ile Gln Leu Thr Gln Ser
    130                 135                 140

Pro Ala Leu Ala Val Ser Pro Gly Glu Arg Val Thr Ile Ser Cys Lys
145                 150                 155                 160

Ala Ser Glu Ser Val Ser Ser His Met His Trp Tyr Gln Gln Lys Pro
                165                 170                 175

Gly Gln Gln Pro Lys Leu Leu Ile Tyr Lys Ala Ser Asn Leu Ala Ser
            180                 185                 190

Gly Val Pro Ala Arg Phe Ser Gly Ser Gly Ser Gly Thr Asp Phe Thr
        195                 200                 205

Leu Thr Ile Asp Pro Val Glu Ala Asp Asp Thr Ala Thr Tyr Phe Cys
    210                 215                 220

Gln Gln Gly Trp Asn Gly Pro Phe Thr Phe Gly Ala Gly Thr Arg Leu
225                 230                 235                 240

Glu Leu Lys Gly Ala Pro Gly Gly Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335
```

```
Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 161
<211> LENGTH: 1425
<212> TYPE: DNA
<213> ORGANISM: Artificial Sequence
<220> FEATURE:
<223> OTHER INFORMATION: gene of mCD47-scFv-Fc

<400> SEQUENCE: 161

```
caggtcaagc tgctgcagtc tggggctgca ctggtgaagc ctggagcctc tgtgaagatg     60
tcttgccaag cctctggtta ttcattcact gactactggg tgacctgggt gaagcagagt    120
catggacaga gccttgagtg gattggggaa atttatccta gcaatactgt tactaacttc    180
aatgataact caagggcaa ggccacattg actgtagaca atccaccag cacagcctat     240
atggagctca gcagattgac atctgaggac tctgcaatct attactgtac aagattgggg    300
aattcggggt acagagttgg ttggtttctt tactgggggcc aaggcactct ggtcactgtc    360
agcagcggag gaggaggaag cggaggagga ggaagcggag gaggcggcag cgacatccag    420
ctgactcagt ctcctgcttt ggctgtgtct cctggagaga gggttaccat ctcctgtaag    480
gccagtgaaa gtgtcagttc acatatgcac tggtaccaac agaaaccagg acagcaaccc    540
aaactcctca tctataaagc atcaaaccta gcatctgggg tccctgccag gttcagtggc    600
agtgggtctg ggacagactt caccctcacc attgatcctg tggaggctga tgacactgca    660
acctacttct gtcagcaggg ttggaatggt ccgttcacgt ttggagctgg gaccaggctg    720
gaactgaaag gcgcgccagg aggtgacaaa actcacacat gcccaccgtg cccagcaccg    780
gaactcctgg gcggaccgtc agtcttcctc ttccccccaa aacccaagga caccctcatg    840
atctccggga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caaagggcag ccccgagaac cacaggtgta caccctgccc   1140
ccatcccggg atgagctgac caagaaccag gtcagcctga cctgcctggt caaaggcttc   1200
tatcccagcg acatcgccgt ggagtgggag agcaatgggc agccggagaa caactacaag   1260
```

```
accacgcctc ccgtgttgga ctccgacggc tccttcttcc tctacagcaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaa                    1425
```

<210> SEQ ID NO 162
<211> LENGTH: 475
<212> TYPE: PRT
<213> ORGANISM: Artificial Sequence
<220> FEATURE:
<223> OTHER INFORMATION: amino acid of mCD47-scFv-Fc6

<400> SEQUENCE: 162

```
Gln Val Lys Leu Leu Gln Ser Gly Ala Ala Leu Val Lys Pro Gly Ala
1               5                   10                  15

Ser Val Lys Met Ser Cys Gln Ala Ser Gly Tyr Ser Phe Thr Asp Tyr
            20                  25                  30

Trp Val Thr Trp Val Lys Gln Ser His Gly Gln Ser Leu Glu Trp Ile
        35                  40                  45

Gly Glu Ile Tyr Pro Ser Asn Thr Val Thr Asn Phe Asn Asp Asn Phe
    50                  55                  60

Lys Gly Lys Ala Thr Leu Thr Val Asp Lys Ser Ser Thr Thr Ala Tyr
65                  70                  75                  80

Met Glu Leu Ser Arg Leu Thr Ser Glu Asp Ser Ala Ile Tyr Tyr Cys
                85                  90                  95

Thr Arg Leu Gly Asn Ser Gly Tyr Arg Val Gly Trp Phe Leu Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Asp Ile Gln Leu Thr Gln Ser
    130                 135                 140

Pro Ala Leu Ala Val Ser Pro Gly Glu Arg Val Thr Ile Ser Cys Lys
145                 150                 155                 160

Ala Ser Glu Ser Val Ser Ser His Met His Trp Tyr Gln Gln Lys Pro
                165                 170                 175

Gly Gln Gln Pro Lys Leu Leu Ile Tyr Lys Ala Ser Asn Leu Ala Ser
            180                 185                 190

Gly Val Pro Ala Arg Phe Ser Gly Ser Gly Ser Gly Thr Asp Phe Thr
        195                 200                 205

Leu Thr Ile Asp Pro Val Glu Ala Asp Asp Thr Ala Thr Tyr Phe Cys
    210                 215                 220

Gln Gln Gly Trp Asn Gly Pro Phe Thr Phe Gly Ala Gly Thr Arg Leu
225                 230                 235                 240

Glu Leu Lys Gly Gly Gly Gly Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335
```

```
Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Ser Cys Gly Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Lys Leu Ala Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475

<210> SEQ ID NO 163
<211> LENGTH: 1425
<212> TYPE: DNA
<213> ORGANISM: Artificial Sequence
<220> FEATURE:
<223> OTHER INFORMATION: gene of mCD47-scFv-Fc6

<400> SEQUENCE: 163
caggtcaagc tgctgcagtc tggggctgca ctggtgaagc ctggagcctc tgtgaagatg      60
tcttgccaag cctctggtta ttcattcact gactactggg tgacctgggt gaagcagagt     120
catggacaga gccttgagtg gattgggaa atttatccta gcaatactgt tactaacttc      180
aatgataact tcaagggcaa ggccacattg actgtagaca atccaccag cacagcctat      240
atggagctca gcagattgac atctgaggac tctgcaatct attactgtac aagattgggg     300
aattcggggt acagagttgg ttggtttctt tactgggggcc aaggcactct ggtcactgtc     360
agcagcggag gaggaggaag cggaggagga ggaagcggag gaggcggcag cgacatccag     420
ctgactcagt ctcctgcttt ggctgtgtct cctggagaga gggttaccat ctcctgtaag     480
gccagtgaaa gtgtcagttc acatatgcac tggtaccaac agaaaccagg acagcaaccc     540
aaactcctca tctataaagc atcaaaccta gcatctgggg tccctgccag gttcagtggc     600
agtgggtctg gacagactt caccctcacc attgatcctg tggaggctga tgacactgca     660
acctacttct gtcagcaggg ttggaatggt ccgttcacgt ttggagctgg gaccaggctg     720
gaactgaaag gaggcggtgg atcagacaaa actcacacat gcccaccgtg cccagctccg     780
gaactcctgg gcggaccgtc agtcttcctc ttccccccaa aacccaagga caccctcatg     840
atctcccgga cccctgaggt cacatgcgtg gtggtggacg tgagccacga agaccctgag     900
gtcaagttca actggtacgt ggacggcgtg gaggtgcata atgccaagac aaagccgcgg     960
gaggagcagt acaacagcac gtaccgtgtg gtcagcgtcc tcaccgtcct gcaccaggac    1020
tggctgaatg gcaaggagta caagtgcaag gtctccaaca aagccctccc agcccccatc    1080
gagaaaacca tctccaaagc caaagggcag ccccgagaac cacaggtgta ccctgccc      1140
ccatcccggg atgagctgac caagaaccag gtcagcctga gttgcgggt caaaggcttc     1200
tatcccagcg acatcgccgt ggagtgggag agcaatgggc agccggagaa caactacaag    1260
```

```
accacgcctc ccgtgttgga ctccgacggc tccttcaagc tcgccagcaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaa                    1425
```

<210> SEQ ID NO 164
<211> LENGTH: 450
<212> TYPE: PRT
<213> ORGANISM: Artificial Sequence
<220> FEATURE:
<223> OTHER INFORMATION: amino acid of AB6.12-HC

<400> SEQUENCE: 164

```
Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Gln Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 165
<211> LENGTH: 1350
<212> TYPE: DNA
<213> ORGANISM: Artificial Sequence
<220> FEATURE:
<223> OTHER INFORMATION: gene of AB6.12-HC

<400> SEQUENCE: 165
cagatgcagc tggtgcagag cggcgccgaa gtgaagaaga ccggcagcag cgtgaaggtg      60
agctgcaagg ccagcggctt caacatcaag gactactacc tgcactgggt gagacaggcc     120
cctggacagg ccctggagtg gatgggctgg atcgaccctg accagggcga caccgagtac     180
gcccagaagt tccaggacag ggtgaccatc accagggaca ggagcatgag caccgcctac     240
atggagctga gcagcctgag gagcgaggac accgccatgt actactgcaa cgccgcctac     300
ggcagcagca gctaccccat ggactactgg ggccagggaa ccaccgtgac cgtgagcagc     360
gccagcacta gggggccctc tgtgtttcca ctcgcccctt ctagcaaaag cacttccgga     420
ggcactgcag cactcggggtg tctggtcaaa gattatttcc ctgagccagt caccgtgagc     480
tggaactctg gcgccctcac ctccggggtt cacacctttc cagccgtcct gcagtcctcc     540
ggcctgtact ccctgagcag cgtcgttacc gtgccatcct cttctctggg gacccagaca     600
tacatctgca atgtcaacca taagcctagc aacaccaagg tggacaaaaa ggtcgagcca     660
aagagctgcg ataagacaca cacctgcccc ccatgccccg cacctgaact cctgggcggg     720
ccttccgttt tcctgtttcc tcccaagccc aaggatacac tgatgattag ccgcacccc     780 gaagtcactt gcgtggtggt ggatgtgagc catgaagatc cagaagttaa gtttaactgg     840
tatgtggacg gggtcgaggt gcacaatgct aaaacaaagc caggggagga gcaatataac     900
tccacataca gagtggtgtc cgttctgaca gtcctgcacc aggactggct gaacgggaag     960
gaatacaagt gcaaggtgtc taataaggca ctgccagccc ccatagagaa gacaatctct    1020
aaagctaaag ccaaccacg cgagcctcag gtctacacac tgccaccatc cagggacgaa    1080
ctgaccaaga tcaggtgag cctgacttgt ctcgtcaaag gattctaccc aagcgacatc    1140
gccgtggagt gggaatccaa cggccaacca gagaacaact acaagaccac cccaccagtc    1200
ctggactctg atgggagctt tttcctgtat tccaagctga cagtggacaa gtctcggtgg    1260
caacagggca acgtgttcag ctgctccgtg atgcatgaag ccctgcataa ccactatacc    1320
```
cagaaaagcc tcagcctgtc ccccgggaaa                                        1350

<210> SEQ ID NO 166
<211> LENGTH: 214
<212> TYPE: PRT
<213> ORGANISM: Artificial Sequence
<220> FEATURE:
<223> OTHER INFORMATION: amino acid of AB6.12-LC

<400> SEQUENCE: 166

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 167
<211> LENGTH: 639
<212> TYPE: DNA
<213> ORGANISM: Artificial Sequence
<220> FEATURE:
<223> OTHER INFORMATION: gene of AB6.12-LC

<400> SEQUENCE: 167
aacatccaga tgacccagag ccctagcgcc atgagcgcta gcgtgggcga cagggtgacc      60
atcacctgca aggccagcca ggacatccac cgttatttaa gctggttcca gcagaagccc     120
ggcaaggtgc ccaagcacct gatctacagg gccaacaggc tggtgagcgg cgtgcctagc     180
agatttagcg gcagcggcag cggcaccgag tttacccctg accatcagca gcctgcagcc     240
gaggacttcg ccacctacta ctgcctgcag tacgacgagt tcccctacac cttcggcggc     300
ggcaccaagg tggaaatcaa gcgtacggtg gctgcaccat ctgtcttcat cttcccgcca     360
tctgatgagc agttgaaatc tggtaccgct agcgttgtgt gcctgctgaa taactttta     420 ccacgggagg ctaaggtgca gtggaaagtg gacaatgccc tccagagcgg aaatagccaa     480

```
gagtccgtta ccgaacagga ctctaaagac tctacatact ccctgtcctc cacactgacc    540
ctctccaagg ccgactatga gaaacacaag gtttacgcat gcgaggtcac acaccaggga    600
ctctcctctc ccgtgaccaa gagcttcaac cggggagaa                            639
```